United States Patent
Yanofsky et al.

(10) Patent No.: US 6,288,305 B1
(45) Date of Patent: Sep. 11, 2001

(54) SEED PLANTS CHARACTERIZED BY DELAYED SEED DISPERSAL

(75) Inventors: Martin F. Yanofsky, San Diego; Sarah Liljegren, La Jolla, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/349,677

(22) Filed: Jul. 8, 1999

Related U.S. Application Data

(62) Division of application No. 09/067,800, filed on Apr. 28, 1998, now Pat. No. 6,198,024.
(60) Provisional application No. 60/051,030, filed on Jun. 27, 1997.

(51) Int. Cl.$^7$ .............................. C12N 5/04; C12N 15/82; A01H 5/00; A01H 5/10
(52) U.S. Cl. ......................... 800/290; 435/419; 435/468; 800/298
(58) Field of Search ...................... 435/419, 410, 435/468; 800/295, 298, 287, 290, 285, 286

(56) References Cited

FOREIGN PATENT DOCUMENTS

| WO 94/23043 | 10/1994 | (WO) | C12N/15/82 |
| WO 97/13865 | 4/1997 | (WO) | C12N/15/82 |
| WO 98/22592 | 5/1998 | (WO) | C12N/15/29 |

OTHER PUBLICATIONS

Coupe et al., "Identification and characterization of a pro-line–rich mRNA that accumulates during pod development in oilseed rape (*Brassica napus* L.)," *Plant Mol. Biol.* 23:1223–1232 (1993).
Erskine, "Selection for Pod Retention and Pod Indehiscence in Lentils," *Euphytica* 34:105–112 (1985).
Flanagan et al., "Specific expression of the AGL1 MADS––box gene suggests regulatory functions in Arabidopsis gynoecium and ovule development," *The Plant Journal* 10:343–353 (1996).
Gillaspy et al., "Fruits: A Developmental Perspective," *The Plant Cell* 5:1439–1451 (1993).
Gu et al., "The Fruitfull MADS–box gene mediates cell differentiation during Arabidopsis fruit development," *Development* 125:1509–1517 (1998).
Hempel et al., "Floral determination and expression of floral regulatory genes in Arabidopsis," *Development* 124:3845–3853 (1997).
Kempin et al., "Targeted disruption in Arabidopsis," *Nature* 389:802–803 (1997).
Kim et al., "A 20 nucleotide upstream element is essential for the noplaline synthase (nas) promoter activity," *Plant Molecular Biology* 24:105–117 (1994).
Ma et al., "AGL1–AGL6, an Arabidopsis gene family with similarity to floral homeotic and transcription factor genes," *Genes & Development* 5:484–495 (1991).
Mandel and Yanofsky, "The Arabidopsis AGL8 MADS Box Gene Is Expressed in Inflorescence Meristems and Is Negatively Regulated by APETALA1," *The Plant Cell* 7:1763–1771 (1995).
Meakin and Roberts, "Dehiscence of Fruit in Oilseed Rape (*Brassica napus* L.): The Role of Cell Wall Degrading Enzymes and Ethylene," *Journal of Experimental Botany* 41:1003–1011 (1990).
Meakin and Roberts, "Dehiscence of Fruit in Oilseed Rape (*Brassica napus* L.): Anatomy of Pod Dehiscence," *Journal of Experimental Botany* 41:995–1002 (1990).
Menzel et al., "Identification of two MADS box genes that are expressed in the apical meristem of the long–day plant *Sinapis alba* in transition to flowering," *The Plant Journal* 9:399–408 (1996).
Petersen et al., "Isolation and characterization of a pod dehiscence zone–specific polygalacturonase from *Brassica napus*," *Plant Mol. Biol.* 31:517–527 (1996).
Purugganan et al., "Molecular Evolution of Flower Development: Diversification of the Plant MADS–Box Regulatory Gene Family," *Genetics* 140:345–356 (1995).
Riechmann and Meyerowitz, "MADS Domain Proteins in Plant Development," *Biol. Chem.* 378:1079–1101 (1997).
Savidge et al., "Temporal Relationship between the Transcription of Two Arabidopsis MADS Box Genes and the Floral Organ Identity Genes," *The Plant Cell* 7:721–733 (1995).
Sundaresan et al., "Patterns of gene action in plant development revealed by enhancer trap and gene trap transposable elements," *Genes Devel.* 9:1797–1810 (1995).
Yanofsky, Floral Meristems to Floral Organs: Genes Controlling Early Events in Arabidopsis Flower Development, *Annual Rev. Plant Physiol. Mol. Biol.* 46:167–188 (1995).
Yanofsky et al., "The protein encoded by the Arabidopsis homeotic gene agamous resembles transcription factors," *Nature* 346:35–39 (1990).

*Primary Examiner*—Gary Benzion
*Assistant Examiner*—Ashwin D. Mehta
(74) *Attorney, Agent, or Firm*—Townsend and Townsend and Crew LLP

(57) ABSTRACT

The present invention provides a non-naturally occurring seed plant that is characterized by delayed seed dispersal due to ectopic expression of a nucleic acid molecule encoding an AGL8-like gene product. Further provided herein is a non-naturally occurring seed plant, such as an agl1 agl5 double mutant, that is characterized by delayed seed dispersal due to suppression of AGL1 and AGL5 expression in the seed plant. The invention also provides a substantially purified dehiscence zone-selective regulatory element, which includes a nucleotide sequence that confers selective expression upon an operatively linked nucleic acid molecule in the valve margin or dehiscence zone of a seed plant. Also provided by the invention are kits for producing a transgenic seed plant characterized by delayed seed dispersal, such kits containing a dehiscence zone-selective regulatory element.

10 Claims, 19 Drawing Sheets

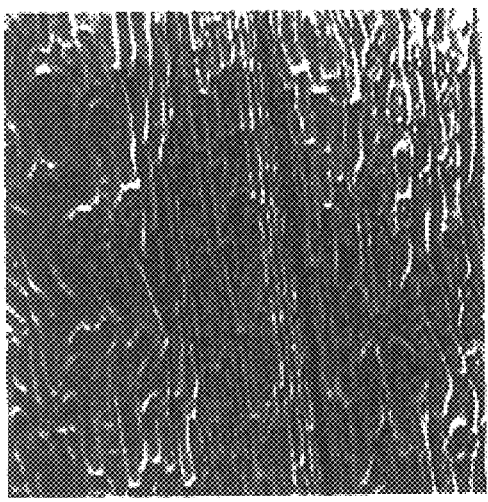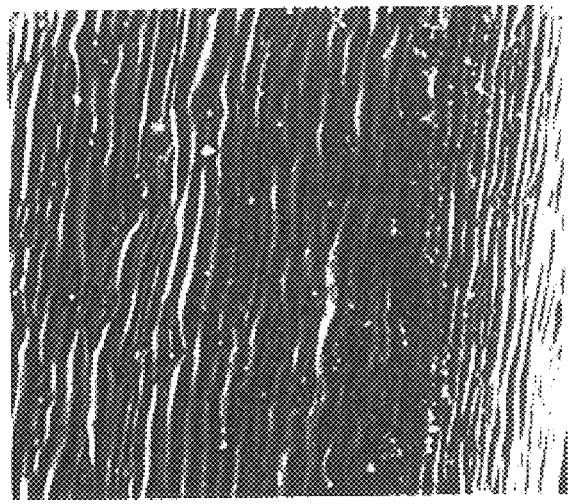
FIG. 3

```
                        CCCAGAGAGACATAAGAAAGAAAGAGAGAGAGATACTT
      TGGTCATTTCAGGGTTGTCGTTTCTCTCTCTTGTTCTTGAGATTTTGAAGAGAGAGAT
   1  ATGGGAAGAGGTAGGGTTCAGCTGAAGAGGATAGAGAACAAGATCAATAGGCAAGTTACT
   1   M  G  R  G  R  V  Q  L  K  R  I  E  N  K  I  N  R  Q  V  T

61  TTCTCAAAGAGAAGGTCTGGTTTGCTCAAGAAAGCTCATGAGATCTCTGTTCTCTGCGAT
  21   F  S  K  R  R  S  G  L  L  K  K  A  H  E  I  S  V  L  C  D

121  GCTGAGGTTGCTCTCATCGTCTTCTCTTCCAAAGGCAAACTCTTCGAATATTCCACCGAC
  41   A  E  V  A  L  I  V  F  S  S  K  G  K  L  F  E  Y  S  T  D

181  TCTTGCATGGAGAGGATACTTGAACGCTATGATCGCTATTTATATTCAGACAAACAACTT
  61   S  C  M  E  R  I  L  E  R  Y  D  R  Y  L  Y  S  D  K  Q  L

241  GTTGGCCGAGACGTTTCACAAAGTGAAAATTGGGTTCTAGAACATGCTAAGCTCAAGGCA
  81   V  G  R  D  V  S  Q  S  E  N  W  V  L  E  H  A  K  L  K  A

301  AGAGTTGAGGTACTTGAGAAGAACAAAAGGAATTTTATGGGGGAAGATCTTGATTCGTTG
 101   R  V  E  V  L  E  K  N  K  R  N  F  M  G  E  D  L  D  S  L

361  AGCTTGAAGGAGCTCCAAAGCTTGGAGCATCAGCTCGATGCAGCTATCAAGAGCATTAGG
 121   S  L  K  E  L  Q  S  L  E  H  Q  L  D  A  A  I  K  S  I  R

421  TCAAGAAAGAACCAAGCTATGTTCGAATCCATATCTGCGCTCCAGAAGAAGGATAAAGCC
 141   S  R  K  N  Q  A  M  F  E  S  I  S  A  L  Q  K  K  D  K  A

481  TTGCAAGATCACAACAATTCGCTTCTCAAAAAGATTAAGGAGAGGGAGAAGAAAACGGGT
 161   L  Q  D  H  N  N  S  L  L  K  K  I  K  E  R  E  K  K  T  G

541  CAGCAAGAAGGACAATTAGTCCAATGCTCCAACTCTTCTTCAGTTCTTCTGCCTCAATAC
 181   Q  Q  E  G  Q  L  V  Q  C  S  N  S  S  S  V  L  L  P  Q  Y

601  TGCGTAACCTCCTCCAGAGATGGCTTTGTGGAGAGAGTTGGGGGAGAGAACGGTGGTGCA
 201   C  V  T  S  S  R  D  G  F  V  E  R  V  G  G  E  N  G  G  A

661  TCGTCGTTGACGGAACCAAACTCTCTGCTTCCGGCTTGGATGTTACGTCCTACCACTACG
 221   S  S  L  T  E  P  N  S  L  L  P  A  W  M  L  R  P  T  T  T

721  AACGAGTAGAACTATCTCACTCTTTATAATATAATGATAATATAATTAATGTTTAATATT
 241   N  E  *

781  TTCATAACATTCAGCATTTTTTTGGTGACTTATACTCATTATTAATACCGATATGTTTTA
 841  GCTAGTCATATTATATGTATGATGGAACTCCGTTGTCGAGACGTATGTACGTAAGCTATC
 901  ATTAGATTCACTGCGTCTTAAGAACAAAGATTCATATCTTGGTAATGATTTCTCATGAAA
 961  TA_n
```

FIG. 6

```
                                                                        60
           *          *          *          *          *          *
AGATCTGCAA CAGTGAAAAG AGAAAACAAA ATGGACTTGA AGAGGTTTTG ACAATGCCAG
                                                                       120
           *          *          *          *          *          *
AGATAATGCT TATTCCCTAA TATGTTGCCA GCCAAGTGTC AAATTGGCTT TTTAAATATG
                                                                       180
           *          *          *          *          *          *
GATTTCTGTA TCAGTGGTCA TATTTGTGGA TCCAACGTAT TCATCATCAA GTTCTCAAGT
                                                                       240
           *          *          *          *          *          *
TTGCTTTCAG TGCAATTCTA ATTCACACGT TTAACTTTAA CATGCATGTC ATTATAATTA
                                                                       300
           *          *          *          *          *          *
CTTCTTCACT AAGACACAAT ACGGCAAACC TTTCAGATTA TATTAATCTC CATAAATGAA
                                                                       360
           *          *          *          *          *          *
ATAATTAACC TCATAATCAA GATTCAATGT TTCTAAATAT ATATGGACAA AATTTACACG
                                                                       420
           *          *          *          *          *          *
GAAGATTAGA TACGTATATT AGTAGATTTA GTCTTTCGTT TGTGCGATAA GATTAACCAC
                                                                       480
           *          *          *          *          *          *
CTCATAGATA GTAATATCAT TGTCAAATTC CTCTCGGTTT AGTCGCTAAA TTGTATCTTT
                                                                       540
           *          *          *          *          *          *
TTTAAGCCTA AAAGTAGTGT ATTCGCATAT GACTTATCGT CCTAACTTTT TTTTTAATTA
                                                                       600
           *          *          *          *          *          *
ACAAAAAAAT CGAAAAGAAA ATAATCTGTT AAATATTTTT TAAGTACTCC ATTAAGTTTA
                                                                       660
           *          *          *          *          *          *
GTTTCTATTT AAAAAATGCT TGAAATTTGA CAGTTATGTT CAACAATTTT GAATCATGAG
                                                                       720
           *          *          *          *          *          *
CGATGTCTAG ATACTCAGAA TTTAATCAAG ATGTCTTATC AAATTTGTTG TCACTCGAGG
                                                                       780
           *          *          *          *          *          *
ACCCACGCAA AAGAAAAGAC TAATATGATT TTTATTTGGT CTGGATATTT TTGTAGAGGA
                                                                       840
           *          *          *          *          *          *
TGAAACTAAG AGAGTGAAAG ATTCGAAATC CACAATGTTC AAGAGAGCTC AAAGCAAAAA
                                                                       900
           *          *          *          *          *          *
GAAAAATGAA GATGAAGGAC TAAAGAACAA TAAGCAACTA CTTATACCCT ATTTCCATAA
```

FIG. 7A

```
                                                                       960
         *         *          *          *         *         *
AGGATTCAGG TACTAGGAGA AGTTGAGGCA AGTTNNNNNN NATTGATTCA AATTTTCATT
                                                                      1020
         *         *          *          *         *         *
TATTTTTACA ATTTAATTCA CCTAAGTTAT TATGCATTTC TCATCATTGG TACATTTTCT
                                                                      1080
         *         *          *          *         *         *
GTATAGCGTA TTTACATATA TGAAATAAAT TAAATATGTC CTCACGTTGC AAGTAGTTAA
                                                                      1140
         *         *          *          *         *         *
TGAATGTCCC CACGCAAAAA AAAATCCCTC CAAATATGTC CACCTTTTCT TTTCTTTTTA
                                                                      1200
         *         *          *          *         *         *
ATTCCAAAAT TACCATAAAC TTTTGGTTTA CAAAAGATTT CTAGAAATTG AGGAAGATAT
                                                                      1260
         *         *          *          *         *         *
CCTAAATGAT TCATGAATCC TTCAATAATC TGAAGTTTGC GATATTTTCG ATTTTCTTCA
                                                                      1320
         *         *          *          *         *         *
AGAGTTGCGA TATTTGTAAT TTGGTGACCT TAAACTTTTT TTGATAAAGA GTAAACGTTT
                                                                      1380
         *         *          *          *         *         *
TTTCTTAAAA GTAAAACTTG ATTTTATGTT TTAGGGTTCT AGCTCAACTT TGTATTATAT
                                                                      1440
         *         *          *          *         *         *
TTCTTGCAAA AAGAGTTCGT TAACTGCATT CTTCAACACT ATAAAGTGAT TATCAAAAAC
                                                                      1500
         *         *          *          *         *         *
ATCTTCATGA ACATTAAGAA AAACAATATT TGGTTTCGGT TAGAGCTTGG TTTTGCTTGG
                                                                      1560
         *         *          *          *         *         *
CTTGATTCAC ATACCCATTC TAGACTTTGG CATAAATTTG ATACGATAGA GAGTATCTAA
                                                                      1620
         *         *          *          *         *         *
TGGTAATGCA GAAGGGTAAA AAAAGGAAGA GAGAAAAGGT GAGAAAGATT ACCAAAAATA
                                                                      1680
         *         *          *          *         *         *
AGGAGTTTCA AAAGATGGTT CTGATGAGAA ACAGAGCCCA TCCCTCTCCT TTTCCCCTTC
                                                                      1740
         *         *          *          *         *         *
CCATGAAAGA AATCGGATGG TCCTCCTTCA ATGTCCTCCA CCTACTCTTC TCTTCTTTCT
                                                                      1800
         *         *          *          *         *         *
TTTTTTCTTT CTTATTATTA ACCATTTAAT TAATTTCCCC TTCAATTTCA GTTTCTAGTT
                                                                      1860
         *         *          *          *         *         *
```

FIG. 7B

```
CTGTAAAAAG AAAATACACA TCTCACTTAT AGATATCCAT ATCTATTTAT ATGCATGTAT
                                                                1920
         *          *          *          *          *          *
AGAGAATAAA AAAGTGTGAG TTTCTAGGTA TGTTGAGTAT GTGCTGTTTG GACAATTGTT
                                                                1980
         *          *          *          *          *          *
AGATGATCTG TCCATTTTTT TCTTTTTTCT TCTGTGTATA AATATATTTG AGCACAAAGA
                                                                2040
         *          *          *          *          *          *
AAAACTAATA ACCTTCTGTT TTCAGCAACT AGGGTCTTAT AACCTTCAAA GAAATATTCC
                                                                2100
         *          *          *          *          *          *
TTCAATTGAA AACCCATAAA CCAAAATAGA TATTACAAAA GGAAAGAGAG ATATTTTCAA
                                                                2160
         *          *          *          *          *          *
GAACAACATA ATTAGAAAAG CAGAAGCAGC AGTTAAGTGG TACTGAGATA AATGATATAG
                                                                2220
         *          *          *          *          *          *
TTTCTCTTCA AGAACAGTTT CTCATTACCC ACCTTCTCCT TTTTGCTGAT CTATCGTAAT
                                                                2280
         *          *          *          *          *          *
CTTGAGAACT CAGGTAAGGT TGTGAATATT ATGCACCATT CATTAACCCT AAAAATAAGA
                                                                2340
         *          *          *          *          *          *
GATTTAAAAT AAATGTTTCT TCTTTCTCTG ATTCTTGTGT AACCAATTCA TGGGTTTGAT
                                                                2400
         *          *          *          *          *          *
ATGTTTCTTG GTTATTGCTT ATCAACAAAG AGATTTGATC ATTATAAAGT AGATTAATAA
                                                                2460
         *          *          *          *          *          *
CTCTTAAACA CACAAAGTTT CTTTATTTTT TAGTTACATC CCTAATTCTA GACCAGAACA
                                                                2520
         *          *          *          *          *          *
TGGATTTGAT CTATTTCTTG GTTATGTATC TTGATCAGGA AAAGGGATTT GATCATCAAG
                                                                2580
         *          *          *          *          *          *
ATTAGCCTTC TCTCTCTCTC TCTAGATATC TTTCTTGAAT TTAGAAATCT TTATTTAATT
                         translation                            2640
         *          *    start     *          *          *      *
ATTTGGTGAT GTCATATATG GATCAATGGA GGAAGGTGGG AGTAGTCACG ACGCAGAGAG
                                                                2700
         *          *          *          *          *          *
TAGCAAGAAA CTAGGGAGAG GGAAAATAGA GATAAAGAGG ATAGAGAACA CAACAAATCG  exon 1
                                                                2760
         *          *          *          *          *          *
TCAAGTTACT TTCTGCAAAC GACGCAATGG TCTTCTCAAG AAAGCTTATG AACTCTCTGT
```

FIG. 7C

```
                                                                      2820
           *          *          *          *          *           *
CTTGTGTGAT GCCGAAGTTG CCCTCGTCAT CTTCTCCACT CGTGGCCGTC TCTATGAGTA
                                                                      2880
           *          *          *          *          *           *
CGCCAACAAC AGTACGCTT CTCCTACTCT ATTTCTTGAT CTTGTTTTCT TAATTTTAAC
                                                                      2940
           *          *          *          *          *           *
TAAACAAGAT CCTAGTTCAA ATGATAACAA AGTGGGGATT GAGAGCCAAG ATTAGGGTTT
                                                                      3000
           *          *          *          *          *           *
GGTTAATTTA GAAAACCAGA TTTCACTTGT TGATACATTT AATATCTCTC TAGCTAGATT
                                                                      3060
           *          *          *          *          *           *
TAGTACTCTC TCCTCTATAT ATGTGTGGGT GTGTGTGTAA GTGTGTATAT GTATGCAAAT
                                                                      3120
           *          *          *          *          *           *
GCAAGAAGAA GAAGAAAAAG TTATCTTGTC TTCTCAAATT CTGATCAGCT TTGACCTTAG
                                                                      3180
           *          *          *          *          *           *
TTTCACTCTT TTTTCTGCAA ATCATTTGAA CCTGATGCAT GTCAGTTTCT ACAATACACT
                                                                      3240
           *          *          *          *          *           *
TTTAATTTTG ACGGCCCATC AAATTTCCTA GGGTTTACTT CAGTGAACAA AATTGGGTTC
                                                                      3300
           *          *          *          *          *           *
TTGACACGAT TTAGCATGTA TATATAAAAA TAGGGGATGA TCAAGACTTA TGTAACCTCT
                                                                      3360
           *          *          *          *          *           *
GTCTGGTGAA ACTAGGGACA AAGTCTACTG ATGAGTTGTC ACTAGGGATC CATTTGATCA
                                                                      3420
           *          *          *          *          *           *
TTTAATCCCA ACAAAAATGA AACAAAATTT TGAGAATTTA TATGCTGAAG TTTTTCAACC
                                                                      3480
           *          *          *          *          *           *
CTCTTTTTTA AATAACTTTA TATTATGTAG ATTTGTATTT AGGGTAATTT GTCCAACTAG
                                                                      3540
           *          *          *          *          *           *
AAGTCCTAAA AATCAATAAA CACACGGATG ACTTTGTCTA ACATTGTATC AGTCATCAAA
                                                                      3600
           *          *          *          *          *           *
TGTAAAATTG TACAAATAAT GAAATTAAAG ATTTAGTCTC TTTTATTTTT TTTGTTTAGG
                                                                      3660
           *          *          *          *          *           *
GTGTATATAT ATATATATAT GTATATTTGT TGCATTGATA TATCAATGAG AGGGAGAGAA
                                                                      3720
           *          *          *          *          *           *
```

FIG. 7D

```
CTCAGAGAAG TGTCGGAAAT TAAAATGGTA CGAGCCAATT GGAATCTCTG GCATTCTGAG
                                                                3780
         *          *          *          *          *          *
CTTCATTTGT TTGTTATTAG AAAAAAAAAA AAAAAATCCT TTAAAGATAC CTTCATGATG
                                                                3840
         *          *          *          *          *          *
ACATTGAATC ATGTAATATA CACGATACAT GGTCTAATTC CTCCTCAAAC CCTAATTACC
                                                                3900
         *          *          *          *          *          *
AATTTCGAAA CCATAATATT TACTAGTATG TTTATATATC CTTACTTTAA GACATTGTTT
                                                                3960
         *          *          *          *          *          *
GTTTATAATA CCTTGTGAAT TAAGAAAAAA AAAAAAAAAC TTGTGGATCT ATTCAAGCCA
                                                                4020
         *          *          *          *          *          *
TGTGTTAGAA TAAATTTATA AATTTTCTCC TCGTACTGGT CAGATATTGG TCCAAACTCC
                                                                4080
         *          *          *          *          *          *
AAAGCCTTCC CTTTTCAGGA AAAAAAACAT TTCGAAATTA ACTCTAATTA ATCAAGAATT
                                                                4140
         *          *          *          *          *          *
TCCTACAATG TATACATCTA ATGTTTTTTC CGCGATCTTA CTTATTAG TG TGAGGGGTAC
                                                                4200      exon 2
         *          *          *          *          *          *
AATTGAAAGG TACAAGAAAG CTTGTTCCGA TGCCGTCAAC CCTCCTTCCG TCACCGAAGC
                                                                4260
         *          *          *          *          *          *
TAATACTCAG GTACCAATTT ATATTGTTTG ATTCTCTTTG TTTTATCTTC TTCTTTTCAT
                                                                4320
         *          *          *          *          *          *
TATATATATG ATCAACAAAA AATATAACCT ACAAAAAGAG AGAGTTCAAG GAAATGCATT
                                                                4380
         *          *          *          *          *          *
GAAACGGTTT CGTTATGGTG TTTGAATACA TGGATTTTTG AAG TACTATC AGCAAGAAGC
                                                                4440  exon 3
         *          *          *          *          *          *
CTCTAAGCTT CGGAGGCAGA TTCGAGATAT TCAGAATTCA AATAG GTAAT TCATTAACTT
                                                                4500
         *          *          *          *          *          *
TTCATGAACT CTTCGATTTG GTATTAGGTC ACTTAATTTG GTGTCGGTCC AAAAGTCCGC
                                                                4560
         *          *          *          *          *          *
TTGTAGTTTT CTTTAGAAGT TGTTTTGTTT AATGTTCATG TTTACAAATT GAAG GCATAT
                                                                4620 exon 4
         *          *          *          *          *          *
TGTTGGGGAA TCACTTGGTT CCTTGAACTT CAAGGAACTC AAAAACCTAG AAGGACGTCT
```

FIG. 7E

```
                                                                    4680
          *         *         *         *        *        *
TGAAAAAGGA ATCAGCCGTG TCCGCTCCAA AAAG|GTAAAA TCTACGTTGC TCTCTCTCTG
                                                                    4740
          *         *         *         *        *        *
TGTCTCTGTC TCTCTCTCTA TATATAGTCC CTTAGTTTAT ATAGTTCATC ACCCTTTTGT
                                                                    4800
          *         *         *         *        *        *
GAGAATTTTG CAG|AATGAGC TGTTAGTGGC AGAGATAGAG TATATGCAGA AGAG|GTAAG  exon 5
                                                                    4860
          *         *         *         *        *        *
AACGTTTCTC CCATTCCAAG TAATTAGATC TTTCTTCGTC TTTGTGAGGG TTTGAGTTTT
                                                                    4920
          *         *         *         *        *        *
CCCATAAATC ATGTGTAG|GA AATGGAGTTG CAACACAATA ACATGTACCT GCGAGCAAAG] exon 6
                                                                    4980
          *         *         *         *        *        *
GTTAGCCACG TTCTGTTCCA AATCTTAATC TCAATATCTA CTCTTTTCTT CATTGTATAA
                                                                    5040
          *         *         *         *        *        *
CTAAGATAAC GTGAATAACA AGAAAACTTT TGTTTTTGGG TTTAATAG|AT AGCCGAAGGC
                                                                    5100
          *         *         *         *        *        *
GCCAGATTGA ATCCGGACCA GCAGGAATCG AGTGTGATAC AAGGGACGAC AGTTTACGAA
                                                                    5160
          *         *         *         *        *        *
TCCGGTGTAT CTTCTCATGA CCAGTCGCAG CATTATAATC GGAACTATAT TCCGGTGAAC
                                                                         stop
                                                                    5220 codon
          *         *         *         *        *        *
CTTCTTGAAC CGAATCAGCA ATTCTCCGGC CAAGACCAAC CTCCTCTTCA ACTTGTG|TAA]
                                                                    5280
          *         *         *         *        *        *
CTCAAAACAT GATAACTTGT TTCTTCCCCT CATAACGATT AAGAGAGAGA CGAGAGAGTT
                                                                    5340
          *         *         *         *        *        *
CATTTTATAT TTATAACGCG ACTGTGTATT CATAGTTTAG GTTCTAATAA TGATAATAAC
                                                                    5400
          *         *         *         *        *        *
AAAACTGTTG TTTCTTTGCT TAATTACATC AACATTTAAA TCCAAAGTTC TAAAACACGT
                                                                    5460
          *         *         *         *        *        *
CGAGATCCAA AGTTTGTCAT ACAAGATTAG ACGCATACAC GATCAGTTAA TAGATTTTAA
                                                                    5520
          *         *         *         *        *        *
GTGCCTTTTA ATATTTACAT ATAGTTGCAG CTTCGATTAG ATCATGTCCA CCAAACACTC
                                                                    5580
          *         *         *         *        *        *
```

FIG. 7F

Sequence Range: 1 to 6138

```
            10         20         30         40         50         60
             *          *          *          *          *          *
      GAATTCGTAA CAGAATTTAG TGAATAATAT TGTAATTACC AGGCAAGGAC TCTCCAAACG 70         80         90        100        110        120
             *          *          *          *          *          *
      GATAGCTCGA ATATCGTTAT TAAAGAGTAA ATGATCCAAT ATGTAAGCCA TTGTTGATCA 130        140        150        160        170        180
             *          *          *          *          *          *
      TCTAACATTG TTGGACTCTC TATTGCTCGA AATGATGCAT ACCTAATCAT TTATTCAGTT 190        200        210        220        230        240
             *          *          *          *          *          *
      AACTATCAAG TTGCATTTGT AAAAACCAAA CATTTAAATT CAGATTTGAT ATCACTTACA 250        260        270        280        290        300
             *          *          *          *          *          *
      GAGGATAGAG AAGCATGACT CCAGGCCTGC ATGCAACAAG AAAAAGGAAG AAAATAATGT 310        320        330        340        350        360
             *          *          *          *          *          *
      TAAAAATTTG ACAAATATAG TGTTTATTTT TATTATATGA GACAGAATTT GAATAAAATC 370        380        390        400        410        420
             *          *          *          *          *          *
      CTACCCAACT AGAGCATCAA AACGTTTTGC AATCGCAATA ATGAAACCCA TTTTCTTTTT 430        440        450        460        470        480
             *          *          *          *          *          *
      GAGTTTTTAC TCTTCTTTCA ACAGAAACTT TCTCAAACGT CTTTAGCACT GTGACGTTAG 490        500        510        520        530        540
             *          *          *          *          *          *
      ATATATACAC AAAAGCTTGA AATTTCTTCA AGCAAAAGAA TCTTTGTGGG AGTTAAGGCA 550        560        570        580        590        600
             *          *          *          *          *          *
      ACAAGCCAGG TAAAGAATCT CCAACGCATT GTTACGTTTT CATGAACCTA TTTATTATAT 610        620        630        640        650        660
             *          *          *          *          *          *
      GTTCTAAGAA AGAAAAAAAT ATCTCAAAGT AAACGTTGGA AATTTTCTGA TGAAGGGAAA 670        680        690        700        710        720
             *          *          *          *          *          *
      TCCAAAGTCT TGGGTTTAGT ATCCCTATGA ATGGTATTTG GAATATGTTT TCGTCAAAAC 730        740        750        760        770        780
             *          *          *          *          *          *
      AAAAGATTCT TTTCTTTTTC ACAAGAGTTA GTGATCAATA ACTTATGCAC TAATTAATGA 790        800        810        820        830        840
             *          *          *          *          *          *
      GATTGGACGT ATACACAATT TGATTATGAT ACTTGAGTAA AAATCACCTG TCCTTTAATT 850        860        870        880        890        900
             *          *          *          *          *          *
      TGGAAATCTC TCTTTCTTAC CCATTTATAT ACTACTTCTT TTCATTAAAA TTAAATTTCA
```

FIG. 8A

```
      910        920        930        940        950        960
       *          *          *          *          *          *
ATTATCAATC ATCGTTCAAT TTGATAAAGA TTTAACATTT TTTGTCACAG GGCTAGTAAA 970        980        990       1000       1010       1020
       *          *          *          *          *          *
AGCAATCTTT ACATAATTCA TCTTTCTTAC ATATATATAT TACCTTTTTC TTCATTAGTA 1030       1040       1050       1060       1070       1080
       *          *          *          *          *          *
TTCTATTTGA TTATGATTAT TTTGTCATAA AGCTAGTAAA TTAAACACTC GATATGAGAA 1090       1100       1110       1120       1130       1140
       *          *          *          *          *          *
TTATATTACT TCACGCTAAT TAACTCTTAA CACAACAAGA ACTAGTGCAT ATTCAACTTT 1150       1160       1170       1180       1190       1200
       *          *          *          *          *          *
CAAAGCATAT ACTATATATT GAGAATATAG ACCACGAAAG TCAATCAAAA GACCTACCAG 1210       1220       1230       1240       1250       1260
       *          *          *          *          *          *
CTCTCATCAA GTTCTTTCTT GAAATGATTT TGCAGAATTT CCAACTTAAT TAATTCGACA 1270       1280       1290       1300       1310       1320
       *          *          *          *          *          *
TGAATGTGAA AATGTGTGTT GCTCGTTAAG AAAATTGAAT AGAAGTACAA TGAAAATGAT 1330       1340       1350       1360       1370       1380
       *          *          *          *          *          *
GAGGAATGGG CAAAACACAA AAGAGTTTCC TTTCGTAACT ACAATTAATT AATGCAAATC 1390       1400       1410       1420       1430       1440
       *          *          *          *          *          *
TGAGAAAGGG TTCATGGATA ATGACTACAC ACATGATTAG TCATTCCCCG TGGGCTCTCT 1450       1460       1470       1480       1490       1500
       *          *          *          *          *          *
GCTTTCATTT ACTTTATTAG TTTCATCTTC TCTAATTATA TTGTCGCATA TATGATGCAG 1510       1520       1530       1540       1550       1560
       *          *          *          *          *          *
TTCTTTTGTC TAAATTACGT AATATGATGT AATTAATTAT CAAAATAAAT ATTCAAATTG 1570       1580       1590       1600       1610       1620
       *          *          *          *          *          *
CCGTTGGACT AACCTAATGT CCAAGATTAA GACTTGAACA TAAGAATTTT GGAAAAACTA 1630       1640       1650       1660       1670       1680
       *          *          *          *          *          *
AACCAGTTAT AATATATACT CTTAAATTGC CATTTCTGAA CACAACCAAA TAATAATATA 1690       1700       1710       1720       1730       1740
       *          *          *          *          *          *
TACTATTTAC AGTTTTTTTT AATTGGCAAG AACACTGAAA TCTTATTCAT TGTCTCGCTT 1750       1760       1770       1780       1790       1800
       *          *          *          *          *          *
GGTAGTTGAC AAGTTATAAC ACTCATATTC ATATAACCCC ATTCTAACGT TGACGACGAA 1810       1820       1830       1840       1850       1860
       *          *          *          *          *          *
```

FIG. 8B

```
CACTCATATA AACCACCCAA ATTCTTAGCA TATTAGCTAA ATATTGGTTT AATTGGAAAT
   1870       1880       1890       1900       1910       1920
     *          *          *          *          *          *
ATTTTTTTTA TATATAAAAT GCCAGGTAAA TATTAACGAC ATGCAATGTA TATAGGAGTA
   1930       1940       1950       1960       1970       1980
     *          *          *          *          *          *
GGGCAATAAA AAGAAAAGGA GAATAAAAAG GGATTACCAA AAAAGGAAAG TTTCCAAAAG
   1990       2000       2010       2020       2030       2040
     *          *          *          *          *          *
GTGATTCTGA TGAGAAACAG AGCCCATACC TCTCTTTTTT CCTCTAAACA TGAAAGAAAA
   2050       2060       2070       2080       2090       2100
     *          *          *          *          *          *
ATTGGATGGT CCTCCTTCAA TGCTCTCTCC CCACCCAATC CAAACCCAAC TGTCTTCTTT
   2110       2120       2130       2140       2150       2160
     *          *          *          *          *          *
CTTTCTTTTT TCTTCTTTCT AATTTGATAT TTTCTACCAC TTAATTCCAA TCAATTTCAA
   2170       2180       2190       2200       2210       2220
     *          *          *          *          *          *
ATTTCAATCT AAATGTATGC ATATAGAATT TAATTAAAAG AATTAGGTGT GTGATATTTG
   2230       2240       2250       2260       2270       2280
     *          *          *          *          *          *
AGAAAATGTT AGAAGTAATG GTCCATGTTC TTTCTTTCTT TTTCCTTCTA TAACACTTCA
   2290       2300       2310       2320       2330       2340
     *          *          *          *          *          *
GTTTGAAAAA AAACTACCAA ACCTTCTGTT TTCTGCAAAT GGGTTTTTAA ATACTTCCAA
   2350       2360       2370       2380       2390       2400
     *          *          *          *          *          *
AGAAATATTC CTCTAAAAGA AATTATAAAC CAAAACAGAA ACCAAAAACA AAAAATAAAG
   2410       2420       2430       2440       2450       2460
     *          *          *          *          *          *
TTGAAGCAGC AGTTAAGTGG TACTGAGATA ATAAGAATAG TATCTTTAGG CCAATGAACA
   2470       2480       2490       2500       2510       2520
     *          *          *          *          *          *
AATTAACTCT CTCATAATTC ATCTTCCCAT CCTCACTTCT CTTTCTTTCT GATATAATTA
   2530       2540       2550       2560       2570       2580  exon 1
     *          *          *          *          *          *
ATCTTGCTAA GCCAGGTATG GTTATTGATG ATTTACACTT TTTTTTAAAA GTTTCTTCCT
   2590       2600       2610       2620       2630       2640
     *          *          *          *          *          *
TTTCTCCAAT CAAATTCTTC AGTTAATCCT TATAAACCAT TTCTTTAATC CAAGGTGTTT
   2650       2660       2670       2680       2690       2700
     *          *          *          *          *          *
GAGTGCAAAA GGATTTGATC TATTTCTCTT GTGTTTATAC TTCAGCTAGG GCTTATAGAA
translation 2710       2720       2730       2740       2750       2760  exon 2
   start      *          *          *          *          *          *
ATGGAGGGTG GTGCGAGTAA TGAAGTAGCA GAGAGCAGCA AGAAGATAGG GAGAGGGAAG
```

FIG. 8C

```
         2770       2780       2790       2800       2810       2820
           *          *          *          *          *          *
     ATAGAGATAA AGAGGATAGA GAACACTACG AATCGTCAAG TCACTTTCTG CAAACGACGC 2830       2840       2850       2860       2870       2880
           *          *          *          *          *          *
     AATGGTTTAC TCAAGAAAGC TTATGAGCTC TCTGTCTTGT GTGACGCTGA GGTTGCTCTT 2890       2900       2910       2920       2930       2940
           *          *          *          *          *          *
     GTCATCTTCT CCACTCGAGG CCGTCTCTAC GAGTACGCCA ACAACAGGTA CACATCTTTT 2950       2960       2970       2980       2990       3000
           *          *          *          *          *          *
     AGCTAGATCT TGATTTTGTT GAATTTTTTT TCTAGAATAA AGTTTCGACT CTTCTGGTGG 3010       3020       3030       3040       3050       3060
           *          *          *          *          *          *
     GTTTTTCAAT CTTTATGGTC TCTTTATAGT TTTTTTCCTT AGTTTCTCTG AAGCTCAAAT 3070       3080       3090       3100       3110       3120
           *          *          *          *          *          *
     CTCTTTAAAA ATCCCCAAAA TTAGGGTTTG TTTAAAACTA GGGAACCCTA CTTTAACTTC 3130       3140       3150       3160       3170       3180
           *          *          *          *          *          *
     TTTCTCTTAG TAAAAAAGCA GTGAGGGTCT TCTCTGATCA TTAATTAGCA TCCCCCATAC 3190       3200       3210       3220       3230       3240
           *          *          *          *          *          *
     CTTGTTCCAG TCACTTTTTC TCCACAAATC CTTATAACAG TATCTATATA TGTATCTATT 3250       3260       3270       3280       3290       3300
           *          *          *          *          *          *
     TATGTCAGTT TGTACAAGAC ACTTCGATCA ATTTGATGAC CCATCAAGTT TTATTTCTGC 3310       3320       3330       3340       3350       3360
           *          *          *          *          *          *
     AGATTGATCA TTAGGTTTCC ATCATAGTAA TGAAAAAGTA GGGTTCTTGA TAAAATTATA 3370       3380       3390       3400       3410       3420
           *          *          *          *          *          *
     ATAATATATA TTATTTGGCT ATATAAAAAA GCTATGTAGA TTCCTTAAAA ATTGATTCAC 3430       3440       3450       3460       3470       3480
           *          *          *          *          *          *
     TAGGGAGAGA CTAGTAGGTG TTTGTCTTCT GACACTTCTC TAATCTTTTG GTGAATCCTT 3490       3500       3510       3520       3530       3540
           *          *          *          *          *          *
     TTGTTAAATC AAGAAAATGA ATCAGGGACA AAGCTTATTG TTGAGTCACT TAATTAATCA 3550       3560       3570       3580       3590       3600
           *          *          *          *          *          *
     TCCGATCCAT CAATCAAGAA AAATAACGAA ACAGAAAATT TTGATTTTTG ATTGTTATTT 3610       3620       3630       3640       3650       3660
           *          *          *          *          *          *
     TCTCCACTTC AAGTTGGGGA CTTGTCATTT CCGTTTTTCT ATACGTTTCC AGCTATTAAC 3670       3680       3690       3700       3710       3720
           *          *          *          *          *          *
```

FIG. 8D

```
AGCTCATGTT CATTTCACCA TTTTGATTAT TTGTCTGCTT TTTAAAGATA AATGTTTTCA
    3730       3740       3750       3760       3770       3780
     *          *          *          *          *          *
AAAATATTGT TTTTATTTGC TTGGCTAGTT AATACTATAA TTGAGGTTGA TGTATGACTA
    3790       3800       3810       3820       3830       3840
     *          *          *          *          *          *
TAATCTATAA GTCAAGTCTC ATATCATGGA TCTAAGTTAA AACTAGTAAA TTTGTAGTTT
    3850       3860       3870       3880       3890       3900
     *          *          *          *          *          *
CAATGTGAAC TTTCACAACG ACTAAAGAAC TGATCTGAAG TTTATAATGG ACATGACTAA
    3910       3920       3930       3940       3950       3960
     *          *          *          *          *          *
TTTGATTAAC AAAAGAGGAA TGCATTATGT ATGTAGAAAC ATGTGATATA TATATGTTTC
    3970       3980       3990       4000       4010       4020
     *          *          *          *          *          *
TATTATCAAA AGTGTAGTTA ACTTTCTTAT TTCAAACACC CTCATGCTTT AGTAGTATCT
    4030       4040       4050       4060       4070       4080
     *          *          *          *          *          *
TACTTTTGAC ATTTCTCAAC TTCAGCTTTC CATTATACAA CAGCACAATG TAAATTACTT
    4090       4100       4110       4120       4130       4140
     *          *          *          *          *          *
GTATATGAAT ATGAAAGCAT AACGTTATGC AAAGATTTCT AGCTTTTCTT TTTCTGTTTT
    4150       4160       4170       4180       4190       4200
     *          *          *          *          *          *
GCAAAAGATT TACAAATATC ATGTTCTTGG TAAAAACATA CTTGCCTCAG CCACATATGC
    4210       4220       4230       4240       4250       4260
     *          *          *          *          *          *
ATGTAAATGT AATGTTCAAA TATTAATTCA GGAAAAACAA AGAAGAAGCA AAATTAGCTT
    4270       4280       4290       4300       4310       4320
     *          *          *          *          *          *
CTAGAGTAGG GAATCTATTG ACTTGACCTG AAAATCACTT CTTTTTCTTA AAGCCTAGTA
    4330       4340       4350       4360       4370       4380
     *          *          *          *          *          *
GTGAATTTTT TAATCTAATT AGGCCAAAAT ATATACTAGC CTAAAATATA ATTTGGATTT
    4390       4400       4410       4420       4430       4440
     *          *          *          *          *          *
TGTGTCGTAC ATAAATTGGG ACCAATTCCA ATTAACTAAG AGCATATGCA ATTCAAATTC
    4450       4460       4470       4480       4490       4500
     *          *          *          *          *          *
TTTTTATTTT CTTCTCCGAT TTGCTACTTC TTTCTTTTGT ATGTTTTCAA ATTAGGATTA
    4510       4520       4530       4540       4550       4560
     *          *          *          *          *          *
CACTTTTTTG GGGAAGTACA CATTAGGGTC TTCTCGAACT TTGATTATAC ATATATATAT
    4570       4580       4590       4600       4610       4620
     *          *          *          *          *          *
ATATATATAT ATATAACTTT GTGAGATGTC ACTGTTAATA GATAATAGGC AATAACAATA
```

FIG. 8E

```
       4630        4640        4650        4660        4670        4680
         *           *           *           *           *           *
   ATATCCAAAA  AAGAAGGCGC  AAACAAATCA  TATACTATAT  GGTACTGGTC  CATTCACTAT 4690        4700        4710        4720        4730        4740
         *           *           *           *           *           *
   TTTGTCGGTT  GAATTTAAGG  TTTGGCGTAC  AAACTTTGTT  TCAAACCTTT  ATTATTCCGT 4750        4760        4770        4780        4790        4800
         *           *           *           *           *           *
   CTTTCTGTGT  GTTTTGTATA  TCCAGAAGAT  AAAAATATCA  ATTTCTTTAA  CGACTTCATA 4810        4820        4830        4840        4850        4860
         *           *           *           *           *           *
   TATATATATA  TATATATATA  TATATATATT  TTTCTCTTCT  GGTTTTAGTG  TTTGAATCCA 4870        4880        4890        4900        4910        4920
         *           *           *           *           *           *
   ACAGTTATAG  TTTCGTGTGT  CTTTGTTTTA  CTTGTGGTGG  TTTAAGTTTG  AGATTTTCAC 4930        4940        4950        4960        4970        4980
         *           *           *           *           *           *
   CGATTGCATC  TATTTACATA  TATAGCTACC  ACAAAAAAGA  TTGCATTTTA  AAATCTTTTC 4990        5000        5010        5020        5030        5040
         *           *           *           *           *           *
   CTTTGTGTGA  ATGTTGATGA  AGTGTGAGAG  GAACAATAGA  AAGGTACAAG  AAAGCTTGCT 5050        5060        5070        5080        5090        5100    exon 3
         *           *           *           *           *           *
   CCGACGCCGT  TAACCCTCCG  ACCATCACCG  AAGCTAATAC  TCAGGTTAGC  TTTTAATTAA 5110        5120        5130        5140        5150        5160
         *           *           *           *           *           *
   TACACCTAGC  TAGCTAGTTC  GTTAATTACT  TAATTTCTTC  TTCTTTTAGT  TATCTGACCT 5170        5180        5190        5200        5210        5220
         *           *           *           *           *           *
   TTTTTTCACC  TCTTGTAACA  ATGATGGGAT  CGAAATTGAT  GAACTACTAT  CAGCAAGAGG 5230        5240        5250        5260        5270        5280
         *           *           *           *           *           *
   CGTCTAAACT  CCGGAGACAG  ATTCGGGACA  TTCAGAATTT  GAACAGACAC  ATTCTTGGTG 5290        5300        5310        5320        5330        5340    exon 4
         *           *           *           *           *           *
   AATCTCTTGG  TTCCTTGAAC  TTTAAGGAAC  TCAAGAACCT  TGAAAGTAGG  CTTGAGAAAG 5350        5360        5370        5380        5390        5400
         *           *           *           *           *           *
   GAATCAGTCG  TGTCCGATCC  AAGAAGGTAC  ATCACTAACT  CTCCATCAAT  CTCCTTATCA 5410        5420        5430        5440        5450        5460
         *           *           *           *           *           *
   TTGAATATAT  ATCCATCTGA  TTCTTGCCCG  TTATATTTGG  TTTTTCTCTC  CAGCACGAGA 5470        5480        5490        5500        5510        5520    exon 5
         *           *           *           *           *           *
   TGTTAGTTGC  AGAGATTGAA  TACATGCAAA  AAAGGGTAAA  AGTAAAACCT  ATCTTCCTTC 5530        5540        5550        5560        5570        5580
         *           *           *           *           *           *
```

FIG. 8F

```
ACAATGAACT ACCCCTACTT TATTAGCAAC TTCTCTTTCT GATGATCATC TTTTTTATTT
   5590       5600       5610       5620       5630       5640
    *          *          *          *          *          *
TCTGTTGTCG CTTGCATTGT AGGAAATCGA GCTGCAAAAC GATAACATGT ATCTCCGCTC
   5650       5660       5670       5680       5690       5700  exon 6
    *          *          *          *          *          *
CAAGGTTTTA TACATAACTC TTTTTGGCAT TTTTGATCAT CATTTTTTTC CGGTAGACAA
   5710       5720       5730       5740       5750       5760
    *          *          *          *          *          *
TCTCTTGATG TGCAAATTCT AAATATCTCT GCAGATTACT GAAAGAACAG GTCTACAGCA
   5770       5780       5790       5800       5810       5820
    *          *          *          *          *          *
ACAAGAATCG AGTGTGATAC ATCAAGGGAC AGTTTACGAG TCGGGTGTTA CTTCTTCTCA  exon 7
   5830       5840       5850       5860       5870       5880
    *          *          *          *          *          *
CCAGTCGGGG CAGTATAACC GGAATTATAT TGCGGTTAAC CTTCTTGAAC CGAATCAGAA
   5890       5900       5910       5920       5930       5940
    *          *          *         stop        *          *
TTCCTCCAAC CAAGACCAAC CACCTCTGCA ACTTGTTTGA TTCAGTCTAA CATAAGCTTC
   5950       5960       5970       5980       5990       6000
    *          *          *          *          *          *
TTTCCTCAGC CTGAGATCGA TCTATAGTGT CACCTAAATG CGGCCGCGTC CCTCAACATC
   6010       6020       6030       6040       6050       6060
    *          *          *          *          *          *
TAGTCGCAAG CTGAGGGGAA CCACTAGTGT CATACGAACC TCCAAGAGAC GGTTACACAA
   6070       6080       6090       6100       6110       6120
    *          *          *          *          *          *
ACGGGTACAT TGTTGATGTC ATGTATGACA ATCGCCCAAG TAAGTATCCA GCTGTGTTCA
   6130
    *
GAACGTACGT CCGAATTC
```

FIG. 8G

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
       (A) LENGTH: 1062 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 101..827

(ix) FEATURE:
       (A) NAME/KEY: misc_feature
       (B) LOCATION: 1062
       (D) OTHER INFORMATION: /note= "There is a poly(A) tail at
           the end."

(ix) FEATURE:
       (A) NAME/KEY: misc_feature
       (B) LOCATION: 1..1062
       (D) OTHER INFORMATION: /note= "Nucleotide and Deduced
           Amino Acid Sequences of the AGL8 cDNA clone."

(xi) SEQUENCE DESCRIPTION: SEQ ID NO:1:

```
CCCAGAGAGA CATAAGAAAG AAAGAGAGAG AGAGATACTT TGGTCATTTC AGGGTTGTCG      60

TTTCTCTCTC TTGTTCTTGA GATTTTGAAG AGAGAGAGAT ATG GGA AGA GGT AGG      115
                                             Met Gly Arg Gly Arg
                                               1               5

GTT CAG CTG AAG AGG ATA GAG AAC AAG ATC AAT AGG CAA GTT ACT TTC      163
Val Gln Leu Lys Arg Ile Glu Asn Lys Ile Asn Arg Gln Val Thr Phe
             10                  15                  20

TCA AAG AGA AGG TCT GGT TTG CTC AAG AAA GCT CAT GAG ATC TCT GTT      211
Ser Lys Arg Arg Ser Gly Leu Leu Lys Lys Ala His Glu Ile Ser Val
         25                  30                  35

CTC TGC GAT GCT GAG GTT GCT CTC ATC GTC TTC TCT TCC AAA GGC AAA      259
Leu Cys Asp Ala Glu Val Ala Leu Ile Val Phe Ser Ser Lys Gly Lys
     40                  45                  50

CTC TTC GAA TAT TCC ACC GAC TCT TGC ATG GAG AGG ATA CTT GAA CGC      307
Leu Phe Glu Tyr Ser Thr Asp Ser Cys Met Glu Arg Ile Leu Glu Arg
 55                  60                  65

TAT GAT CGC TAT TTA TAT TCA GAC AAA CAA CTT GTT GGC CGA GAC GTT      355
Tyr Asp Arg Tyr Leu Tyr Ser Asp Lys Gln Leu Val Gly Arg Asp Val
 70                  75                  80                  85

TCA CAA AGT GAA AAT TGG GTT CTA GAA CAT GCT AAG CTC AAG GCA AGA      403
Ser Gln Ser Glu Asn Trp Val Leu Glu His Ala Lys Leu Lys Ala Arg
                 90                  95                 100

GTT GAG GTA CTT GAG AAG AAC AAA AGG AAT TTT ATG GGG GAA GAT CTT      451
Val Glu Val Leu Glu Lys Asn Lys Arg Asn Phe Met Gly Glu Asp Leu
            105                 110                 115

GAT TCG TTG AGC TTG AAG GAG CTC CAA AGC TTG GAG CAT CAG CTC GAT      499
Asp Ser Leu Ser Leu Lys Glu Leu Gln Ser Leu Glu His Gln Leu Asp
        120                 125                 130

GCA GCT ATC AAG AGC ATT AGG TCA AGA AAG AAC CAA GCT ATG TTC GAA      547
Ala Ala Ile Lys Ser Ile Arg Ser Arg Lys Asn Gln Ala Met Phe Glu
    135                 140                 145

TCC ATA TCT GCG CTC CAG AAG AAG GAT AAA GCC TTG CAA GAT CAC AAC      595
```

```
Ser Ile Ser Ala Leu Gln Lys Lys Asp Lys Ala Leu Gln Asp His Asn
150                 155                 160                 165

AAT TCG CTT CTC AAA AAG ATT AAG GAG AGG GAG AAG AAA ACG GGT CAG      643
Asn Ser Leu Leu Lys Lys Ile Lys Glu Arg Glu Lys Lys Thr Gly Gln
                170                 175                 180

CAA GAA GGA CAA TTA GTC CAA TGC TCC AAC TCT TCT TCA GTT CTT CTG      691
Gln Glu Gly Gln Leu Val Gln Cys Ser Asn Ser Ser Ser Val Leu Leu
            185                 190                 195

CCT CAA TAC TGC GTA ACC TCC TCC AGA GAT GGC TTT GTG GAG AGA GTT      739
Pro Gln Tyr Cys Val Thr Ser Ser Arg Asp Gly Phe Val Glu Arg Val
        200                 205                 210

GGG GGA GAG AAC GGT GGT GCA TCG TCG TTG ACG GAA CCA AAC TCT CTG      787
Gly Gly Glu Asn Gly Gly Ala Ser Ser Leu Thr Glu Pro Asn Ser Leu
    215                 220                 225

CTT CCG GCT TGG ATG TTA CGT CCT ACC ACT ACG AAC GAG T AGAACTATCT     837
Leu Pro Ala Trp Met Leu Arg Pro Thr Thr Thr Asn Glu
230                 235                 240

CACTCTTTAT AATATAATGA TAATATAATT AATGTTTAAT ATTTTCATAA CATTCAGCAT    897

TTTTTTGGTG ACTTATACTC ATTATTAATA CCGATATGTT TTAGCTAGTC ATATTATATG    957

TATGATGGAA CTCCGTTGTC GAGACGTATG TACGTAAGCT ATCATTAGAT TCACTGCGTC   1017

TTAAGAACAA AGATTCATAT CTTGGTAATG ATTTCTCATG AAATA                   1062

(2) INFORMATION FOR SEQ ID NO:2:

(i) SEQUENCE CHARACTERISTICS:
        (A) LENGTH: 242 amino acids
        (B) TYPE: amino acid
        (D) TOPOLOGY: linear (ii) MOLECULE TYPE: protein (xi) SEQUENCE DESCRIPTION: SEQ ID NO:2:

Met Gly Arg Gly Arg Val Gln Leu Lys Arg Ile Glu Asn Lys Ile Asn
 1               5                  10                  15

Arg Gln Val Thr Phe Ser Lys Arg Arg Ser Gly Leu Leu Lys Lys Ala
                20                  25                  30

His Glu Ile Ser Val Leu Cys Asp Ala Glu Val Ala Leu Ile Val Phe
            35                  40                  45

Ser Ser Lys Gly Lys Leu Phe Glu Tyr Ser Thr Asp Ser Cys Met Glu
    50                  55                  60

Arg Ile Leu Glu Arg Tyr Asp Arg Tyr Leu Tyr Ser Asp Lys Gln Leu
65                  70                  75                  80

Val Gly Arg Asp Val Ser Gln Ser Glu Asn Trp Val Leu Glu His Ala
                85                  90                  95

Lys Leu Lys Ala Arg Val Glu Val Leu Glu Lys Asn Lys Arg Asn Phe
            100                 105                 110

Met Gly Glu Asp Leu Asp Ser Leu Ser Leu Lys Glu Leu Gln Ser Leu
    115                 120                 125

Glu His Gln Leu Asp Ala Ala Ile Lys Ser Ile Arg Ser Arg Lys Asn
    130                 135                 140

Gln Ala Met Phe Glu Ser Ile Ser Ala Leu Gln Lys Lys Asp Lys Ala
145                 150                 155                 160

Leu Gln Asp His Asn Asn Ser Leu Leu Lys Lys Ile Lys Glu Arg Glu
                165                 170                 175

Lys Lys Thr Gly Gln Gln Glu Gly Gln Leu Val Gln Cys Ser Asn Ser
            180                 185                 190
```

```
Ser Ser Val Leu Leu Pro Gln Tyr Cys Val Thr Ser Ser Arg Asp Gly
        195                 200                 205

Phe Val Glu Arg Val Gly Gly Glu Asn Gly Gly Ala Ser Ser Leu Thr
        210                 215                 220

Glu Pro Asn Ser Leu Leu Pro Ala Trp Met Leu Arg Pro Thr Thr Thr
225                 230                 235                 240

Asn Glu (2) INFORMATION FOR SEQ ID NO:3:

(i) SEQUENCE CHARACTERISTICS:
        (A) LENGTH: 5622 base pairs
        (B) TYPE: nucleic acid
        (C) STRANDEDNESS: unknown
        (D) TOPOLOGY: unknown (ix) FEATURE:
        (A) NAME/KEY: misc_feature
        (B) LOCATION: 1..5622
        (D) OTHER INFORMATION: /label= AGL1_promoter
                /note= "Nucleotide sequence of the AGL1 promoter."

(xi) SEQUENCE DESCRIPTION: SEQ ID NO:3:
```

| | | | | | |
|---|---|---|---|---|---|
| AGATCTGCAA | CAGTGAAAAG | AGAAAACAAA | ATGGACTTGA | AGAGGTTTTG | ACAATGCCAG | 60 |
| AGATAATGCT | TATTCCCTAA | TATGTTGCCA | GCCAAGTGTC | AAATTGGCTT | TTTAAATATG | 120 |
| GATTTCTGTA | TCAGTGGTCA | TATTTGTGGA | TCCAACGTAT | TCATCATCAA | GTTCTCAAGT | 180 |
| TTGCTTTCAG | TGCAATTCTA | ATTCACACGT | TTAACTTTAA | CATGCATGTC | ATTATAATTA | 240 |
| CTTCTTCACT | AAGACACAAT | ACGGCAAACC | TTTCAGATTA | TATTAATCTC | CATAAATGAA | 300 |
| ATAATTAACC | TCATAATCAA | GATTCAATGT | TTCTAAATAT | ATATGGACAA | AATTTACACG | 360 |
| GAAGATTAGA | TACGTATATT | AGTAGATTTA | GTCTTTCGTT | TGTGCGATAA | GATTAACCAC | 420 |
| CTCATAGATA | GTAATATCAT | TGTCAAATTC | CTCTCGGTTT | AGTCGCTAAA | TTGTATCTTT | 480 |
| TTTAAGCCTA | AAAGTAGTGT | ATTCGCATAT | GACTTATCGT | CCTAACTTTT | TTTTTAATTA | 540 |
| ACAAAAAAAT | CGAAAAGAAA | ATAATCTGTT | AAATATTTTT | TAAGTACTCC | ATTAAGTTTA | 600 |
| GTTTCTATTT | AAAAAATGCT | TGAAATTTGA | CAGTTATGTT | CAACAATTTT | GAATCATGAG | 660 |
| CGATGTCTAG | ATACTCAGAA | TTTAATCAAG | ATGTCTTATC | AAATTTGTTG | TCACTCGAGG | 720 |
| ACCCACGCAA | AAGAAAGAC | TAATATGATT | TTTATTTGGT | CTGGATATTT | TTGTAGAGGA | 780 |
| TGAAACTAAG | AGAGTGAAAG | ATTCGAAATC | CACAATGTTC | AAGAGAGCTC | AAAGCAAAAA | 840 |
| GAAAAATGAA | GATGAAGGAC | TAAAGAACAA | TAAGCAACTA | CTTATACCCT | ATTTCCATAA | 900 |
| AGGATTCAGG | TACTAGGAGA | AGTTGAGGCA | AGTTNNNNNN | NATTGATTCA | AATTTTCATT | 960 |
| TATTTTTACA | ATTTAATTCA | CCTAAGTTAT | TATGCATTTC | TCATCATTGG | TACATTTTCT | 1020 |
| GTATAGCGTA | TTTACATATA | TGAAATAAAT | TAAATATGTC | CTCACGTTGC | AAGTAGTTAA | 1080 |
| TGAATGTCCC | CACGCAAAAA | AAAATCCCTC | CAAATATGTC | CACCTTTTCT | TTTCTTTTTA | 1140 |
| ATTCCAAAAT | TACCATAAAC | TTTTGGTTTA | CAAAAGATTT | CTAGAAATTG | AGGAAGATAT | 1200 |
| CCTAAATGAT | TCATGAATCC | TTCAATAATC | TGAAGTTTGC | GATATTTTCG | ATTTTCTTCA | 1260 |
| AGAGTTGCGA | TATTTGTAAT | TTGGTGACCT | TAAACTTTTT | TTGATAAAGA | GTAAACGTTT | 1320 |
| TTTCTTAAAA | GTAAAACTTG | ATTTTATGTT | TTAGGGTTCT | AGCTCAACTT | TGTATTATAT | 1380 |
| TTCTTGCAAA | AAGAGTTCGT | TAACTGCATT | CTTCAACACT | ATAAAGTGAT | TATCAAAAAC | 1440 |
| ATCTTCATGA | ACATTAAGAA | AAACAATATT | TGGTTTCGGT | TAGAGCTTGG | TTTTGCTTGG | 1500 |
| CTTGATTCAC | ATACCCATTC | TAGACTTTGG | CATAAATTTG | ATACGATAGA | GAGTATCTAA | 1560 |

```
TGGTAATGCA GAAGGGTAAA AAAAGGAAGA GAGAAAAGGT GAGAAAGATT ACCAAAAATA      1620

AGGAGTTTCA AAAGATGGTT CTGATGAGAA ACAGAGCCCA TCCCTCTCCT TTTCCCCTTC      1680

CCATGAAAGA AATCGGATGG TCCTCCTTCA ATGTCCTCCA CCTACTCTTC TCTTCTTTCT      1740

TTTTTTCTTT CTTATTATTA ACCATTTAAT TAATTTCCCC TTCAATTTCA GTTTCTAGTT      1800

CTGTAAAAAG AAAATACACA TCTCACTTAT AGATATCCAT ATCTATTTAT ATGCATGTAT      1860

AGAGAATAAA AAAGTGTGAG TTTCTAGGTA TGTTGAGTAT GTGCTGTTTG GACAATTGTT      1920

AGATGATCTG TCCATTTTTT TCTTTTTTCT TCTGTGTATA AATATATTTG AGCACAAAGA      1980

AAAACTAATA ACCTTCTGTT TTCAGCAACT AGGGTCTTAT AACCTTCAAA GAAATATTCC      2040

TTCAATTGAA AACCCATAAA CCAAAATAGA TATTACAAAA GGAAAGAGAG ATATTTTCAA      2100

GAACAACATA ATTAGAAAAG CAGAAGCAGC AGTTAAGTGG TACTGAGATA AATGATATAG      2160

TTTCTCTTCA AGAACAGTTT CTCATTACCC ACCTTCTCCT TTTTGCTGAT CTATCGTAAT      2220

CTTGAGAACT CAGGTAAGGT TGTGAATATT ATGCACCATT CATTAACCCT AAAAATAAGA      2280

GATTTAAAAT AAATGTTTCT TCTTTCTCTG ATTCTTGTGT AACCAATTCA TGGGTTTGAT      2340

ATGTTTCTTG GTTATTGCTT ATCAACAAAG AGATTTGATC ATTATAAAGT AGATTAATAA      2400

CTCTTAAACA CACAAAGTTT CTTTATTTTT TAGTTACATC CCTAATTCTA GACCAGAACA      2460

TGGATTTGAT CTATTTCTTG GTTATGTATC TTGATCAGGA AAAGGGATTT GATCATCAAG      2520

ATTAGCCTTC TCTCTCTCTC TCTAGATATC TTTCTTGAAT TTAGAAATCT TTATTTAATT      2580

ATTTGGTGAT GTCATATATG GATCAATGGA GGAAGGTGGG AGTAGTCACG ACGCAGAGAG      2640

TAGCAAGAAA CTAGGGAGAG GGAAAATAGA GATAAAGAGG ATAGAGAACA CAACAAATCG      2700

TCAAGTTACT TTCTGCAAAC GACGCAATGG TCTTCTCAAG AAAGCTTATG AACTCTCTGT      2760

CTTGTGTGAT GCCGAAGTTG CCCTCGTCAT CTTCTCCACT CGTGGCCGTC TCTATGAGTA      2820

CGCCAACAAC AGGTACGCTT CTCCTACTCT ATTTCTTGAT CTTGTTTTCT TAATTTTAAC      2880

TAAACAAGAT CCTAGTTCAA ATGATAACAA AGTGGGGATT GAGAGCCAAG ATTAGGGTTT      2940

GGTTAATTTA GAAAACCAGA TTTCACTTGT TGATACATTT AATATCTCTC TAGCTAGATT      3000

TAGTACTCTC TCCTCTATAT ATGTGTGGGT GTGTGTGTAA GTGTGTATAT GTATGCAAAT      3060

GCAAGAAGAA GAAGAAAAAG TTATCTTGTC TTCTCAAATT CTGATCAGCT TTGACCTTAG      3120

TTTCACTCTT TTTTCTGCAA ATCATTTGAA CCTGATGCAT GTCAGTTTCT ACAATACACT      3180

TTTAATTTTG ACGGCCCATC AAATTTCCTA GGGTTTACTT CAGTGAACAA AATTGGGTTC      3240

TTGACACGAT TTAGCATGTA TATATAAAAA TAGGGGATGA TCAAGACTTA TGTAACCTCT      3300

GTCTGGTGAA ACTAGGGACA AAGTCTACTG ATGAGTTGTC ACTAGGGATC CATTTGATCA      3360

TTTAATCCCA ACAAAAATGA AACAAAATTT TGAGAATTTA TATGCTGAAG TTTTTCAACC      3420

CTCTTTTTTA AATAACTTTA TATTATGTAG ATTTGTATTT AGGGTAATTT GTCCAACTAG      3480

AAGTCCTAAA AATCAATAAA CACACGGATG ACTTTGTCTA ACATTGTATC AGTCATCAAA      3540

TGTAAAATTG TACAAATAAT GAAATTAAAG ATTTAGTCTC TTTTATTTTT TTTGTTTAGG      3600

GTGTATATAT ATATATATAT GTATATTTGT TGCATTGATA TATCAATGAG AGGGAGAGAA      3660

CTCAGAGAAG TGTCGGAAAT TAAAATGGTA CGAGCCAATT GGAATCTCTG GCATTCTGAG      3720

CTTCATTTGT TTGTTATTAG AAAAAAAAAA AAAAAATCCT TTAAAGATAC CTTCATGATG      3780

ACATTGAATC ATGTAATATA CACGATACAT GGTCTAATTC CTCCTCAAAC CCTAATTACC      3840

AATTTCGAAA CCATAATATT TACTAGTATG TTTATATATC CTTACTTTAA GACATTGTTT      3900
```

```
GTTTATAATA CCTTGTGAAT TAAGAAAAAA AAAAAAAAAC TTGTGGATCT ATTCAAGCCA    3960

TGTGTTAGAA TAAATTTATA AATTTTCTCC TCGTACTGGT CAGATATTGG TCCAAACTCC    4020

AAAGCCTTCC CTTTTCAGGA AAAAAAACAT TTCGAAATTA ACTCTAATTA ATCAAGAATT    4080

TCCTACAATG TATACATCTA ATGTTTTTTC CGCGATCTTA CTTATTAGTG TGAGGGGTAC    4140

AATTGAAAGG TACAAGAAAG CTTGTTCCGA TGCCGTCAAC CCTCCTTCCG TCACCGAAGC    4200

TAATACTCAG GTACCAATTT ATATTGTTTG ATTCTCTTTG TTTTATCTTC TTCTTTTCAT    4260

TATATATATG ATCAACAAAA AATATAACCT ACAAAAAGAG AGAGTTCAAG GAAATGCATT    4320

GAAACGGTTT CGTTATGGTG TTTGAATACA TGGATTTTTG AAGTACTATC AGCAAGAAGC    4380

CTCTAAGCTT CGGAGGCAGA TTCGAGATAT TCAGAATTCA AATAGGTAAT TCATTAACTT    4440

TTCATGAACT CTTCGATTTG GTATTAGGTC ACTTAATTTG GTGTCGGTCC AAAAGTCCGC    4500

TTGTAGTTTT CTTTAGAAGT TGTTTTGTTT AATGTTCATG TTTACAAATT GAAGGCATAT    4560

TGTTGGGGAA TCACTTGGTT CCTTGAACTT CAAGGAACTC AAAAACCTAG AAGGACGTCT    4620

TGAAAAAGGA ATCAGCCGTG TCCGCTCCAA AAAGGTAAAA TCTACGTTGC TCTCTCTCTG    4680

TGTCTCTGTC TCTCTCTCTA TATATAGTCC CTTAGTTTAT ATAGTTCATC ACCCTTTTGT    4740

GAGAATTTTG CAGAATGAGC TGTTAGTGGC AGAGATAGAG TATATGCAGA AGAGGGTAAG    4800

AACGTTTCTC CCATTCCAAG TAATTAGATC TTTCTTCGTC TTTGTGAGGG TTTGAGTTTT    4860

CCCATAAATC ATGTGTAGGA AATGGAGTTG CAACACAATA ACATGTACCT GCGAGCAAAG    4920

GTTAGCCACG TTCTGTTCCA AATCTTAATC TCAATATCTA CTCTTTTCTT CATTGTATAA    4980

CTAAGATAAC GTGAATAACA AGAAAACTTT TGTTTTTGGG TTTAATAGAT AGCCGAAGGC    5040

GCCAGATTGA ATCCGGACCA GCAGGAATCG AGTGTGATAC AAGGGACGAC AGTTTACGAA    5100

TCCGGTGTAT CTTCTCATGA CCAGTCGCAG CATTATAATC GGAACTATAT TCCGGTGAAC    5160

CTTCTTGAAC CGAATCAGCA ATTCTCCGGC CAAGACCAAC CTCCTCTTCA ACTTGTGTAA    5220

CTCAAAACAT GATAACTTGT TTCTTCCCCT CATAACGATT AAGAGAGAGA CGAGAGAGTT    5280

CATTTTATAT TTATAACGCG ACTGTGTATT CATAGTTTAG GTTCTAATAA TGATAATAAC    5340

AAAACTGTTG TTTCTTTGCT TAATTACATC AACATTTAAA TCCAAAGTTC TAAAACACGT    5400

CGAGATCCAA AGTTTGTCAT ACAAGATTAG ACGCATACAC GATCAGTTAA TAGATTTTAA    5460

GTGCCTTTTA ATATTTACAT ATAGTTGCAG CTTCGATTAG ATCATGTCCA CCAAACACTC    5520

ACAATTAGAG ACAAGCAAAA CTATAAACAT TGATCATAAA ATGATTACAA CATGTCCATA    5580

AATTAATTAT GGATTACAAA ATAAAAACT TACAAAAGAT CT                       5622
```

(2) INFORMATION FOR SEQ ID NO:4:

(i) SEQUENCE CHARACTERISTICS:
        (A) LENGTH: 6138 base pairs
        (B) TYPE: nucleic acid
        (C) STRANDEDNESS: unknown
        (D) TOPOLOGY: unknown (ix) FEATURE:
        (A) NAME/KEY: misc_feature
        (B) LOCATION: 1..6138
        (D) OTHER INFORMATION: /label= AGL5_promoter
            /note= "Nucleotide sequence of the AGL5 promoter."

(xi) SEQUENCE DESCRIPTION: SEQ ID NO:4:

```
GAATTCGTAA CAGAATTTAG TGAATAATAT TGTAATTACC AGGCAAGGAC TCTCCAAACG      60

GATAGCTCGA ATATCGTTAT TAAAGAGTAA ATGATCCAAT ATGTAAGCCA TTGTTGATCA     120
```

-continued

```
TCTAACATTG TTGGACTCTC TATTGCTCGA AATGATGCAT ACCTAATCAT TTATTCAGTT      180

AACTATCAAG TTGCATTTGT AAAAACCAAA CATTTAAATT CAGATTTGAT ATCACTTACA      240

GAGGATAGAG AAGCATGACT CCAGGCCTGC ATGCAACAAA AAAAAGGAAG AAAATAATGT      300

TAAAAATTTG ACAAATATAG TGTTTATTTT TATTATATGA GACAGAATTT GAATAAAATC      360

CTACCCAACT AGAGCATCAA AACGTTTTGC AATCGCAATA ATGAAACCCA TTTTCTTTTT      420

GAGTTTTTAC TCTTCTTTCA ACAGAAACTT TCTCAAACGT CTTTAGCACT GTGACGTTAG      480

ATATATACAC AAAAGCTTGA AATTTCTTCA AGCAAAAGAA TCTTTGTGGG AGTTAAGGCA      540

ACAAGCCAGG TAAAGAATCT CCAACGCATT GTTACGTTTT CATGAACCTA TTTATTATAT      600

GTTCTAAGAA AGAAAAAAAT ATCTCAAAGT AAACGTTGGA AATTTCTGA TGAAGGGAAA       660

TCCAAAGTCT TGGGTTTAGT ATCCCTATGA ATGGTATTTG GAATATGTTT TCGTCAAAAC      720

AAAAGATTCT TTTCTTTTTC ACAAGAGTTA GTGATCAATA ACTTATGCAC TAATTAATGA      780

GATTGGACGT ATACACAATT TGATTATGAT ACTTGAGTAA AAATCACCTG TCCTTTAATT      840

TGGAAATCTC TCTTTCTTAC CCATTTATAT ACTACTTCTT TTCATTAAAA TTAAATTTCA      900

ATTATCAATC ATCGTTCAAT TTGATAAAGA TTTAACATTT TTTGTCACAG GGCTAGTAAA      960

AGCAATCTTT ACATAATTCA TCTTTCTTAC ATATATATAT TACCTTTTTC TTCATTAGTA     1020

TTCTATTTGA TTATGATTAT TTTGTCATAA AGCTAGTAAA TTAAACACTC GATATGAGAA     1080

TTATATTACT TCACGCTAAT TAACTCTTAA CACAACAAGA ACTAGTGCAT ATTCAACTTT     1140

CAAAGCATAT ACTATATATT GAGAATATAG ACCACGAAAG TCAATCAAAA GACCTACCAG     1200

CTCTCATCAA GTTCTTTCTT GAAATGATTT TGCAGAATTT CCAACTTAAT TAATTCGACA     1260

TGAATGTGAA AATGTGTGTT GCTCGTTAAG AAAATTGAAT AGAAGTACAA TGAAAATGAT     1320

GAGGAATGGG CAAAACACAA AAGAGTTTCC TTTCGTAACT ACAATTAATT AATGCAAATC     1380

TGAGAAAGGG TTCATGGATA ATGACTACAC ACATGATTAG TCATTCCCCG TGGGCTCTCT     1440

GCTTTCATTT ACTTTATTAG TTTCATCTTC TCTAATTATA TTGTCGCATA TATGATGCAG     1500

TTCTTTTGTC TAAATTACGT AATATGATGT AATTAATTAT CAAATAAAT ATTCAAATTG      1560

CCGTTGGACT AACCTAATGT CCAAGATTAA GACTTGAACA TAAGAATTTT GGAAAAACTA     1620

AACCAGTTAT AATATATACT CTTAAATTGC CATTTCTGAA CACAACCAAA TAATAATATA     1680

TACTATTTAC AGTTTTTTTT AATTGGCAAG AACACTGAAA TCTTATTCAT TGTCTCGCTT     1740

GGTAGTTGAC AAGTTATAAC ACTCATATTC ATATAACCCC ATTCTAACGT TGACGACGAA     1800

CACTCATATA AACCACCCAA ATTCTTAGCA TATTAGCTAA ATATTGGTTT AATTGGAAAT     1860

ATTTTTTTTA TATATAAAAT GCCAGGTAAA TATTAACGAC ATGCAATGTA TATAGGAGTA     1920

GGGCAATAAA AAGAAAAGGA GAATAAAAAG GGATTACCAA AAAAGGAAAG TTTCCAAAAG     1980

GTGATTCTGA TGAGAAACAG AGCCCATACC TCTCTTTTTT CCTCTAAACA TGAAAGAAAA     2040

ATTGGATGGT CCTCCTTCAA TGCTCTCTCC CCACCCAATC CAAACCCAAC TGTCTTCTTT     2100

CTTTCTTTTT TCTTCTTTCT AATTTGATAT TTTCTACCAC TTAATTCCAA TCAATTTCAA     2160

ATTTCAATCT AAATGTATGC ATATAGAATT TAATTAAAAG AATTAGGTGT GTGATATTTG     2220

AGAAAATGTT AGAAGTAATG GTCCATGTTC TTTCTTTCTT TTTCCTTCTA TAACACTTCA     2280

GTTTGAAAAA AAACTACCAA ACCTTCTGTT TTCTGCAAAT GGGTTTTTAA ATACTTCCAA     2340

AGAAATATTC CTCTAAAAGA AATTATAAAC CAAAACAGAA ACCAAAAACA AAAAATAAAG     2400

TTGAAGCAGC AGTTAAGTGG TACTGAGATA ATAAGAATAG TATCTTTAGG CCAATGAACA     2460

AATTAACTCT CTCATAATTC ATCTTCCCAT CCTCACTTCT CTTTCTTTCT GATATAATTA     2520
```

```
ATCTTGCTAA GCCAGGTATG GTTATTGATG ATTTACACTT TTTTTTAAAA GTTTCTTCCT    2580

TTTCTCCAAT CAAATTCTTC AGTTAATCCT TATAAACCAT TTCTTTAATC CAAGGTGTTT    2640

GAGTGCAAAA GGATTTGATC TATTTCTCTT GTGTTTATAC TTCAGCTAGG GCTTATAGAA    2700

ATGGAGGGTG GTGCGAGTAA TGAAGTAGCA GAGAGCAGCA AGAAGATAGG GAGAGGGAAG    2760

ATAGAGATAA AGAGGATAGA GAACACTACG AATCGTCAAG TCACTTTCTG CAAACGACGC    2820

AATGGTTTAC TCAAGAAAGC TTATGAGCTC TCTGTCTTGT GTGACGCTGA GGTTGCTCTT    2880

GTCATCTTCT CCACTCGAGG CCGTCTCTAC GAGTACGCCA ACAACAGGTA CACATCTTTT    2940

AGCTAGATCT TGATTTTGTT GAATTTTTTT TCTAGAATAA AGTTTCGACT CTTCTGGTGG    3000

GTTTTTCAAT CTTTATGGTC TCTTTATAGT TTTTTTCCTT AGTTTCTCTG AAGCTCAAAT    3060

CTCTTTAAAA ATCCCCAAAA TTAGGGTTTG TTTAAAACTA GGGAACCCTA CTTTAACTTC    3120

TTTCTCTTAG TAAAAAAGCA GTGAGGGTCT TCTCTGATCA TTAATTAGCA TCCCCCATAC    3180

CTTGTTCCAG TCACTTTTTC TCCACAAATC CTTATAACAG TATCTATATA TGTATCTATT    3240

TATGTCAGTT TGTACAAGAC ACTTCGATCA ATTTGATGAC CCATCAAGTT TTATTTCTGC    3300

AGATTGATCA TTAGGTTTCC ATCATAGTAA TGAAAAGTA GGGTTCTTGA TAAAATTATA    3360

ATAATATATA TTATTTGGCT ATATAAAAAA GCTATGTAGA TTCCTTAAAA ATTGATTCAC    3420

TAGGGAGAGA CTAGTAGGTG TTTGTCTTCT GACACTTCTC TAATCTTTTG GTGAATCCTT    3480

TTGTTAAATC AAGAAAATGA ATCAGGGACA AGCTTATTG TTGAGTCACT TAATTAATCA    3540

TCCGATCCAT CAATCAAGAA AATAACGAA ACAGAAAATT TTGATTTTTG ATTGTTATTT    3600

TCTCCACTTC AAGTTGGGGA CTTGTCATTT CCGTTTTTCT ATACGTTTCC AGCTATTAAC    3660

AGCTCATGTT CATTTCACCA TTTTGATTAT TTGTCTGCTT TTTAAAGATA AATGTTTTCA    3720

AAAATATTGT TTTTTATTTGC TTGGCTAGTT AATACTATAA TTGAGGTTGA TGTATGACTA    3780

TAATCTATAA GTCAAGTCTC ATATCATGGA TCTAAGTTAA AACTAGTAAA TTTGTAGTTT    3840

CAATGTGAAC TTTCACAACG ACTAAAGAAC TGATCTGAAG TTTATAATGG ACATGACTAA    3900

TTTGATTAAC AAAAGAGGAA TGCATTATGT ATGTAGAAAC ATGTGATATA TATATGTTTC    3960

TATTATCAAA AGTGTAGTTA ACTTTCTTAT TTCAAACACC CTCATGCTTT AGTAGTATCT    4020

TACTTTTGAC ATTTCTCAAC TTCAGCTTTC CATTATACAA CAGCACAATG TAAATTACTT    4080

GTATATGAAT ATGAAAGCAT AACGTTATGC AAAGATTTCT AGCTTTTCTT TTTCTGTTTT    4140

GCAAAAGATT TACAAATATC ATGTTCTTGG TAAAAACATA CTTGCCTCAG CCACATATGC    4200

ATGTAAATGT AATGTTCAAA TATTAATTCA GGAAAAACAA AGAAGAAGCA AAATTAGCTT    4260

CTAGAGTAGG GAATCTATTG ACTTGACCTG AAAATCACTT CTTTTTCTTA AAGCCTAGTA    4320

GTGAATTTTT TAATCTAATT AGGCCAAAAT ATATACTAGC CTAAAATATA ATTTGGATTT    4380

TGTGTCGTAC ATAAATTGGG ACCAATTCCA ATTAACTAAG AGCATATGCA ATTCAAATTC    4440

TTTTTATTTT CTTCTCCGAT TTGCTACTTC TTTCTTTTGT ATGTTTTCAA ATTAGGATTA    4500

CACTTTTTTG GGGAAGTACA CATTAGGGTC TTCTCGAACT TTGATTATAC ATATATATAT    4560

ATATATATAT ATATAACTTT GTGAGATGTC ACTGTTAATA GATAATAGGC AATAACAATA    4620

ATATCCAAAA AAGAAGGCGC AAACAAATCA TATACTATAT GGTACTGGTC CATTCACTAT    4680

TTTGTCGGTT GAATTTAAGG TTTGGCGTAC AAACTTTGTT TCAAACCTTT ATTATTCCGT    4740

CTTTCTGTGT GTTTTGTATA TCCAGAAGAT AAAAATATCA ATTTCTTTAA CGACTTCATA    4800

TATATATATA TATATATATA TATATATATT TTTCTCTTCT GGTTTTAGTG TTTGAATCCA    4860
```

```
ACAGTTATAG TTTCGTGTGT CTTTGTTTTA CTTGTGGTGG TTTAAGTTTG AGATTTTCAC      4920

CGATTGCATC TATTTACATA TATAGCTACC ACAAAAAAGA TTGCATTTTA AAATCTTTTC      4980

CTTTGTGTGA ATGTTGATGA AGTGTGAGAG GAACAATAGA AAGGTACAAG AAAGCTTGCT      5040

CCGACGCCGT TAACCCTCCG ACCATCACCG AAGCTAATAC TCAGGTTAGC TTTTAATTAA      5100

TACACCTAGC TAGCTAGTTC GTTAATTACT TAATTTCTTC TTCTTTTAGT TATCTGACCT      5160

TTTTTTCACC TCTTGTAACA ATGATGGGAT CGAAATTGAT GAAGTACTAT CAGCAAGAGG      5220

CGTCTAAACT CCGGAGACAG ATTCGGGACA TTCAGAATTT GAACAGACAC ATTCTTGGTG      5280

AATCTCTTGG TTCCTTGAAC TTTAAGGAAC TCAAGAACCT TGAAAGTAGG CTTGAGAAAG      5340

GAATCAGTCG TGTCCGATCC AAGAAGGTAC ATCACTAACT CTCCATCAAT CTCCTTATCA      5400

TTGAATATAT ATCCATCTGA TTCTTGCCCG TTATATTTGG TTTTTCTCTC CAGCACGAGA      5460

TGTTAGTTGC AGAGATTGAA TACATGCAAA AAAGGGTAAA AGTAAAACCT ATCTTCCTTC      5520

ACAATGAACT ACCCCTACTT TATTAGCAAC TTCTCTTTCT GATGATCATC TTTTTTATTT      5580

TCTGTTGTCG CTTGCATTGT AGGAAATCGA GCTGCAAAAC GATAACATGT ATCTCCGCTC      5640

CAAGGTTTTA TACATAACTC TTTTTGGCAT TTTTGATCAT CATTTTTTTC CGGTAGACAA      5700

TCTCTTGATG TGCAAATTCT AAATATCTCT GCAGATTACT GAAAGAACAG GTCTACAGCA      5760

ACAAGAATCG AGTGTGATAC ATCAAGGGAC AGTTTACGAG TCGGGTGTTA CTTCTTCTCA      5820

CCAGTCGGGG CAGTATAACC GGAATTATAT TGCGGTTAAC CTTCTTGAAC CGAATCAGAA      5880

TTCCTCCAAC CAAGACCAAC CACCTCTGCA ACTTGTTTGA TTCAGTCTAA CATAAGCTTC      5940

TTTCCTCAGC CTGAGATCGA TCTATAGTGT CACCTAAATG CGGCCGCGTC CCTCAACATC      6000

TAGTCGCAAG CTGAGGGGAA CCACTAGTGT CATACGAACC TCCAAGAGAC GGTTACACAA      6060

ACGGGTACAT TGTTGATGTC ATGTATGACA ATCGCCCAAG TAAGTATCCA GCTGTGTTCA      6120

GAACGTACGT CCGAATTC                                                  6138
```

(2) INFORMATION FOR SEQ ID NO:5:

(i) SEQUENCE CHARACTERISTICS:
        (A) LENGTH: 896 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 7..753

(ix) FEATURE:
        (A) NAME/KEY: misc_feature
        (B) LOCATION: 896
        (D) OTHER INFORMATION: /note= "There is a poly(A) tail at
            the end of the cDNA sequence."

(ix) FEATURE:
        (A) NAME/KEY: misc_feature
        (B) LOCATION: 1..896
        (D) OTHER INFORMATION: /note= "AGL1 cDNA and deduced
            protein sequences."

(xi) SEQUENCE DESCRIPTION: SEQ ID NO:5:

```
GGATCA ATG GAG GAA GGT GGG AGT AGT CAC GAC GCA GAG AGT AGC AAG         48
       Met Glu Glu Gly Gly Ser Ser His Asp Ala Glu Ser Ser Lys
        1               5                  10

AAA CTA GGG AGA GGG AAA ATA GAG ATA AAG AGG ATA GAG AAC ACA ACA         96
Lys Leu Gly Arg Gly Lys Ile Glu Ile Lys Arg Ile Glu Asn Thr Thr
```

```
                15                      20                      25                      30

AAT CGT CAA GTT ACT TTC TGC AAA CGA CGC AAT GGT CTT CTC AAG AAA          144
Asn Arg Gln Val Thr Phe Cys Lys Arg Arg Asn Gly Leu Leu Lys Lys
                        35                      40                      45

GCT TAT GAA CTC TCT GTC TTG TGT GAT GCC GAA GTT GCC CTC GTC ATC          192
Ala Tyr Glu Leu Ser Val Leu Cys Asp Ala Glu Val Ala Leu Val Ile
                50                      55                      60

TTC TCC ACT CGT GGC CGT CTC TAT GAG TAC GCC AAC AAC AGT GTG AGG          240
Phe Ser Thr Arg Gly Arg Leu Tyr Glu Tyr Ala Asn Asn Ser Val Arg
            65                      70                      75

GGT ACA ATT GAA AGG TAC AAG AAA GCT TGT TCC GAT GCC GTC AAC CCT          288
Gly Thr Ile Glu Arg Tyr Lys Lys Ala Cys Ser Asp Ala Val Asn Pro
        80                      85                      90

CCT TCC GTC ACC GAA GCT AAT ACT CAG TAC TAT CAG CAA GAA GCC TCT          336
Pro Ser Val Thr Glu Ala Asn Thr Gln Tyr Tyr Gln Gln Glu Ala Ser
95                      100                     105                     110

AAG CTT CGG AGG CAG ATT CGA GAT ATT CAG AAT TCA AAT AGG CAT ATT          384
Lys Leu Arg Arg Gln Ile Arg Asp Ile Gln Asn Ser Asn Arg His Ile
                    115                     120                     125

GTT GGG GAA TCA CTT GGT TCC TTG AAC TTC AAG GAA CTC AAA AAC CTA          432
Val Gly Glu Ser Leu Gly Ser Leu Asn Phe Lys Glu Leu Lys Asn Leu
                130                     135                     140

GAA GGA CGT CTT GAA AAA GGA ATC AGC CGT GTC CGC TCC AAA AAG AAT          480
Glu Gly Arg Leu Glu Lys Gly Ile Ser Arg Val Arg Ser Lys Lys Asn
            145                     150                     155

GAG CTG TTA GTG GCA GAG ATA GAG TAT ATG CAG AAG AGG GAA ATG GAG          528
Glu Leu Leu Val Ala Glu Ile Glu Tyr Met Gln Lys Arg Glu Met Glu
        160                     165                     170

TTG CAA CAC AAT AAC ATG TAC CTG CGA GCA AAG ATA GCC GAA GGC GCC          576
Leu Gln His Asn Asn Met Tyr Leu Arg Ala Lys Ile Ala Glu Gly Ala
175                     180                     185                     190

AGA TTG AAT CCG GAC CAG CAG GAA TCG AGT GTG ATA CAA GGG ACG ACA          624
Arg Leu Asn Pro Asp Gln Gln Glu Ser Ser Val Ile Gln Gly Thr Thr
                    195                     200                     205

GTT TAC GAA TCC GGT GTA TCT TCT CAT GAC CAG TCG CAG CAT TAT AAT          672
Val Tyr Glu Ser Gly Val Ser Ser His Asp Gln Ser Gln His Tyr Asn
                210                     215                     220

CGG AAC TAT ATT CCG GTG AAC CTT CTT GAA CCG AAT CAG CAA TTC TCC          720
Arg Asn Tyr Ile Pro Val Asn Leu Leu Glu Pro Asn Gln Gln Phe Ser
            225                     230                     235

GGC CAA GAC CAA CCT CCT CTT CAA CTT GTG TAACTCAAAA CATGATAACT            770
Gly Gln Asp Gln Pro Pro Leu Gln Leu Val
        240                     245

TGTTTCTTCC CCTCATAACG ATTAAGAGAG AGACGAGAGA GTTCATTTTA TATTTATAAC        830

GCGACTGTGT ATTCATAGTT TAGGTTCTAA TAATGATAAT AACAAAACTG TTGTTTCTTT        890

GCTTCA                                                                   896

(2) INFORMATION FOR SEQ ID NO:6:

(i) SEQUENCE CHARACTERISTICS:
        (A) LENGTH: 248 amino acids
        (B) TYPE: amino acid
        (D) TOPOLOGY: linear (ii) MOLECULE TYPE: protein (xi) SEQUENCE DESCRIPTION: SEQ ID NO:6:

Met Glu Glu Gly Gly Ser Ser His Asp Ala Glu Ser Ser Lys Lys Leu
1               5                   10                  15
```

```
Gly Arg Gly Lys Ile Glu Ile Lys Arg Ile Glu Asn Thr Thr Asn Arg
             20                  25                  30

Gln Val Thr Phe Cys Lys Arg Arg Asn Gly Leu Leu Lys Lys Ala Tyr
         35                  40                  45

Glu Leu Ser Val Leu Cys Asp Ala Glu Val Ala Leu Val Ile Phe Ser
     50                  55                  60

Thr Arg Gly Arg Leu Tyr Glu Tyr Ala Asn Asn Ser Val Arg Gly Thr
 65                  70                  75                  80

Ile Glu Arg Tyr Lys Lys Ala Cys Ser Asp Ala Val Asn Pro Pro Ser
                 85                  90                  95

Val Thr Glu Ala Asn Thr Gln Tyr Tyr Gln Gln Glu Ala Ser Lys Leu
            100                 105                 110

Arg Arg Gln Ile Arg Asp Ile Gln Asn Ser Asn Arg His Ile Val Gly
        115                 120                 125

Glu Ser Leu Gly Ser Leu Asn Phe Lys Glu Leu Lys Asn Leu Glu Gly
    130                 135                 140

Arg Leu Glu Lys Gly Ile Ser Arg Val Arg Ser Lys Lys Asn Glu Leu
145                 150                 155                 160

Leu Val Ala Glu Ile Glu Tyr Met Gln Lys Arg Glu Met Glu Leu Gln
                165                 170                 175

His Asn Asn Met Tyr Leu Arg Ala Lys Ile Ala Glu Gly Ala Arg Leu
            180                 185                 190

Asn Pro Asp Gln Gln Glu Ser Ser Val Ile Gln Gly Thr Thr Val Tyr
        195                 200                 205

Glu Ser Gly Val Ser Ser His Asp Gln Ser Gln His Tyr Asn Arg Asn
    210                 215                 220

Tyr Ile Pro Val Asn Leu Leu Glu Pro Asn Gln Gln Phe Ser Gly Gln
225                 230                 235                 240

Asp Gln Pro Pro Leu Gln Leu Val
                245

(2) INFORMATION FOR SEQ ID NO:7:

(i) SEQUENCE CHARACTERISTICS:
        (A) LENGTH: 959 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 78..818

(ix) FEATURE:
        (A) NAME/KEY: misc_feature
        (B) LOCATION: 1..959
        (D) OTHER INFORMATION: /note= "AGL5 cDNA and deduced
            protein sequences."

(xi) SEQUENCE DESCRIPTION: SEQ ID NO:7:

GAATTCATCT TCCCATCCTC ACTTCTCTTT CTTTCTGATC ATAATTAATC TTGCTAAGCC        60

AGCTAGGGCT TATAGAA ATG GAG GGT GGT GCG AGT AAT GAA GTA GCA GAG          110
                   Met Glu Gly Gly Ala Ser Asn Glu Val Ala Glu
                    1               5                  10

AGC AGC AAG AAG ATA GGG AGA GGG AAG ATA GAG ATA AAG AGG ATA GAG        158
Ser Ser Lys Lys Ile Gly Arg Gly Lys Ile Glu Ile Lys Arg Ile Glu
            15                  20                  25

AAC ACT ACG AAT CGT CAA GTC ACT TTC TGC AAA CGA CGC AAT GGT TTA        206
```

```
Asn Thr Thr Asn Arg Gln Val Thr Phe Cys Lys Arg Arg Asn Gly Leu
            30                  35                  40

CTC AAG AAA GCT TAT GAG CTC TCT GTC TTG TGT GAC GCT GAG GTT GCT    254
Leu Lys Lys Ala Tyr Glu Leu Ser Val Leu Cys Asp Ala Glu Val Ala
        45                  50                  55

CTT GTC ATC TTC TCC ACT CGA GGC CGT CTC TAC GAG TAC GCC AAC AAC    302
Leu Val Ile Phe Ser Thr Arg Gly Arg Leu Tyr Glu Tyr Ala Asn Asn
60                  65                  70                  75

AGT GTG AGA GGA ACA ATA GAA AGG TAC AAG AAA GCT TGC TCC GAC GCC    350
Ser Val Arg Gly Thr Ile Glu Arg Tyr Lys Lys Ala Cys Ser Asp Ala
                80                  85                  90

GTT AAC CCT CCG ACC ATC ACC GAA GCT AAT ACT CAG TAC TAT CAG CAA    398
Val Asn Pro Pro Thr Ile Thr Glu Ala Asn Thr Gln Tyr Tyr Gln Gln
            95                  100                 105

GAG GCG TCT AAA CTC CGG AGA CAG ATT CGG GAC ATT CAG AAT TTG AAC    446
Glu Ala Ser Lys Leu Arg Arg Gln Ile Arg Asp Ile Gln Asn Leu Asn
        110                 115                 120

AGA CAC ATT CTT GGT GAA TCT CTT GGT TCC TTG AAC TTT AAG GAA CTC    494
Arg His Ile Leu Gly Glu Ser Leu Gly Ser Leu Asn Phe Lys Glu Leu
    125                 130                 135

AAG AAC CTT GAA AGT AGG CTT GAG AAA GGA ATC AGT CGT GTC CGA TCC    542
Lys Asn Leu Glu Ser Arg Leu Glu Lys Gly Ile Ser Arg Val Arg Ser
140                 145                 150                 155

AAG AAG CAC GAG ATG TTA GTT GCA GAG ATT GAA TAC ATG CAA AAA AGG    590
Lys Lys His Glu Met Leu Val Ala Glu Ile Glu Tyr Met Gln Lys Arg
                160                 165                 170

GAA ATC GAG CTG CAA AAC GAT AAC ATG TAT CTC CGC TCC AAG ATT ACT    638
Glu Ile Glu Leu Gln Asn Asp Asn Met Tyr Leu Arg Ser Lys Ile Thr
            175                 180                 185

GAA AGA ACA GGT CTA CAG CAA CAA GAA TCG AGT GTG ATA CAT CAA GGG    686
Glu Arg Thr Gly Leu Gln Gln Gln Glu Ser Ser Val Ile His Gln Gly
        190                 195                 200

ACA GTT TAC GAG TCG GGT GTT ACT TCT TCT CAC CAG TCG GGG CAG TAT    734
Thr Val Tyr Glu Ser Gly Val Thr Ser Ser His Gln Ser Gly Gln Tyr
    205                 210                 215

AAC CGG AAT TAT ATT GCG GTT AAC CTT CTT GAA CCG AAT CAG AAT TCC    782
Asn Arg Asn Tyr Ile Ala Val Asn Leu Leu Glu Pro Asn Gln Asn Ser
220                 225                 230                 235

TCC AAC CAA GAC CAA CCA CCT CTG CAA CTT GTT TGATTCAGTC TAACATAAGC  835
Ser Asn Gln Asp Gln Pro Pro Leu Gln Leu Val
                240                 245

TTCTTTCCTC AGCCTGAGAT CGATCTATAG TGTCACCTAA ATGCGGCCGC GTCCCTCAAC  895

ATCTAGTCGC AAGCTGAGGG GAACCACTAG TGTCATACGA ACCTCCAAGA GACGGTTACA  955

CAAA                                                               959

(2) INFORMATION FOR SEQ ID NO:8:

(i) SEQUENCE CHARACTERISTICS:
        (A) LENGTH: 246 amino acids
        (B) TYPE: amino acid
        (D) TOPOLOGY: linear (ii) MOLECULE TYPE: protein (xi) SEQUENCE DESCRIPTION: SEQ ID NO:8:

Met Glu Gly Gly Ala Ser Asn Glu Val Ala Glu Ser Ser Lys Lys Ile
1               5                   10                  15

Gly Arg Gly Lys Ile Glu Ile Lys Arg Ile Glu Asn Thr Thr Asn Arg
            20                  25                  30
```

```
Gln Val Thr Phe Cys Lys Arg Arg Asn Gly Leu Leu Lys Lys Ala Tyr
                35                  40                  45

Glu Leu Ser Val Leu Cys Asp Ala Glu Val Ala Leu Val Ile Phe Ser
     50                  55                  60

Thr Arg Gly Arg Leu Tyr Glu Tyr Ala Asn Asn Ser Val Arg Gly Thr
 65                  70                  75                  80

Ile Glu Arg Tyr Lys Lys Ala Cys Ser Asp Ala Val Asn Pro Pro Thr
                 85                  90                  95

Ile Thr Glu Ala Asn Thr Gln Tyr Tyr Gln Gln Glu Ala Ser Lys Leu
            100                 105                 110

Arg Arg Gln Ile Arg Asp Ile Gln Asn Leu Asn Arg His Ile Leu Gly
            115                 120                 125

Glu Ser Leu Gly Ser Leu Asn Phe Lys Glu Leu Lys Asn Leu Glu Ser
            130                 135                 140

Arg Leu Glu Lys Gly Ile Ser Arg Val Arg Ser Lys Lys His Glu Met
145                 150                 155                 160

Leu Val Ala Glu Ile Glu Tyr Met Gln Lys Arg Glu Ile Glu Leu Gln
                165                 170                 175

Asn Asp Asn Met Tyr Leu Arg Ser Lys Ile Thr Glu Arg Thr Gly Leu
            180                 185                 190

Gln Gln Gln Glu Ser Ser Val Ile His Gln Gly Thr Val Tyr Glu Ser
            195                 200                 205

Gly Val Thr Ser Ser His Gln Ser Gly Gln Tyr Asn Arg Asn Tyr Ile
210                 215                 220

Ala Val Asn Leu Leu Glu Pro Asn Gln Asn Ser Ser Asn Gln Asp Gln
225                 230                 235                 240

Pro Pro Leu Gln Leu Val
            245
```

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..27
        (D) OTHER INFORMATION: /note= "Primer AGL8 5-4"

(xi) SEQUENCE DESCRIPTION: SEQ ID NO:9:

CCGTCGACGA TGGGAAGAGG TAGGGTT                                     27

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..20
        (D) OTHER INFORMATION: /note= "Primer OAM14."

(xi) SEQUENCE DESCRIPTION: SEQ ID NO:10:

AATCATTACC AAGATATGAA                                              20

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:11:

CGGATAGCTC GAATATCG                                            18

(2) INFORMATION FOR SEQ ID NO:12:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:12:

AACATTGCGT CGTTTGC                                            17

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:13:

GTAATTACCA GGCAAGGACT CTCC                                  24

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:14:

GTCATCGGCG GGGGTCATAA CGTG                                  24

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:15:

GAGGATAGAG AACACTACGA ATCG                                  24

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:16:

CAGGTCAAGT CAATAGATTC                                      20

(2) INFORMATION FOR SEQ ID NO:17:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:17:

CAGAATTTAG TGAATAATAT TG                                                     22

(2) INFORMATION FOR SEQ ID NO:18:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:18:

GCCAGAGATA ATGCTATTCC                                                        20

(2) INFORMATION FOR SEQ ID NO:19:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:19:

CATTGATCCA TATATGACAT CAC                                                    23

(2) INFORMATION FOR SEQ ID NO:20:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (xi) SEQUENCE DESCRIPTION: SEQ ID NO:20:

GTGATGTCAT ATATGGATCA ATGGGAAGAG GTAGGGTTCA G                                 41

(2) INFORMATION FOR SEQ ID NO:21:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:21:

CAAGAGTCGG TGGAATATTC G                                                      21

(2) INFORMATION FOR SEQ ID NO:22:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (xi) SEQUENCE DESCRIPTION: SEQ ID NO:22:

CGAATATTCC ACCGACTCTT GGTACGCTTC TCCTACTCTA T                                 41

(2) INFORMATION FOR SEQ ID NO:23:

```
    (i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:23:

CTAATAAGTA AGATCGCGGA A                                           21

(2) INFORMATION FOR SEQ ID NO:24:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:24:

TTCCGCGATC TTACTTATTA GCATGGAGAG GATACTTGAA C                     41
```

SEED PLANTS CHARACTERIZED BY DELAYED SEED DISPERSAL

This application is a divisional of U.S. patent application Ser. No. 09/067,800 (now U.S. Pat. No. 6,198,024) filed Apr. 28, 1998, which claims the benefit of priority of United States Provisional Application Ser. No. 60/051,030 (now abandoned) filed Jun. 27, 1997, the entire contents of which is incorporated herein.

This invention was made with government support under DCB9018749 awarded by the National Science Foundation. The government has certain rights in the invention.

BACKGROUND OF THE INVENTION

1. FIELD OF THE INVENTION

The present invention relates generally to plant molecular biology and genetic engineering and more specifically to the production of genetically modified seed plants in which the natural process of dehiscence is delayed.

2. BACKGROUND INFORMATION

Rapeseed is one of the most important oilseed crops after soybeans and cottonseed, representing 10% of the world oilseed production in 1990. Rapeseed contains 40% oil, which is pressed from the seed, leaving a high-protein seed meal of value for animal feed and nitrogen fertilizer. Rapeseed oil, also known as canola oil, is a valuable product, representing the fourth most commonly traded vegetable oil in the world.

The production of oilseeds, meal and oil from rapeseed plants has been increasing continuously for the last 30 years for food and feed grains, mainly by expansion of the area under cultivation. Most northern European countries produce rapeseed as their main edible oil crop. By the year 2000, China is expected to be the leading producer with 9.2 metric tons (Mt; 26%); followed by India with 7.8 Mt (22%); the European Community (12 countries), with 7.6 Mt (21%); Canada, 3.8 Mt (11%) and eastern Europe with 2.6 Mt (7%).

Unfortunately, the yield of seed from rapeseed and related plants is limited by pod dehiscence, which is a process that occurs late in fruit development whereby the pod is opened and the enclosed seeds released. Degradation and separation of cell walls along a discrete layer of cells dividing the two halves of the pod, termed the "dehiscence zone," result in separation of the two halves of the pod and release of the contained seeds. Seed "shattering," whereby seeds are prematurely shed through dehiscence before the crop can be harvested, is a significant problem faced by commercial seed producers and represents a loss of income to the industry. Adverse weather conditions can exacerbate the process of dehiscence, resulting in greater than 50% loss of seed yield.

Attempts to solve this problem over the past 20 years have focused on the breeding of shatter-resistant varieties. However, these plant hybrids are frequently sterile and lose favorable characteristics that must be regained by backcrossing, which is both time-consuming and laborious. Other strategies to alleviate pod shattering include the use of chemicals such as pod sealants or mechanical techniques such as swathing to reduce wind-stimulated shattering. To date, however, a simple method for producing genetically modified seed plants that do not open and release their seeds prematurely has not been described.

Thus, a need exists for identifying genes that regulate the dehiscence process and for developing genetically modified seed plant varieties in which the natural seed dispersal process is delayed. The present invention satisfies this need and provides related advantages as well.

SUMMARY OF THE INVENTION

The present invention provides a non-naturally occurring seed plant that is characterized by delayed seed dispersal due to ectopic expression of a nucleic acid molecule encoding an AGL8-like gene product. The AGL8-like gene product can have, for example, substantially the amino acid sequence of an AGL8 ortholog such as Arabidopsis AGL8 (SEQ ID NO:2). Particularly useful seed plants of the invention, which are characterized by delayed seed dispersal, include members of the Brassicaceae, such as rapeseed, and members of the Fabaceae, such as soybeans, peas, lentils and beans.

In one embodiment, the invention provides a transgenic seed plant that is characterized by delayed seed dispersal due to ectopic expression of a nucleic acid molecule encoding an AGL8-like gene product. In a transgenic seed plant of the invention, the nucleic acid molecule encoding the AGL8-like gene product can be operatively linked to an exogenous regulatory element. Useful exogenous regulatory elements include constitutive regulatory elements and dehiscence zone-selective regulatory elements. In particular, the exogenous regulatory element can be a dehiscence zone-selective regulatory element that is an AGL1 regulatory element or an AGL5 regulatory element.

In another embodiment, the invention provides a non-naturally occurring seed plant that is characterized by delayed seed dispersal due to suppression of both AGL1 and AGL5 expression in the seed plant. Such a non-naturally occurring seed plant characterized by delayed seed dispersal can be, for example, an agl1 agl5 double mutant.

The present invention further provides a tissue derived from a non-naturally occurring seed plant of the invention. In one embodiment, the invention provides a tissue derived from a non-naturally occurring seed plant that has an ectopically expressed nucleic acid molecule encoding an AGL8-like gene product and is characterized by delayed seed dispersal. In another embodiment, the invention provides a tissue derived from a non-naturally occurring seed plant in which AGL1 expression and AGL5 expression each are suppressed, where the seed plant is characterized by delayed seed dispersal.

Methods of producing a non-naturally occurring seed plant characterized by delayed seed dispersal also are provided herein. Such methods entail ectopically expressing a nucleic acid molecule encoding an AGL8-like gene product in the seed plant, whereby seed dispersal is delayed due to ectopic expression of the nucleic acid molecule.

The invention also provides a substantially purified dehiscence zone-selective regulatory element, comprising a nucleotide sequence that confers selective expression upon an operatively linked nucleic acid molecule in the valve margin or dehiscence zone of a seed plant, provided that the dehiscence zone-selective regulatory element does not have a nucleotide sequence consisting of nucleotides 1889 to 2703 of SEQ ID NO:4. The dehiscence zone-selective regulatory element can be, for example, an AGL1 regulatory element or AGL5 regulatory element.

Further provided is a plant expression vector containing a dehiscence zone-selective regulatory element that confers selective expression upon an operatively linked nucleic acid molecule in the valve margin or dehiscence zone of a seed plant, provided that the dehiscence zone-selective regulatory element does not have a nucleotide sequence consisting of nucleotides 1889 to 2703 of SEQ ID NO:4. If desired, a plant expression vector can contain a nucleic acid molecule encoding an AGL8-like gene product in addition to the dehiscence zone-selective regulatory element.

The invention also provides a kit for producing a transgenic seed plant characterized by delayed seed dispersal, such kit containing a dehiscence zone-selective regulatory element that confers selective expression upon an operatively linked nucleic acid molecule in the valve margin or dehiscence zone of a seed plant, provided that said dehiscence zone-selective regulatory element does not have a nucleotide sequence consisting of nucleotides 1889 to 2703 of SEQ ID NO:4. In a kit of the invention, the dehiscence zone-selective regulatory element can be, if desired, operatively linked to a nucleic acid molecule encoding an AGL8-like gene product.

BRIEF DESCRIPTION OF THE DRAWINGS

FIG. 3 shows scanning electron micrographs of wild type Arabidopsis and a representative 35S::AGL8 transgenic line. The dehiscence zone is evident in the wild type plant. In contrast, in the 35S::AGL8 transgenic line, the cells of the outer replum are converted to a valve cell fate, and the dehiscence zone is absent.

FIG. 4A shows the genomic structure of the AGL5 gene, with the positions of exons indicated by boxes, and the positions of introns indicated by thin lines. The agl5 mutant allele, generated by targeted disruption following homologous recombination, has a kanamycin resistance cassette that is indicated by a yellow hatched box and located within the MADS-box region. FIG. 4B shows the genomic structure of the AGL1 gene, with the position of the approximately 17 kb T-DNA insertion into the large intron of the agl1-1 locus indicated by the arrowhead. Exons are indicated by boxes. Introns are indicated by thin lines. The MADS-box region is shown as a hatched box. FIG. 4C shows that a probe specific for the 3' end of the AGL5 complementary cDNA detected the AGL5 transcript in wild type but not in the agl5 knockout mutant plants. FIG. 4D shows that a probe specific for the 3' end of the AGL1 complementary DNA (cDNA) detected the AGL1 transcript in wild type but not in the agl1 mutant generated by T-DNA insertion.

FIG. 6 shows the nucleotide (SEQ ID NO:1) and amino acid (SEQ ID NO:2) sequence of Arabidopsis AGL8.

FIG. 7 shows the nucleotide sequence of the Arabidopsis AGL1 gene (SEQ ID NO:3). The exons and translation start site are indicated.

FIG. 8 shows the nucleotide sequence of the Arabidopsis AGL5 gene (SEQ ID NO:4). The exons and translation start site are indicated.

DETAILED DESCRIPTION OF THE INVENTION

The present invention provides a non-naturally occurring seed plant that is characterized by delayed seed dispersal due to ectopic expression of a nucleic acid molecule encoding an AGL8-like gene product. The AGL8-like gene product can have, for example, substantially the amino acid sequence of an AGL8 ortholog such as Arabidopsis AGL8 (SEQ ID NO:2).

Figure 1:
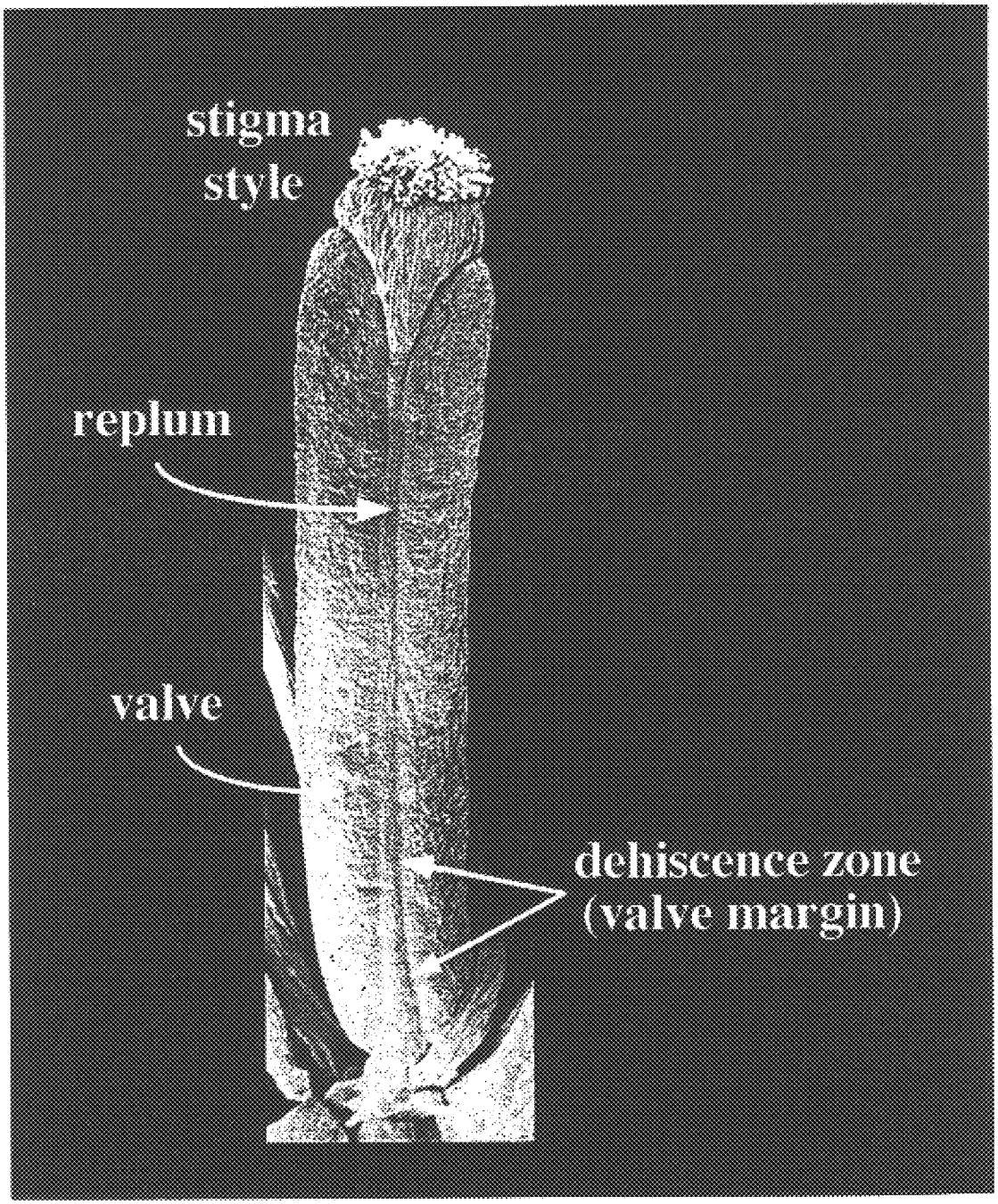
FIG. 1 shows a scanning electron micrograph of an Arabidopsis gynoecium at about the time of pollination. A number of distinct cell types are shown, including the apical stigma, the style, and the ovary. The ovary walls, or valves, which are separated along their entire lengths by a small suture denoted the "replum," are indicated. The dehiscence zone, a narrow band of cells one to three cells wide along the valve/replum boundary, also is indicated.

The fruit, a complex structure unique to flowering plants, mediates the maturation and dispersal of seeds. In most flowering plants, the fruit consists of the pericarp, which is derived from the ovary wall, and the seeds, which develop from fertilized ovules. Arabidopsis, which is typical of the more than 3000 species of the Brassicaceae, produces fruit in which the two carpel valves (ovary walls) are joined to the replum, a visible suture that divides the two carpels. The structure of an *Arabidopsis gynoecium* around the time of pollination, including the carpel valves and replum, is shown in FIG. 1.

Figure 2:
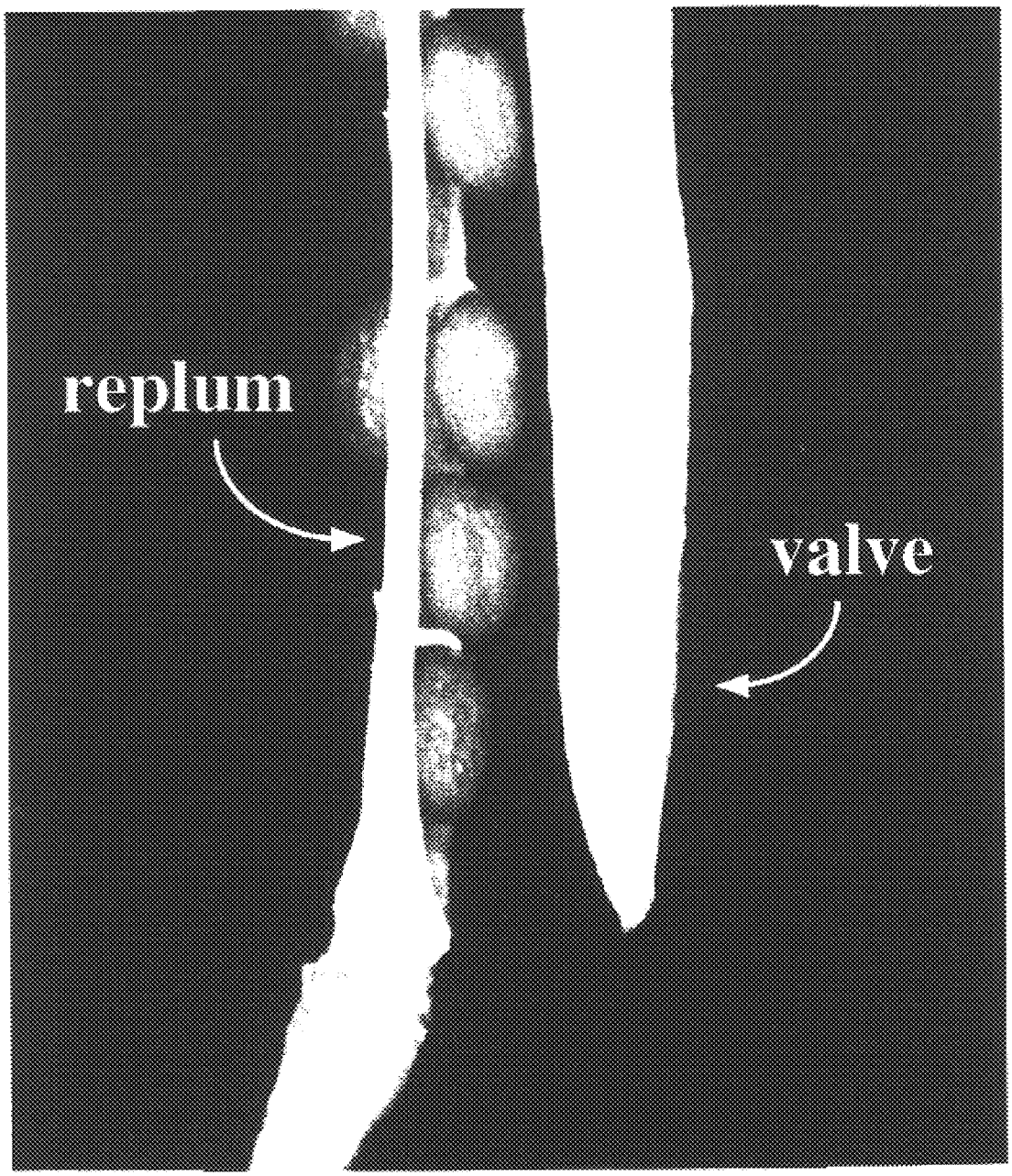
FIG. 2 shows a wild type Arabidopsis fruit immediately following pod shattering. The seeds as well as the replum are clearly visible.
Figure 4:
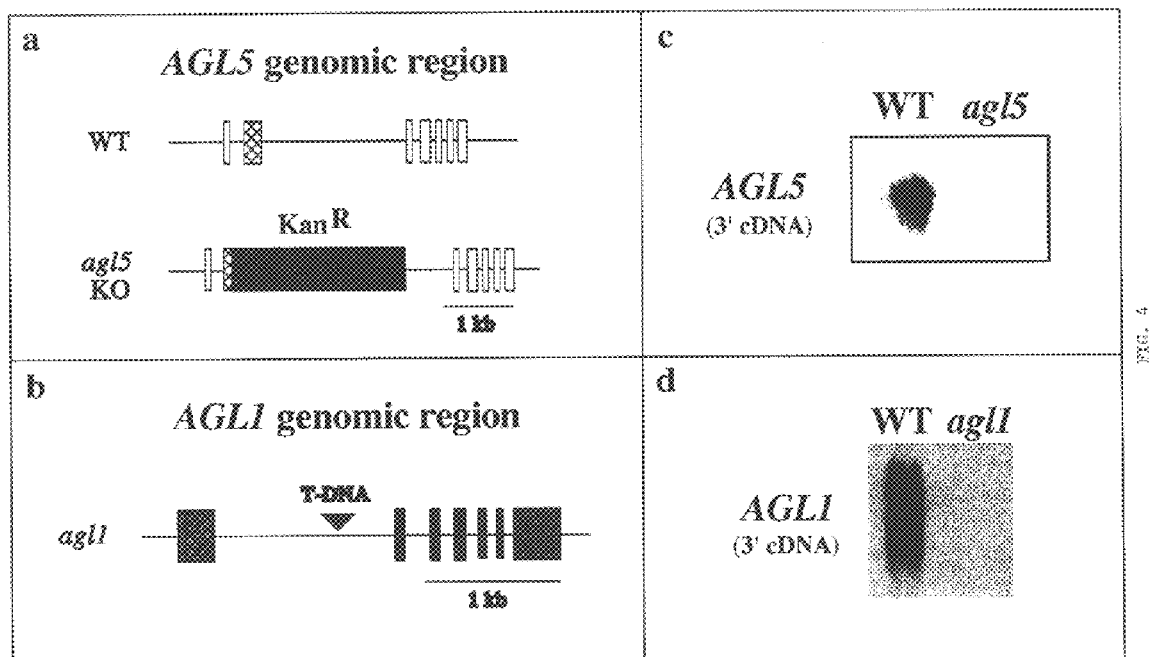
FIG. 4(A–D) shows the agl5 and agl1 genomic regions and the loss of AGL5 or AGL1 expression, respectively, in the agl5 or agl1 mutant.

Pod dehiscence or shatter occurs late in fruit development in a wide spectrum of important plant crops such as oilseed rape (*Brassica napus* L.) and is a process of economic importance that can lead to significant losses in seed yield. In oilseed rape, dehiscence involves the breakdown of cell wall material in a discrete cell layer known as the "dehiscence zone," which is a region of only one to three cells in width that extends along the entire length of the valve/replum boundary (Meakin and Roberts, *J. Exp. Botany* 41:995–1002 (1990)). As the cells in the dehiscence zone separate from one another, the valves detach from the replum, allowing seeds to be dispersed (see FIG. 2).

The plant hormone ethylene is produced by developing seeds and appears to be an important regulator of the dehiscence process. One line of evidence supporting a role for ethylene in regulation of dehiscence comes from studies of fruit ripening, which, like fruit dehiscence, is a process involving the breakdown of cell wall material. In fruit ripening, ethylene acts in part by activating cell wall degrading enzymes such as polygalacturonase (Theologis et al., *Develop. Genetics* 14:282–295 (1993)). Moreover, in genetically modified tomato plants in which the ethylene response is blocked, such as transgenic tomato plants expressing antisense polygalacturonase, there is a significant delay in fruit ripening (Lanahan et al., *The Plant Cell* 6:521–530 (1994); Smith et al., *Nature* 334:724–726 (1988)).

In dehiscence, ultrastructural changes that culminate in degradation of the middle lamella of dehiscence zone cell walls weaken rapeseed pods and eventually lead to pod shatter. As in fruit ripening, hydrolytic enzymes including polygalacturonases play a role in this programmed breakdown. For example, in oilseed rape, a specific endo-polygalacturonase, RDPG1, is upregulated and expressed exclusively in the dehiscence zone late in pod development (Petersen et al., *Plant Mol. Biol.* 31:517–527 (1996), which is incorporated herein by reference). Ethylene may regulate the activity of hydrolytic enzymes involved in the process of dehiscence as it does in fruit ripening (Meakin and Roberts, *J. Exp. Botany* 41:1003–1011 (1990), which is incorporated herein by reference). Yet, until now, the proteins that control the process of dehiscence, such as those regulating the relevant hydrolytic enzymes, have eluded identification.

The present invention is directed to the surprising discovery that the AGL8 transcription factor regulates the process of dehiscence. As disclosed herein, Arabidopsis plants were transformed with an AGL8 cDNA under control of a 35S cauliflower mosaic virus (CaMV) constitutive promoter such that AGL8 was ectopically expressed throughout the transformed plant. In particular, AGL8, which is normally expressed in the carpel valves, was ectopically expressed in the replum, which is a small strip of cells separating the two valves in a mature fruit. As a consequence of such ectopic expression, the replum of the fruit was absent, with the cells of the outer replum replaced by cells having characteristics of valve identity, demonstrating that, in this context, AGL8 expression is sufficient to specify valve cell fate. Furthermore, ectopic expression of the AGL8 cDNA produced a transgenic plant in which the dehiscence zone failed to develop normally, resulting in delayed seed dispersal (see Example I). Whereas wild type Arabidopsis produced fruit that opened and released seeds on or about 14 days after pollination, transformed Arabidopsis ectopically expressing AGL8 produced fruit in which seed dispersal was postponed, or in which the seeds were never released unless the fruit was opened manually (see FIG. 3). Thus, for the first time, seed plants were genetically modified to delay the natural process of dehiscence.

The present invention also relates to the surprising discovery that an agl1 agl5 double mutant seed plant has a delayed seed dispersal phenotype that is strikingly similar to the AGL8 gain-of-function phenotype. As disclosed herein, loss-of-function mutations in the AGL1 and AGL5 genes were produced by disruptive T-DNA insertion and homologous recombination (see Example II). In the resulting agl1 agl5 double mutant plants, the dehiscence zone failed to develop normally, and the mature fruits did not undergo dehiscence (see FIG. 5). Thus, AGL1 or AGL5 gene expression is required for development of the dehiscence zone. These results indicate that AGL1, AGL5 and AGL8 regulate pod dehiscence and that manipulation of AGL1, AGL5 and AGL8 expression can allow the process of pod shatter to be controlled.

Thus, the present invention provides a non-naturally occurring seed plant that is characterized by delayed seed dispersal due to ectopic expression of a nucleic acid molecule encoding an AGL8-like gene product. The AGL8-like gene product can have, for example, substantially the amino acid sequence of an AGL8 ortholog such Arabidopsis AGL8 (SEQ ID NO:2).

As used herein, the term "non-naturally occurring," when used in reference to a seed plant, means a seed plant that has been genetically modified by man. A transgenic seed plant of the invention, for example, is a non-naturally occurring seed plant that contains an exogenous nucleic acid molecule encoding an AGL8-like gene product and, therefore, has been genetically modified by man. In addition, a seed plant that contains, for example, a mutation in an endogenous AGL8-like gene product regulatory element or coding sequence as a result of calculated exposure to a mutagenic agent, such as a chemical mutagen, or an "insertional mutagen," such as a transposon, also is considered a non-naturally occurring seed plant, since it as been genetically modified by man. In contrast, a seed plant containing only spontaneous or naturally occurring mutations is not a "non-naturally occurring seed plant" as defined herein and, therefore, is not encompassed within the invention. One skilled in the art understands that, while a non-naturally occurring seed plant typically has a nucleotide sequence that is altered as compared to a naturally occurring seed plant, a non-naturally occurring seed plant also can be genetically modified by man without altering its nucleotide sequence, for example, by modifying its methylation pattern.

The term "ectopically," as used herein in reference to expression of a nucleic acid molecule encoding an AGL8-like gene product, refers to an expression pattern that is distinct from the expression pattern in a wild type seed plant. Thus, one skilled in the art understands that ectopic expression of a nucleic acid encoding an AGL8-like gene product can refer to expression in a cell type other than a cell type in which the nucleic acid molecule normally is expressed, or at a time other than a time at which the nucleic acid molecule normally is expressed, or at a level other than the level at which the nucleic acid molecule normally is expressed. In wild type Arabidopsis, for example, AGL8 expression is normally restricted during the later stages of floral development to the carpel valves and is not seen in the replum, which is the small strip of cells separating the carpel valves. However, under control of a constitutive promoter such as the cauliflower mosaic virus 35S promoter, AGL8 is expressed in the replum and, additionally, is expressed at higher than normal levels in other tissues such as valve margin and, thus, is ectopically expressed.

The term "delayed," as used herein in reference to the timing of seed dispersal in a fruit produced by a non-naturally occurring seed plant of the invention, means a significantly later time of seed dispersal as compared to the time seeds normally are dispersed from a corresponding seed plant lacking an ectopically expressed nucleic acid molecule encoding an AGL8-like gene product. Thus, the term "delayed" is used broadly to encompass both seed dispersal that is significantly postponed as compared to the seed dispersal in a corresponding seed plant, and to seed dispersal that is completely precluded, such that fruits never release their seeds unless there is human or other intervention.

It is recognized that there can be natural variation of the time of seed dispersal within a seed plant species or variety. However, a "delay" in the time of seed dispersal in a non-naturally occurring seed plant of the invention readily can be identified by sampling a population of the non-naturally occurring seed plants and determining that the normal distribution of seed dispersal times is significantly later, on average, than the normal distribution of seed dispersal times in a population of the corresponding seed plant species or variety that does not contain an ectopically expressed nucleic acid molecule encoding an AGL8-like gene product. Thus, production of non-naturally occurring seed plants of the invention provides a means to skew the normal distribution of the time of seed dispersal from pollination, such that seeds are dispersed, on average, at least about 1%, 2%, 5%, 10%, 30%, 50% or 100% later than in the corresponding seed plant species that does not contain an ectopically expressed nucleic acid molecule encoding an AGL8-like gene product.

A delay in seed dispersal of even one to two days can be valuable in increasing the amount of seed successfully harvested from a seed plant. In canola rapeseed, for example, dehiscence normally occurs about 8 weeks post-pollination. In a non-naturally occurring canola rapeseed that ectopically expresses an AGL8-like gene product, dehiscence can occur one to two days later than in the wild type variety, allowing a significantly greater percentage of the seed crop to be harvested rather than lost through uncontrolled seed dispersal.

The present invention relates to the use of nucleic acid molecules encoding particular "AGAMOUS-LIKE" or "AGL" gene products. AGAMOUS (AG) is a floral organ identity gene, one of a related family of transcription factors that, in various combinations, specify the identity of the floral organs: the petals, sepals, stamens and carpels (Bowman et al., *Devel.* 112:1–20 (1991); Weigel and Meyerowitz, *Cell* 78:203–209 (1994); Yanofsky, *Annual Rev. Plant Physiol. Mol. Biol.* 46:167–188 (1995)). The AGAMOUS gene product is essential for specification of carpel and stamen identity (Bowman et al., *The Plant Cell* 1:37–52 (1989); Yanofsky et al., *Nature* 346:35–39 (1990)). Related genes have recently been identified and denoted "AGAMOUS-LIKE" or "AGL" genes (Ma et al., *Genes Devel.* 5:484–495 (1991); Mandel and Yanofsky, *The Plant Cell* 7:1763–1771 (1995), which is incorporated herein by reference).

AGL8, like AGAMOUS and other AGL genes, is characterized, in part, in that it is a plant MADS box gene. The plant MADS box genes generally encode proteins of about 260 amino acids including a highly conserved MADS domain of about 56 amino acids (Riechmann and Meyerowitz, *Biol. Chem.* 378:1079–1101 (1997), which is incorporated herein by reference). The MADS domain, which was first identified in the Arabidopsis AGAMOUS and Antirrhimum majus DEFICIENS genes, is conserved among transcription factors found in humans (serum response factor; SRF) and yeast (MCM1; Norman et al., *Cell* 55:989–1003 (1988); Passmore et al., *J. Mol. Biol.* 204:593–606 (1988), and is the most highly conserved region of the MADS domain proteins. The MADS domain is the major determinant of sequence specific DNA-binding activity and can also perform dimerization and other accessory functions (Huang et al., *The Plant Cell* 8:81–94 (1996)). The MADS domain frequently resides at the N-terminus, although some proteins contain additional residues N-terminal to the MADS domain.

The "intervening domain" or "I-domain," located immediately C-terminal to the MADS domain, is a weakly conserved domain having a variable length of approximately 30 amino acids (Purugganan et al., *Genetics* 140:345–356 (1995)). In some proteins, the I-domain plays a role in the formation of DNA-binding dimers. A third domain present in plant MADS domain proteins is a moderately conserved 70 amino acid region denoted the "keratin-like domain" or "K-domain." Named for its similarity to regions of the keratin molecule, the structure of the K-domain appears capable of forming amphipathic helices and may mediate protein-protein interactions (Ma et al., *Genes Devel.* 5:484–495 (1991)). The most variable domain, both in sequence and in length, is the carboxy-terminal or "C-domain" of the MADS domain proteins. Dispensable for DNA binding and protein dimerization in some MADS domain proteins, the function of this C-domain remains unknown.

Arabidopsis AGL8 is a 242 amino acid MADS box protein (see FIG. 6; SEQ ID NO:2; Mandel and Yanofsky, supra, 1995). The AGL8 MADS domain resides at amino acids 2 to 56 of SEQ ID NO:2. The K-domain of AGL8 resides at amino acids 92 to 158 of SEQ ID NO:2.

In wild-type Arabidopsis, AGL8 RNA accumulates in two distinct phases, the first occurring during inflorescence development in the stem and cauline leaves and the second in the later stages of flower development (Mandel and Yanofsky, supra, 1995). In particular, AGL8 RNA is first detected in the inflorescence meristem as soon as the plant switches from vegetative to reproductive development. As the inflorescence stem elongates, AGL8 RNA accumulates in the inflorescence meristem and in the stem. Secondly, although AGL8 is not detected in the initial stages (1 and 2) of flower development, AGL8 expression resumes at approximately stage 3 in the center of the floral dome in the region corresponding to the fourth (carpel) whorl. AGL8 expression is excluded from all other primordia and the pedicel. The time of AGL8 expression in the fourth carpel whorl generally corresponds to the time at which the organ identity genes APETALA3, PISTILLATA AND AGAMOUS begin to be expressed (Yanofsky et al., *Nature* 346:35–39 (1990); Drews et al., *Cell* 65:991–1002 (1991); Jack et al., *Cell* 68:683–697 (1992); Goto and Meyerowitz, *Genes Devel.* 8:1548–1560 (1994)). At later stages, AGL8 expression becomes localized to the carpel walls, in the region that constitutes the valves of the ovary, and is absent from nearly all other cell types of the carpel. No AGL8 RNA expression is detected in the ovules, stigmatic tissues or the septum that divides the ovary. Thus, in nature, AGL8 expression during the later stages of floral development is restricted to the valves of the carpels and to the cells within the style.

As used herein, the term "AGL8-like gene product" means a gene product that has the same or similar function as Arabidopsis AGL8 such that, when ectopically expressed in a seed plant, the normal development of the dehiscence zone is altered, and seed dispersal is delayed. An AGL8-like gene product can have, for example, the ability to convert cells of the outer replum to a valve cell identity. Arabidopsis AGL8 (SEQ ID NO:2) is an example of an AGL8-like gene product as defined herein. As disclosed in Example I, ectopic expression of Arabidopsis AGL8 (SEQ ID NO:2) under control of a tandem CaMV 35S promoter, in which the intrinsic promoter element has been duplicated, alters formation of the dehiscence zone, thereby resulting in fruit characterized by a complete lack of seed dispersal. An AGL8-like gene product also can be characterized, in part, by its ability to interact with AGL1 and, additionally, its ability to interact with AGL5.

An AGL8-like gene product generally is characterized, in part, by having an amino acid sequence that has at least about 50% amino acid identity with the amino acid sequence of Arabidopsis AGL8 (SEQ ID NO: 2). An AGL8-like gene product can have, for example, an amino acid sequence with greater than about 65% amino acid sequence identity with Arabidopsis AGL8 (SEQ ID NO:2), preferably greater than about 75% amino acid identity with Arabidopsis AGL8 (SEQ ID NO:2), more preferably greater than about 85% amino acid identity with Arabidopsis AGL8 (SEQ ID NO:2), and can be a sequence having greater than about 90%, 95% or 97% amino acid identity with Arabidopsis AGL8 (SEQ ID NO:2).

Preferably, an AGL8-like gene product is orthologous to the seed plant species in which it is ectopically expressed. A nucleic acid molecule encoding Arabidopsis AGL8 (SEQ ID NO:2), for example, can be ectopically expressed in an Arabidopsis plant to produce a non-naturally occurring Arabidopsis variety characterized by delayed seed dispersal. Similarly, a nucleic acid molecule encoding canola AGL8 can be ectopically expressed in a canola plant to produce a non-naturally occurring canola variety characterized by delayed seed dispersal.

A nucleic acid molecule encoding an AGL8-like gene product also can be ectopically expressed in a heterologous seed plant to produce a non-naturally occurring seed plant characterized by delayed seed dispersal. AGAMOUS-like gene products have been widely conserved throughout the plant kingdom; for example, AGAMOUS has been conserved in tomato (TAG1) and maize (ZAG1), indicating that orthologs of AGAMOUS-like genes are present in most, if not all, angiosperms (Pnueli et al., *The Plant Cell* 6:163–173 (1994); Schmidt et al., *The Plant Cell* 5:729–737 (1993)). AGL8-like gene products such as AGL8 orthologs also can be conserved and can function across species boundaries to delay seed dispersal. Thus, ectopic expression of a nucleic acid molecule encoding Arabidopsis AGL8 (SEQ ID NO:2) in a heterologous seed plant within the Brassicaceae such as *Brassica napus L.* (rapeseed) or within the Fabaceae such as in Glycine (soybean) can alter normal development of the dehiscence zone, thereby resulting in delayed seed dispersal. Furthermore, a nucleic acid molecule encoding Arabidopsis AGL8 (SEQ ID NO:2), for example, can be ectopically expressed in more distantly related heterologous seed plants, including dehiscent seed plants as well as other dicotyledonous and monocotyledonous angiosperms and gymnosperms and, upon ectopic expression, can alter normal development of the dehiscence zone and delay seed dispersal in the heterologous seed plant.

As used herein, the term "AGL8-like gene product" encompasses an active segment of an AGL8-like gene product, which is a polypeptide portion of an AGL8-like gene product that, when ectopically expressed, alters normal development of the dehiscence zone and delays seed dispersal. An active segment can be, for example, an amino terminal, internal or carboxy terminal fragment of Arabidopsis AGL8 (SEQ ID NO:2) that, when ectopically expressed in a seed plant, alters normal development of the dehiscence zone and delays seed dispersal. An active segment of an AGL8-like gene product can include, for example, the MADS domain and can have the ability to bind DNA specifically. The skilled artisan will recognize that a nucleic acid molecule encoding an active segment of an AGL8-like gene product can be useful in producing a seed plant of the invention characterized by delayed seed dispersal and in the related methods and kits of the invention described further below.

An active segment of an AGL8-like gene product can be identified using the methods described in Example I or using other routine methodology. Briefly, a seed plant such as Arabidopsis can be transformed with a nucleic acid molecule under control of a constitutive regulatory element such as a tandem CaMV 35S promoter. Phenotypic analysis of the seed plant reveals whether a seed plant ectopically expressing a particular polypeptide portion is characterized by delayed seed dispersal. In transgenic plants in which seed dispersal is delayed, further analysis can be performed to confirm that normal development of the dehiscence zone has been altered. For analysis of a large number of polypeptide portions of an AGL8-like gene product, nucleic acid molecules encoding the polypeptide portions can be assayed in pools, and active pools subsequently subdivided to identify the active nucleic acid molecule.

In one embodiment, the invention provides a non-naturally occurring seed plant that is characterized by delayed seed dispersal due to ectopic expression of a nucleic acid molecule encoding an AGL8-like gene product having substantially the amino acid sequence of an AGL8 ortholog. As used herein, the term "AGL8 ortholog" means an ortholog of Arabidopsis AGL8 (SEQ ID NO:2) and refers to an AGL8-like gene product that, in a particular seed plant variety, has the highest percentage homology at the amino acid level to Arabidopsis AGL8 (SEQ ID NO:2). An AGL8 ortholog can be, for example, a Brassica AGL8 ortholog such as a Brassica napus L. AGL8 ortholog, or a Fabacea AGL8 ortholog such as a soybean, pea, lentil, or bean AGL8 ortholog. An AGL8 ortholog from the long-day plant Sinapis alba, designated SaMADS B, has been described (Menzel et al., *Plant J.* 9:399–408 (1996), which is incorporated herein by reference). Novel AGL8 ortholog cDNAs can be isolated from additional seed plant species using a nucleotide sequence as a probe and methods well known in the art of molecular biology (Glick and Thompson (eds.), *Methods in Plant Molecular Biology and Biotechnology,* Boca Raton, Fla.: CRC Press (1993); Sambrook et al. (eds.), *Molecular Cloning: A Laboratory Manual* (Second Edition), Plainview, N.Y.: Cold Spring Harbor Laboratory Press (1989), each of which is incorporated herein by reference).

As used herein, the term "substantially the amino acid sequence," when used in reference to an AGL8 ortholog, is intended to mean a polypeptide or polypeptide segment having an identical amino acid sequence, or a polypeptide or polypeptide segment having a similar, non-identical sequence that is considered by those skilled in the art to be a functionally equivalent amino acid sequence. For example, an AGL8-like gene product having substantially the amino acid sequence of Arabidopsis AGL8 can have an amino acid sequence identical to the sequence of Arabidopsis AGL8 (SEQ ID NO:2) shown in FIG. 6, or a similar, non-identical sequence that is functionally equivalent. In particular, an amino acid sequence that is "substantially the amino acid sequence" of AGL8 can have one or more modifications such as amino acid additions, deletions or substitutions relative to the AGL8 amino acid sequence shown (SEQ ID NO:2), provided that the modified polypeptide retains substantially the ability to alter normal development of the dehiscence zone and delay seed dispersal when ectopically expressed in the seed plant. Comparison of sequences for substantial similarity can be performed between two sequences of any length and usually is performed with sequences between about 6 and 1200 residues, preferably between about 10 and 100 residues and more preferably between about 25 and 35 residues. Such comparisons for substantial similarity are performed using methodology routine in the art.

It is understood that minor modifications of primary amino acid sequence can result in an AGL8-like gene product that has substantially equivalent or enhanced function as compared to the AGL8 ortholog from which it was derived. Further, various molecules can be attached to an AGL8 ortholog or active segment thereof, for example, other polypeptides, antigenic or other peptide tags, carbohydrates, lipids, or chemical moieties. Such modifications are included within the term AGL8 ortholog as defined herein.

One or more point mutations can be introduced into a nucleic acid molecule encoding an AGL8 ortholog to yield a modified nucleic acid molecule using, for example, site-directed mutagenesis (see Wu (Ed.), *Meth. In Enzymol.* Vol. 217, San Diego: Academic Press (1993); Higuchi, "Recombinant PCR" in Innis et al. (Ed.), *PCR Protocols,* San Diego: Academic Press, Inc. (1990), each of which is incorporated herein by reference). Such mutagenesis can be used to introduce a specific, desired amino acid insertion, deletion or substitution; alternatively, a nucleic acid sequence can be synthesized having random nucleotides at one or more predetermined positions to generate random amino acid substitutions. Scanning mutagenesis also can be useful in generating a modified nucleic acid molecule encoding substantially the amino acid sequence of an AGL8 ortholog.

Modified nucleic acid molecules can be routinely assayed for the ability to alter normal development of the dehiscence zone and to delay seed dispersal. In the same manner as described in Examples I and III, a nucleic acid molecule encoding substantially the amino acid sequence of an AGL8 ortholog can be ectopically expressed, for example, using a constitutive regulatory element such as the CaMV 35S promoter or using a dehiscence zone-selective regulatory element such as the AGL1 promoter. If such ectopic expression results in a seed plant in which the dehiscence zone fails to develop and in which seed dispersal is delayed, the modified polypeptide or segment is an "AGL8 ortholog" as defined herein.

A non-naturally occurring seed plant of the invention that is characterized by delayed seed dispersal can be one of a variety of seed plant species, such as a dehiscent seed plant or another monocotyledonous and dicotyledonous angiosperm or gymnosperm. A useful seed plant of the invention can be a dehiscent seed plant, and a particularly useful seed plant of the invention can be a member of the Brassicaceae, such as rapeseed, or a member of the Fabaceae, such as a soybean, pea, lentil or bean plant.

As used herein, the term "seed plant" means an angiosperm or gymnosperm. An angiosperm is a seed-bearing plant whose seeds are borne in a mature ovary (fruit). An angiosperm commonly is recognized as a flowering plant. Angiosperms are divided into two broad classes based on the number of cotyledons, which are seed leaves that generally store or absorb food. Thus, a monocotyledonous angiosperm is an angiosperm having a single cotyledon, whereas a dicotyledonous angiosperm is an angiosperm having two cotyledons. A variety of angiosperms are known including, for example, oilseed plants, leguminous plants, fruit-bearing plants, ornamental flowers, cereal plants and hardwood trees, which general classes are not necessarily exclusive. The skilled artisan will recognize that the methods of the invention can be practiced using these or other angiosperms, as desired. A gymnosperm is a seed-bearing plant with seeds not enclosed in an ovary.

In one embodiment, the invention provides a non-naturally occurring dehiscent seed plant that is characterized by delayed seed dispersal due to ectopic expression of a nucleic acid molecule encoding an AGL8-like gene product in the dehiscent seed plant. As used herein, the term "dehiscent seed plant" means a seed plant that produces a dry dehiscent fruit, which has fruit walls that open to permit escape of the seeds contained therein. Dehiscent fruits commonly contain several seeds and include the fruits known, for example, as legumes, capsules and siliques.

In one embodiment, the invention provides a non-naturally occurring seed plant that is characterized by delayed seed dispersal due to ectopic expression of a nucleic acid molecule encoding an AGL8-like gene product, where the seed plant is a member of the Brassicaceae. The Brassicaceae, commonly known as the Brassicas, are a diverse group of crop plants with great economic value worldwide (see, for example, Williams and Hill, *Science* 232:1385–1389 (1986), which is incorporated herein by reference). The Brassicaceae produce seed oils for margarine, salad oil, cooking oil, plastic and industrial uses; condiment mustard; leafy, stored, processed and pickled vegetables; animal fodders and green manures for soil rejuvenation. A particularly useful non-naturally occurring Brassica seed plant of the invention is the oilseed plant canola.

There are six major Brassica species of economic importance, each containing a range of plant forms. Brassica napus includes plants such as the oilseed rapes and rutabaga. *Brassica oleracea* are the cole crops such as cabbage, cauliflower, kale, kohlrabi and Brussels sprouts. *Brassica campestris* (*Brassica rapa*) includes plants such as Chinese cabbage, turnip and pak choi. *Brassica juncea* includes a variety of mustards; *Brassica nigra* is the black mustard; and *Brassica carinata* is Ethiopian mustard. The skilled artisan understands that any member of the Brassicaceae can be modified as disclosed herein to produce a non-naturally occurring Brassica plant characterized by delayed seed dispersal.

In a second embodiment, the invention provides a non-naturally occurring seed plant that is characterized by delayed seed dispersal due to ectopic expression of a nucleic acid molecule encoding an AGL8-like gene product, where the seed plant is a member of the Fabaceae. The Fabaceae, which are commonly known as members of the pea family, are seed plants that produce a characteristic dry dehiscent fruit known as a legume. The legume is derived from a single carpel and dehisces along the suture of the carpel margins and along the median vein. The Fabaceae encompass both grain legumes and forage legumes. Grain legumes include, for example, soybean (glycine), pea, chickpea, moth bean, broad bean, kidney bean, lima bean, lentil, cowpea, dry bean and peanut. Forage legumes include alfalfa, lucerne, birdsfoot trefoil, clover, stylosanthes species, lotononis bainessii and sainfoin. The skilled artisan will recognize that any member of the Fabaceae can be modified as disclosed herein to produce a non-naturally occurring seed plant of the invention characterized by delayed seed dispersal.

A non-naturally occurring seed plant of the invention characterized by delayed seed dispersal also can be a member of the plant genus Cuphea (family Lythraceae). A Cuphea seed plant is particularly valuable since Cuphea oilseeds contain industrially and nutritionally important medium-chain fatty acids, especially lauric acid, which is currently supplied only by coconut and palm kernel oils.

A non-naturally occurring seed plant of the invention also can be, for example, one of the monocotyledonous grasses, which produce many of the valuable small-grain cereal crops of the world. In a non-naturally occurring small grain cereal plant of the invention, grain remains on the seed plant longer and, Ectopic expression of a nucleic acid molecule encoding an AGL8-like gene product, or suppression of AGL1 and AGL5 expression as described below, can be useful in generating a non-naturally occurring small grain cereal plant, such as a barley, wheat, oat, rye, orchard grass, guinea grass, sorghum or turf grass plant characterized by delayed seed dispersal.

The invention also provides a transgenic seed plant that is characterized by delayed seed dispersal due to ectopic expression of a nucleic acid molecule encoding an AGL8-like gene product. In a transgenic seed plant of the invention, the ectopically expressed nucleic acid molecule encoding an AGL8-like gene product can be operatively linked to an exogenous regulatory element. The invention provides, for example, a transgenic seed plant characterized by delayed seed dispersal having an ectopically expressed nucleic acid molecule encoding an AGL8-like gene product that is operatively linked to an exogenous constitutive regulatory element. In one embodiment, the invention provides a transgenic seed plant that is characterized by delayed seed dispersal due to ectopic expression of an exogenous nucleic acid molecule encoding substantially the amino acid sequence of an AGL8 ortholog operatively linked to an exogenous cauliflower mosaic virus 35S promoter.

The invention also provides a transgenic seed plant that is characterized by delayed seed dispersal due to ectopic expression of a nucleic acid molecule encoding an AGL8-like gene product operatively linked to a dehiscence zone-selective regulatory element. The dehiscence zone-selective regulatory element can be, for example, an AGL1 regulatory element or AGL5 regulatory element. The AGL1 regulatory element can be derived from the Arabidopsis AGL1 genomic sequence disclosed herein as SEQ ID NO:3 and can be, for example, a 5' regulatory sequence or intronic regulatory element. Similarly, the AGL5 regulatory element can be derived from the Arabidopsis AGL5 genomic sequence disclosed herein as SEQ ID NO:4 and can be, for example, a 5' regulatory sequence or intronic regulatory element In one embodiment, a transgenic seed plant of the invention has an ectopically expressed exogenous nucleic acid molecule encoding substantially the amino acid sequence of an AGL8 ortholog operatively linked to a dehiscence zone-selective regulatory element that is an AGL1 regulatory element having at least fifteen contiguous nucleotides of nucleotides 1 to 2599 of SEQ ID NO:3; nucleotides 2833 to 4128 of SEQ ID NO:3; nucleotides 4211 to 4363 of SEQ ID NO:3; nucleotides 4426 to 4554 of SEQ ID NO:3; nucleotides 4796 to 4878 of SEQ ID NO:3; nucleotides 4921 to 5028 of SEQ ID NO:3; or nucleotides 5421 to 5682 of SEQ ID NO:3.

In another embodiment, a transgenic seed plant of the invention has an ectopically expressed exogenous nucleic acid molecule encoding substantially the amino acid sequence of an AGL8 ortholog operatively linked to a dehiscence zone-selective regulatory element that is an AGL5 regulatory element having at least fifteen contiguous nucleotides of nucleotides 1 to 1890 of SEQ ID NO:4; nucleotides 2536 to 2683 of SEQ ID NO:4; nucleotides 2928 to 5002 of SEQ ID NO:4; nucleotides 5085 to 5204 of SEQ ID NO:4; nucleotides 5367 to 5453 of SEQ ID NO:4; nucleotides 5645 to 5734 of SEQ ID NO:4; or nucleotides 6062 to 6138 of SEQ ID NO:4.

As used herein, the term "transgenic" refers to a seed plant that contains an exogenous nucleic acid molecule, which can be derived from the same seed plant species or a heterologous seed plant species.

The term "exogenous," as used herein in reference to a nucleic acid molecule and a transgenic seed plant, means a nucleic acid molecule originating from outside the seed plant. An exogenous nucleic acid molecule can be, for example, a nucleic acid molecule encoding an AGL8-like gene product or an exogenous regulatory element such as a constitutive regulatory element or a dehiscence zone-selective regulatory element, as described further below. An exogenous nucleic acid molecule can have a naturally occurring or non-naturally occurring nucleotide sequence and can be a heterologous nucleic acid molecule derived from a different seed plant species than the seed plant into which the nucleic acid molecule is introduced or can be a nucleic acid molecule derived from the same seed plant species as the seed plant into which it is introduced.

The term "operatively linked," as used in reference to a regulatory element and a nucleic acid molecule, means that the regulatory element confers regulated expression upon the operatively linked nucleic acid molecule. Thus, the term "operatively linked," as used in reference to an exogenous regulatory element such as a dehiscence zone-selective regulatory element and a nucleic acid molecule encoding an AGL8-like gene product, means that the dehiscence zone-selective regulatory element is linked to the nucleic acid molecule encoding an AGL8-like gene product such that the expression pattern of the dehiscence zone-selective regulatory element is conferred upon the nucleic acid molecule encoding the AGL8-like gene product. It is recognized that a regulatory element and a nucleic acid molecule that are operatively linked have, at a minimum, all elements essential for transcription, including, for example, a TATA box.

As used herein, the term "constitutive regulatory element" means a regulatory element that confers a level of expression upon an operatively linked nucleic molecule that is relatively independent of the cell or tissue type in which the constitutive regulatory element is expressed. A constitutive regulatory element that is expressed in a seed plant generally is widely expressed in a large number of cell and tissue types.

A variety of constitutive regulatory elements useful for ectopic expression in a transgenic seed plant are well known in the art. The cauliflower mosaic virus 35S (CaMV 35S) promoter, for example, is a well-characterized constitutive regulatory element that produces a high level of expression in all plant tissues (Odell et al., *Nature* 313:810–812 (1985)). The CaMV 35S promoter can be particularly useful due to its activity in numerous diverse seed plant species (Benfey and Chua, *Science* 250:959–966 (1990); Futterer et al., *Physiol. Plant* 79:154 (1990); Odell et al., supra, 1985). A tandem 35S promoter, in which the intrinsic promoter element has been duplicated, confers higher expression levels in comparison to the unmodified 35S promoter (Kay et al., *Science* 236:1299 (1987)). Other constitutive regulatory elements useful for ectopically expressing a nucleic acid molecule encoding an AGL8-like gene product in a transgenic seed plant of the invention include, for example, the cauliflower mosaic virus 19S promoter; the Figwort mosaic virus promoter; and the nopaline synthase (nos) gene promoter (Singer et al., *Plant Mol. Biol.* 14:433 (1990); An, *Plant Physiol.* 81:86 (1986)).

Additional constitutive regulatory elements including those for efficient ectopic expression in monocots also are known in the art, for example, the pEmu promoter and promoters based on the rice Actin-1 5' region (Last et al., *Theor. Appl. Genet.* 81:581 (1991); Mcelroy et al., *Mol. Gen. Genet.* 231:150 (1991); Mcelroy et al., *Plant Cell* 2:163 (1990)). Chimeric regulatory elements, which combine elements from different genes, also can be useful for ectopically expressing a nucleic acid molecule encoding an AGL8-like gene product (Comai et al., *Plant Mol. Biol.* 15:373 (1990)). One skilled in the art understands that a particular constitutive regulatory element is chosen based, in part, on the seed plant species in which a nucleic acid molecule encoding an AGL8-like gene product is to be ectopically expressed and on the desired level of expression.

An exogenous regulatory element useful in a transgenic seed plant of the invention also can be an inducible regulatory element, which is a regulatory element that confers conditional expression upon an operatively linked nucleic acid molecule, where expression of the operatively linked nucleic acid molecule is increased in the presence of a particular inducing agent or stimulus as compared to expression of the nucleic acid molecule in the absence of the inducing agent or stimulus. Particularly useful inducible regulatory elements include copper-inducible regulatory elements (Mett et al., *Proc. Natl. Acad. Sci. USA* 90:4567–4571 (1993); Furst et al., *Cell* 55:705–717 (1988)); tetracycline and chlor-tetracycline-inducible regulatory elements (Gatz et al., *Plant J.* 2:397–404 (1992); Röder et al., *Mol. Gen. Genet.* 243:32–38 (1994); Gatz, *Meth. Cell Biol.* 50:411–424 (1995)); ecdysone inducible regulatory elements (Christopherson et al., *Proc. Natl. Acad. Sci. USA* 89:6314–6318 (1992); Kreutzweiser et al., *Ecotoxicol. Envi-*

*ron. Safety* 28:14–24 (1994)); heat shock inducible regulatory elements (Takahashi et al., *Plant Physiol.* 99:383–390 (1992); Yabe et al., *Plant Cell Physiol.* 35:1207–1219 (1994); Ueda et al., *Mol. Gen. Genet.* 250:533–539 (1996)); and lac operon elements, which are used in combination with a constitutively expressed lac repressor to confer, for example, IPTG-inducible expression (Wilde et al., *EMBO J.* 11:1251–1259 (1992)).

An inducible regulatory element useful in the transgenic seed plants of the invention also can be, for example, a nitrate-inducible promoter derived from the spinach nitrite reductase gene (Back et al., *Plant Mol. Biol.* 17:9 (1991)) or a light-inducible promoter, such as that associated with the small subunit of RuBP carboxylase or the LHCP gene families (Feinbaum et al., *Mol. Gen. Genet.* 226:449 (1991); Lam and Chua, *Science* 248:471 (1990)). Additional inducible regulatory elements include salicylic acid inducible regulatory elements (Uknes et al., *Plant Cell* 5:159–169 (1993); Bi et al., *Plant J.* 8:235–245 (1995)); plant hormone-inducible regulatory elements (Yamaguchi-Shinozaki et al., *Plant Mol. Biol.* 15:905 (1990); Kares et al., *Plant Mol. Biol.* 15:225 (1990)); and human hormone-inducible regulatory elements such as the human glucocorticoid response element (Schena et al., *Proc. Natl. Acad. Sci. USA* 88:10421 (1991)).

It should be recognized that a non-naturally occurring seed plant of the invention, which contains an ectopically expressed nucleic acid molecule encoding an AGL8-like gene product, also can contain one or more additional modifications, including naturally and non-naturally occurring modifications, that can modulate the delay in seed dispersal. For example, the plant hormone ethylene promotes fruit dehiscence, and modified expression or activity of positive or negative regulators of the ethylene response can be included in a seed plant of the invention (see, generally, Meakin and Roberts, *J. Exp. Botany* 41:1003–1011 (1990); Ecker, *Science* 268:667–675 (1995); Chao et al., *Cell* 89:1133–1144 (1997)).

Mutations in positive regulators of the ethylene response show a reduction or absence of responsiveness to treatment with exogenous ethylene. Arabidopsis mutations in positive regulators of the ethylene response include mutations in etr, which inactivate a histidine kinase ethylene receptor (Bleeker et al., *Science* 241:1086–1089 (1988); Schaller and Bleeker, *Science* 270:1809–1811 (1995)); ers (Hua et al., *Science* 269:1712–1714 (1995)); ein2 (Guzman and Ecker, *Plant Cell* 2:513 (1990)); ein3 (Rothenberg and Ecker, *Sem. Dev. Biol. Plant Dev. Genet.* 4:3–13 (1993); Kieber and Ecker, *Trends Genet.* 9:356–362 (1993)); ain1 (van der Straeten et al., *Plant Physiol.* 102:401–408 (1993)); eti (Harpham et al., *An. Bot.* 68:55 (1991)) and ein4, ein5, ein6, and ein7 (Roman et al., *Genetics* 139: 1393–1409 (1995)). Similar genetic functions are found in other seed plant species; for example, the never-ripe mutation corresponds to etr and confers ethylene insensitivity in tomato (Lanahan et al., *The Plant Cell* 6:521–530 (1994); Wilkinson et al., *Science* 270:1807–1809 (1995)). A seed plant of the invention can include a modification that results in altered expression or activity of any such positive regulator of the ethylene response. A mutation in a positive regulator, for example, can be included in a seed plant of the invention and can modify the delay in seed dispersal in such plants, for example, by further postponing the delay in seed dispersal.

Mutations in negative regulators of the ethylene response display ethylene responsiveness in the absence of exogenous ethylene. Such mutations include those relating to ethylene overproduction, for example, the eto1, eto2, and eto3 mutants, and those relating to constitutive activation of the ethylene signalling pathway, for example, mutations in CTR1, a negative regulator with sequence similarity to the Raf family of protein kinases (Kieber et al., *Cell* 72:427–441 (1993), which is incorporated herein by reference). A seed plant of the invention can include a modification that results in altered expression or activity of any such negative regulator of the ethylene response. A mutation resulting in ethylene responsiveness in the absence of exogenous ethylene, for example, can be included in a non-naturally occurring seed plant of the invention and can modify, for example, diminish, the delay in seed dispersal.

Fruit morphological mutations also can be included in a seed plant of the invention. Such mutations include those in carpel identity genes such as AGAMOUS (Bowman et al., supra, 1989; Yanofsky et al., supra, 1990) and in genes required for normal fruit development such as ETTIN, CRABS CLAW, SPATULA, AGL8 and TOUSLED (Sessions et al., *Development* 121:1519–1532 (1995); Alvarez and Smyth, *Flowering Newsletter* 23:12–17 (1997); and Roe et al., *Cell* 75:939–950 (1993)). Thus, it is understood that a seed plant of the invention having an ectopically expressed nucleic acid molecule encoding an AGL8-like gene product can include one or more additional genetic modifications, which can diminish or enhance the delay in seed dispersal.

The present invention also provides methods of producing a non-naturally occurring seed plant characterized by delayed seed dispersal. A method of the invention entails ectopically expressing a nucleic acid molecule encoding an AGL8-like gene product in the seed plant, whereby seed dispersal is delayed due to ectopic expression of the nucleic acid molecule.

As discussed above, the term "ectopically" refers to expression of a nucleic acid molecule encoding an AGL8-like gene product in a cell type other than a cell type in which the nucleic acid molecule is normally expressed, at a time other than a time at which the nucleic acid molecule is normally expressed or at n expression level other than the level at which the nucleic acid normally is expressed. In wild type Arabidopsis, for example, AGL8 expression is normally restricted during the later stages of floral development to the carpel valves and is not seen in the outer replum. In the methods of the invention, particularly useful ectopic expression of a nucleic acid molecule encoding an AGL8-like gene product involves expression in the cells of the outer replum, which are the progenitors of the dehiscence zone.

Actual ectopic expression of an AGL8-like gene product is dependent on various factors. The ectopic expression can be widespread expression throughout most or all plant tissues or can be expression restricted to a small number of plant tissues, and can be achieved by a variety of routine techniques. Mutagenesis, including seed or pollen mutagenesis, can be used to generate a non-naturally occurring seed plant, in which a nucleic acid molecule encoding an AGL8-like gene product is ectopically expressed. Ethylmethane sulfonate (EMS) mutagenesis, transposon mediated mutagenesis or T-DNA mediated mutagenesis also can be useful in ectopically expressing an AGL8-like gene product to produce a seed plant characterized by delayed seed dispersal (see, generally, Glick and Thompson, supra, 1993). While not wishing to be bound by any particular mechanism, ectopic expression in a mutagenized plant can result from inactivation of one or more negative regulators of AGL8, for example, from the combined inactivation of AGL1 and AGL5.

Ectopic expression of an AGL8-like gene product also can be achieved by expression of a nucleic acid encoding an AGL8-like gene product from a heterologous regulatory element or from a modified variant of its own promoter. Heterologous regulatory elements include constitutive regulatory elements, which result in expression of the AGL8-like gene product in the outer replum as well as in a variety of other cell types, and dehiscence zone-selective regulatory elements, which produce selective expression of an AGL8-like gene product in a limited number of cell types including the cells of the valve margin or the dehiscence zone.

Ectopic expression of a nucleic acid molecule encoding an AGL8-like gene product can be achieved using an endogenous or exogenous nucleic acid molecule encoding an AGL8-like gene product. A recombinant exogenous nucleic acid molecule can contain a heterologous regulatory element that is operatively linked to a nucleic acid sequence encoding an AGL8-like gene product. Methods for producing the desired recombinant nucleic acid molecule under control of a heterologous regulatory element and for producing a non-naturally occurring seed plant of the invention are well known in the art (see, generally, Sambrook et al., supra, 1989; Glick and Thompson, supra, 1993).

An exogenous nucleic acid molecule can be introduced into a seed plant for ectopic expression using a variety of transformation methodologies including Agrobacterium-mediated transformation and direct gene transfer methods such as electroporation and microprojectile-mediated transformation (see, generally, Wang et al. (eds), *Transformation of Plants and Soil Microorganisms,* Cambridge, UK: University Press (1995), which is incorporated herein by reference). Transformation methods based upon the soil bacterium *Agrobacterium tumefaciens* are particularly useful for introducing an exogenous nucleic acid molecule into a seed plant. The wild type form of Agrobacterium contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An Agrobacterium-based vector is a modified form of a Ti plasmid, in which the tumor inducing functions are replaced by the nucleic acid sequence of interest to be introduced into the plant host.

Agrobacterium-mediated transformation generally employs cointegrate vectors or, preferably, binary vector systems, in which the components of the Ti plasmid are divided between a helper vector, which resides permanently in the Agrobacterium host and carries the virulence genes, and a shuttle vector, which contains the gene of interest bounded by T-DNA sequences. A variety of binary vectors are well known in the art and are commercially available, for example, from Clontech (Palo Alto, Calif.). Methods of coculturing Agrobacterium with cultured plant cells or wounded tissue such as leaf tissue, root explants, hypocotyledons, stem pieces or tubers, for example, also are well known in the art (Glick and Thompson, supra, 1993). Wounded cells within the plant tissue that have been infected by Agrobacterium can develop organs de novo when cultured under the appropriate conditions; the resulting transgenic shoots eventually give rise to transgenic plants that ectopically express a nucleic acid molecule encoding an AGL8-like gene product. Agrobacterium also can be used for transformation of whole seed plants as described in Bechtold et al., *C.R. Acad. Sci. Paris, Life Sci.* 316:1194–1199 (1993), which is incorporated herein by reference). Agrobacterium-mediated transformation is useful for producing a variety of transgenic seed plants (Wang et al., supra, 1995) including transgenic plants of the Brassicaceae family, such as rapeseed, Arabidopsis, mustard, and flax, and transgenic plants of the Fabaceae family such as soybean, pea, lentil and bean.

Microprojectile-mediated transformation also can be used to produce a transgenic seed plant that ectopically expresses an AGL8-like gene product. This method, first described by Klein et al. (*Nature* 327:70–73 (1987), which is incorporated herein by reference), relies on microprojectiles such as gold or tungsten that are coated with the desired nucleic acid molecule by precipitation with calcium chloride, spermidine or PEG. The microprojectile particles are accelerated at high speed into an angiosperm tissue using a device such as the BIOLISTIC PD-1000 (Biorad; Hercules Calif.).

Microprojectile-mediated delivery or "particle bombardment" is especially useful to transform seed plants that are difficult to transform or regenerate using other methods. Microprojectile-mediated transformation has been used, for example, to generate a variety of transgenic plant species, including cotton, tobacco, corn, hybrid poplar and papaya (see Glick and Thompson, supra, 1993) as well as cereal crops such as wheat, oat, barley, sorghum and rice (Duan et al., *Nature Biotech.* 14:494–498 (1996); Shimamoto, *Curr. Opin. Biotech.* 5:158–162 (1994), each of which is incorporated herein by reference). In view of the above, the skilled artisan will recognize that Agrobacterium-mediated or microprojectile-mediated transformation, as disclosed herein, or other methods known in the art can be used to introduce a nucleic acid molecule encoding an AGL8-like gene product into a seed plant for ectopic expression.

In another embodiment, the invention provides a non-naturally occurring seed plant that is characterized by delayed seed dispersal due to suppression of both AGL1 expression and AGL5 expression in the seed plant. Such a non-naturally occurring seed plant characterized by delayed seed dispersal can be, for example, an agl1 agl5 double mutant.

Figure 5:
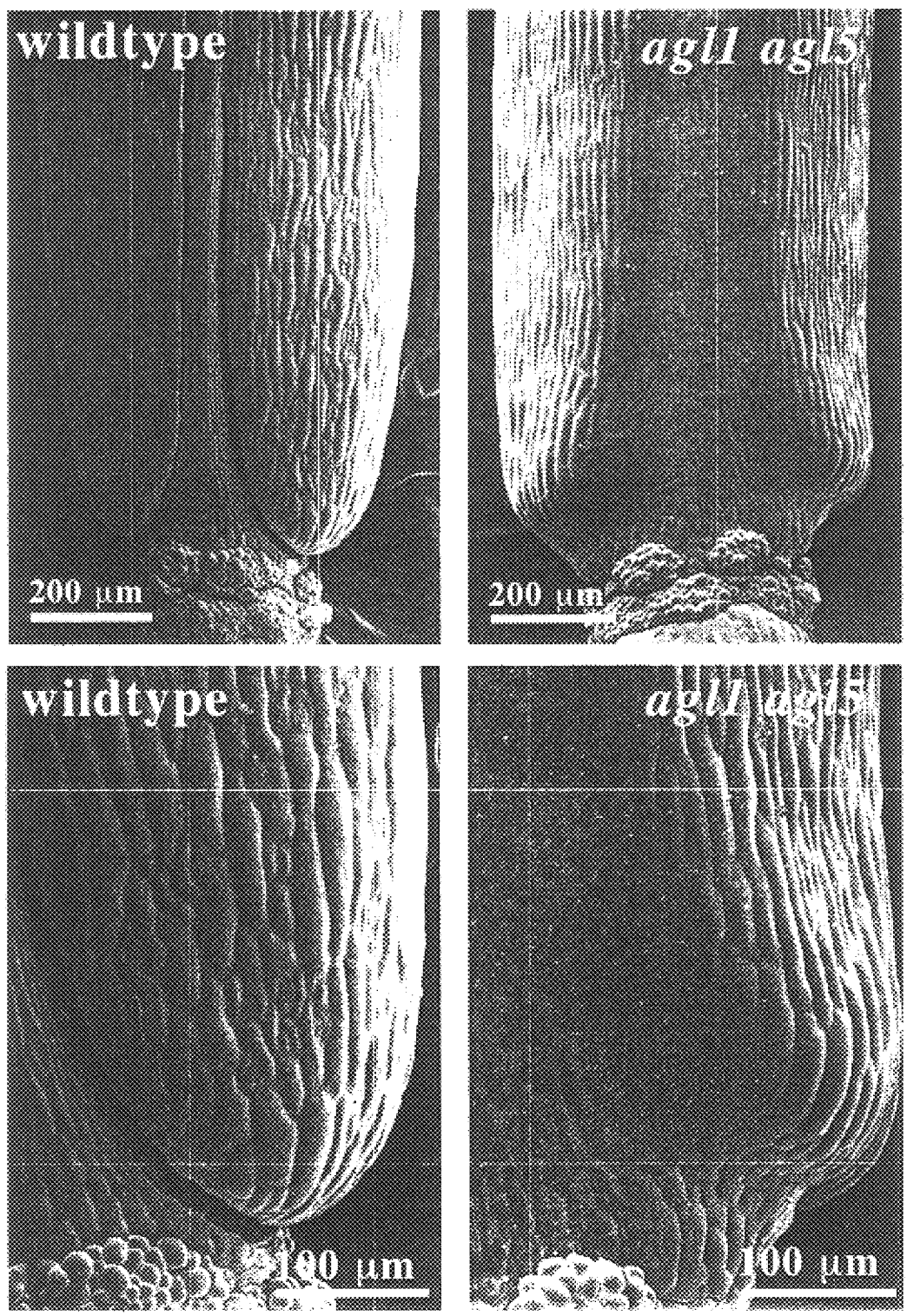
FIG. 5 shows scanning electron micrographs of wild type Arabidopsis and an agl1 agl5 double mutant. The valves are beginning to detach from the replum in the wild type Arabidopsis fruits, which are shown during the process of dehiscence. At the same time in development, the valves of the agl1 agl5 double mutant plant remain attached to the replum.

As disclosed herein, loss-of-function mutations in the AGL1 and AGL5 genes were produced by a combination of homologous recombination and disruptive T-DNA insertion (see Example II). Neither AGL1 nor AGL5 RNA was expressed in the resulting agl1 agl5 double mutant, and scanning electron microscopy revealed that the dehiscence zone failed to develop normally in these mutant seed plants. Furthermore, the mature fruits of these seed plants failed to undergo dehiscence, as shown in FIG. 5. These results indicate that AGL1 or AGL5 gene expression is required for normal development of the dehiscence zone and that suppression of AGL1 expression combined with suppression of AGL5 expression in the seed plant can delay dehiscence, allowing the process of pod shatter to be controlled.

The Arabidopsis AGL1 and AGL5 genes encode MADS box proteins with 85% identity at the amino acid level (see Tables 1 and 2). The AGL1 and AGL5 RNA expression patterns also are strikingly similar. In particular, both RNAs are specifically expressed in flowers, where they accumulate in developing carpels. In particular, strong expression of these genes is observed in the outer replum along the valve/replum boundary (Ma et al., supra, 1991; Savidge et al., *The Plant Cell* 7:721–723 (1995); Flanagan et al., *The Plant Journal* 10:343–353 (1996), each of which is incorporated herein by reference). Thus, AGL1 and AGL5 are expressed in the valve margin, at least within the cells of the outer replum.

TABLE 1

Amino acid identity in the MADS domain and
K-domain of AGAMOUS, AGL1 and AGL5

|  | AGAMOUS | | AGL1 | | AGL5 | |
| --- | --- | --- | --- | --- | --- | --- |
|  | MADS | K | MADS | K | MADS | K |
| AGAMOUS | — | — | 95% | 68% | 95% | 62% |
| AGL1 | — | — | — | — | 100% | 92% |
| AGL5 | — | — | — | — | — | — |

TABLE 2

Amino acid identity in the I-domain and
C-domain of AGAMOUS, AGL1 and AGL5

|  | AGAMOUS | | AGL1 | | AGL5 | |
| --- | --- | --- | --- | --- | --- | --- |
|  | I | C | I | C | I | C |
| AGAMOUS | — | — | — | — | — | — |
| AGL1 | 71% | 39% | — | — | — | — |
| AGL5 | 65% | 37% | 95% | 72% | — | — |

As used herein, the term "AGL1" refers to Arabidopsis AGL1 (SEQ ID NO:6) or an ortholog of Arabidopsis AGL1 (SEQ ID NO:6). An AGL1 ortholog is a MADS box gene product expressed, at least in part, in the valve margins of a seed plant and having homology to the amino acid sequence of Arabidopsis AGL1 (SEQ ID NO:6). AGL1 or an AGL1 ortholog can function, in part, by forming a complex with an AGL8-like gene product. An AGL1 ortholog generally has an amino acid sequence having at least about 63% amino acid identity with Arabidopsis AGL1 (SEQ ID NO:6) and includes polypeptides having greater than about 70%, 75%, 85% or 95% amino acid identity with Arabidopsis AGL1 (SEQ ID NO:6). Given the close relatedness of the AGL1 and AGL5 gene products, one skilled in the art will recognize that an AGL1 ortholog can be distinguished from an AGL5 ortholog by being more closely related to Arabidopsis AGL1 (SEQ ID NO:6) than to Arabidopsis AGL5 (SEQ ID NO:8). An AGL1 ortholog can function in wild type plants, like Arabidopsis AGL1, to limit the domain of AGL8-like gene product expression to the carpel valves during the later stages of floral development.

As used herein, the term "AGL5" refers to Arabidopsis AGL5 (SEQ ID NO:8) or to an ortholog of Arabidopsis AGL5 (SEQ ID NO:8). An AGL5 ortholog is a MADS box gene product expressed, at least in part, in the valve margins of a seed plant and having homology to the amino acid sequence of Arabidopsis AGL5 (SEQ ID NO:8). AGL5 or an AGL5 ortholog can function, in part, by forming a complex with an AGL8-like gene product as shown in Example IV. An AGL5 ortholog generally has an amino acid sequence having at least about 60% amino acid identity with Arabidopsis AGL5 (SEQ ID NO:8) and includes polypeptides having greater than about 65%, 70%, 75%, 85% or 95% amino acid identity with Arabidopsis AGL5 (SEQ ID NO:8). Given the close relatedness of the AGL1 and AGL5 gene products, one skilled in the art will recognize that an AGL5 ortholog can be distinguished from an AGL1 ortholog by being more closely related to Arabidopsis AGL5 (SEQ ID NO:8) than to Arabidopsis AGL1 (SEQ ID NO:6). An AGL5 ortholog can function in wild type plants, like Arabidopsis AGL5, to limit the domain of AGL8-like gene product expression to the carpel valves during the later stages of floral development.

The term "suppressed," as used herein in reference to AGL1 expression, means that the amount of functional AGL1 protein is reduced in a seed plant in comparison with the amount of functional AGL1 protein in the corresponding wild type seed plant. Similarly, when used in reference to AGL5 expression, the term suppressed means that the amount of functional AGL5 protein is reduced in a seed plant in comparison with the amount of functional AGL5 protein in the corresponding wild type seed plant. Thus, the term "suppressed," as used herein, encompasses the absence of AGL1 or AGL5 protein in a seed plant, as well as protein expression that is present but reduced as compared to the level of AGL1 or AGL5 protein expression in a wild type seed plant. Furthermore, the term suppressed refers to AGL1 or AGL5 protein expression that is reduced throughout the entire domain of AGL1 or AGL5 expression, or to expression that is reduced in some part of the AGL1 or AGL5 expression domain, provided that the resulting seed plant is characterized by delayed seed dispersal.

As used herein, the term "suppressed" also encompasses an amount of AGL1 or AGL5 protein that is equivalent to wild type AGL1 or AGL5 expression, but where the AGL1 or AGL5 protein has a reduced level of activity. As discussed above, AGL1 and AGL5 each contain a conserved MADS domain; point mutations or gross deletions within the MADS domain that reduce the DNA-binding activity of AGL1 or AGL5 can reduce or destroy the activity of AGL1 or AGL5 and, therefore, "suppress" AGL1 or AGL5 expression as defined herein. One skilled in the art will recognize that, preferably, AGL1 expression is essentially absent in the valve margin of a seed plant or the AGL1 protein is essentially non-functional and, similarly, that, preferably, AGL5 expression is essentially absent in the valve margin of the seed plant or the AGL5 protein is essentially non-functional.

A variety of methodologies can be used to suppress AGL1 or AGL5 expression in a seed plant. Suppression can be achieved by directly modifying the AGL1 or AGL5 genomic locus, for example, by modifying an AGL1 or AGL5 regulatory sequence such that transcription or translation from the AGL1 or AGL5 locus is reduced, or by modifying an AGL1 or AGL5 coding sequence such that non-functional AGL1 or AGL5 protein is produced. Suppression of AGL1 or AGL5 expression in a seed plant also can be achieved indirectly, for example, by modifying the expression or activity of a protein that regulates AGL1 or AGL5 expression. Methodologies for effecting suppression of AGL1 or AGL5 expression in a seed plant include, for example, homologous recombination, chemical and transposon-mediated mutagenesis, cosuppression and antisense-based techniques and dominant negative methodologies.

Homologous recombination of AGL1 or AGL5 can be used to suppress AGL1 or AGL5 expression in a seed plant as described in Kempin et al., *Nature* 389:802–803 (1997), which is incorporated herein by reference. Homologous recombination can be used, for example, to replace the wild type AGL5 genomic sequence with a construct in which the gene for kanamycin resistance is flanked by at least about 1 kb of AGL5 sequence. The use of homologous recombination to suppress AGL5 expression is set forth in Example II.

Suppression of AGL1 or AGL5 expression also can be achieved by producing a loss-of-function mutation using transposon-mediated insertional mutagenesis with Ds transposons or Stm transposons (see, for example, Sundaresan et al., *Genes Devel.* 9:1797–1810 (1995), which is incorporated herein by reference). Insertion of a transposon into an AGL1 or AGL5 target gene can be identified, for example, by restriction mapping, which can identify the presence of an insertion in the gene promoter or in the coding region, such that expression of functional gene product is suppressed. Insertion of a transposon also can be identified by detecting an absence of the mRNA encoded by the target gene or by the detecting the absence of the gene product in valve margin. Suppression of AGL1 or AGL5 expression also can be achieved by producing a loss-of-function mutation using T-DNA-mediated insertional mutagenesis (see Krysan et al., *Proc. Natl. Acad. Sci., USA* 93:8145–8150 (1996)). The use of T-DNA-mediated insertional mutagenesis to suppress AGL1 expression is disclosed in Example II.

Suppression of AGL1 or AGL5 expression in a seed plant also can be achieved using cosuppression, which is a well known methodology that relies on expression of a nucleic acid molecule in the sense orientation to produce coordinate silencing of the introduced nucleic acid molecule and the homologous endogenous gene (see, for example, Flavell, *Proc. Natl. Acad. Sci., USA* 91:3490–3496 (1994); Kooter and Mol, *Current Opin. Biol.* 4:166–171 (1993), each of which is incorporated herein by reference). Cosuppression is induced most strongly by a large number of transgene copies or by overexpression of transgene RNA and can be enhanced by modification of the transgene such that it fails to be translated.

Antisense nucleic acid molecules encoding AGL1 and AGL5 gene products, or fragments thereof, also can be used to suppress expression of AGL1 and AGL5 in a seed plant. Antisense nucleic acid molecules reduce mRNA translation or increase mRNA degradation, thereby suppressing gene expression (see, for example, Kooter and Mol, supra, 1993; Pnueli et al., *The Plant Cell Vol.* 6, 175–186 (1994), which is incorporated herein by reference).

To produce a non-naturally occurring seed plant of the invention, in which AGL1 and AGL5 expression each are suppressed, the one or more sense or antisense nucleic acid molecules can be expressed under control of a strong regulatory element that is expressed, at least in part, in the valve margin of the seed plant. The constitutive CaMV 35S promoter (Odell et al., supra, 1985), for example, or other constitutive promoters as disclosed herein, can be useful in the methods of the invention. Dehiscence zone-selective regulatory elements also can be useful for expressing one or more sense or antisense nucleic acid molecules in order to suppress AGL1 and AGL5 expression in a seed plant The skilled artisan will recognize that effective suppression of endogenous AGL1 and AGL5 gene expression depends upon the one or more introduced nucleic acid molecules having a high percentage of homology with the corresponding endogenous gene loci. Nucleic acid molecules encoding Arabidopsis AGL1 (SEQ ID NO:5) and AGL5 (SEQ ID NO:7) are provided herein (see, also, Ma et al., supra, 1991). Nucleic acid molecules encoding Arabidopsis AGL1 and AGL5 can be useful in the methods of the invention or for isolating orthologous AGL1 and AGL5 sequences.

The homology requirement for effective suppression using homologous recombination, cosuppression or antisense methodology can be determined empirically. In general, a minimum of about 80–90% nucleic acid sequence identity is preferred for effective suppression of AGL1 or AGL5 expression. Thus, a nucleic acid molecule encoding a gene ortholog from the family or genus of the seed plant species into which the nucleic acid molecule is to be introduced is preferred for generating the non-naturally occurring seed plants of the invention using homologous recombination, cosuppression or antisense technology. More preferably, a nucleic acid molecule encoding a gene ortholog from the same seed plant species is used for suppressing AGL1 expression and AGL5 expression in a seed plant of the invention. For example, nucleic acid molecules encoding canola AGL1 and AGL5 are preferable for suppressing AGL1 and AGL5 expression in a canola plant.

Although use of a highly homologous nucleic acid molecule is preferred in the methods of the invention, the nucleic acid molecule to be used for homologous recombination, cosuppression or antisense suppression need not contain in its entirety the AGL1 or AGL5 sequence to be suppressed. Thus, a sense or antisense nucleic acid molecule encoding only a portion of Arabidopsis AGL1 (SEQ ID NO:5), for example, or a sense or antisense nucleic acid molecule encoding only a portion of Arabidopsis AGL5 (SEQ ID NO:7) can be useful for producing a non-naturally occurring seed plant of the invention, in which AGL1 and AGL5 expression each are suppressed.

A portion of a nucleic acid molecule to be homologously recombined with an AGL1 or AGL5 locus generally contains at least about 1 kb of sequence homologous to the targeted gene and preferably contains at least about 2 kb, more preferably at least about 3 kb and can contain at least about 5 kb of sequence homologous to the targeted gene. A portion of a nucleic acid molecule encoding an AGL1 or AGL5 to be used for cosuppression or antisense suppression generally contains at least about 50 base pairs to the full-length of the nucleic acid molecule encoding the AGL1 or AGL5 ortholog. In contrast to an active segment, as defined herein, a portion of a nucleic acid molecule to be used for homologous recombination, cosuppression or antisense suppression need not encode a functional part of a gene product.

A dominant negative construct also can be used to suppress AGL1 or AGL5 expression in a seed plant. A dominant negative construct useful in the invention generally contains a portion of the complete AGL1 or AGL5 coding sequence sufficient, for example, for DNA-binding or for a protein-protein interaction such as a homodimeric or heterodimeric protein-protein interaction but lacking the transcriptional activity of the wild type protein. For example, a carboxy-terminal deletion mutant of AGAMOUS was used as a dominant negative construct to suppress expression of the MADS box gene AGAMOUS (Mizukami et al., *Plant Cell* 8:831–844 (1996), which is incorporated by reference herein). One skilled in the art understands that, similarly, a dominant negative AGL1 or AGL5 construct can be used to suppress AGL1 or AGL5 expression in a seed plant. A useful dominant negative construct can be a deletion mutant encoding, for example, the MADS box domain alone ("M"), the MADS box domain and "intervening" region ("MI"); the MADS box, "intervening" and "K" domains ("MIK"); or the "intervening," "K" and carboxy-terminal domains ("IKC").

In a preferred embodiment, a non-naturally occurring seed plant of the invention is an agl1 agl5 double mutant. An agl1 agl5 double mutant is a particularly useful non-naturally occurring seed plant that is characterized by delayed seed dispersal.

As used herein, the term "agl1 agl5 double mutant" means a seed plant having a loss-of-function mutation at the AGL1 locus and a loss-of-function mutation at the AGL5 locus. Loss-of-function mutations encompass point mutations, including substitutions, deletions and insertions, as well as gross modifications of an AGL1 and AGL5 locus and can be located in coding or non-coding sequences. One skilled in the art understands that any such loss-of-function mutation at the AGL1 locus can be combined with any such mutation at the AGL5 locus to generate an agl1 agl5 double mutant of the invention. Production of an exemplary agl1 agl5 double mutant in the Brassica seed plant Arabidopsis is disclosed herein in Example II.

AGL1 and AGL5 are closely related genes that have diverged relatively recently. While not wishing to be bound by the following, some plants can contain only AGL1 or only AGL5, or can contain a single ancestral gene related to AGL1 and AGL5. In such plants, a seed plant characterized by delayed seed dispersal can be produced by suppressing only expression of AGL1, or expression of AGL5, or expression of a single ancestral gene related to AGL1 and AGL5. Thus, the present invention provides a non-naturally occurring seed plant characterized by delayed seed dispersal, in which AGL1 expression is suppressed. Such a non-naturally occurring seed plant characterized by delayed seed dispersal can be, for example, an agl1 single mutant. The present invention also provides a non-naturally occurring seed plant characterized by delayed seed dispersal, in which AGL5 expression is suppressed. A non-naturally occurring seed plant characterized by delayed seed dispersal in which AGL5 expression is suppressed can be, for example, an agl5 single mutant.

The present invention further provides tissues derived from non-naturally occurring seed plants of the invention. In one embodiment, the invention provides a tissue derived from a non-naturally occurring seed plant that has an ectopically expressed nucleic acid molecule encoding an AGL8-like gene product and is characterized by delayed seed dispersal. In another embodiment, the invention provides a tissue derived from a non-naturally occurring seed plant in which AGL1 expression and AGL5expression each are suppressed, where the seed plant is characterized by delayed seed dispersal.

As used herein, the term "tissue" means an aggregate of seed plant cells and intercellular material organized into a structural and functional unit. A particular useful tissue of the invention is a tissue that can be vegetatively or non-vegetatively propagated such that the seed plant from which the tissue was derived is reproduced. A tissue of the invention can be, for example, a seed, leaf, root or part thereof.

As used herein, the term "seed" means a structure formed by the maturation of the ovule of a seed plant following fertilization. Such seeds can be readily harvested from a non-naturally occurring seed plant of the invention characterized by delayed seed dispersal.

A seed plant characterized by enhanced seed dispersal also can be produced by manipulating expression of an AGL8-like gene product or AGL1 or AGL5. Suppression of AGL8-like gene product expression in a seed plant, for example, suppression of AGL8-like gene product expression in valve tissue, can be used to produce a seed plant characterized by enhanced seed dispersal. Ectopic expression of AGL1 or AGL5, or both, in a seed plant, for example, premature expression of AGL1 or AGL5, also can be used to produce a non-naturally occurring seed plant of the invention characterized by enhanced seed dispersal. The skilled person understands that these or other strategies of manipulating AGL8, AGL1 or AGL5 expression can be used to produce a non-naturally occurring seed plant characterized by enhanced seed dispersal.

The invention also provides a substantially purified dehiscence zone-selective regulatory element, which includes a nucleotide sequence that confers selective expression upon an operatively linked nucleic acid molecule in the valve margin or dehiscence zone of a seed plant, provided that the dehiscence zone-selective regulatory element does not have a nucleotide sequence consisting of nucleotides 1889 to 2703 of SEQ ID NO:4.

As used herein, the term "dehiscence zone-selective regulatory element" refers to a nucleotide sequence that, when operatively linked to a nucleic acid molecule, confers selective expression upon the operatively linked nucleic acid molecule in a limited number of plant tissues, including the valve margin or dehiscence zone. As discussed above, the valve margin is the future site of the dehiscence zone and encompasses the margins of the outer replum as well as valve cells adjacent to the outer replum. The dehiscence zone, which develops in the region of the valve margin, refers to the group of cells that separate during the process of dehiscence, allowing valves to come apart from the replum and the enclosed seeds to be released. Thus, a dehiscence zone-selective regulatory element, as defined herein, confers selective expression in the mature dehiscence zone, or confers selective expression in the valve margin, which marks the future site of the dehiscence zone.

A dehiscence zone-selective regulatory element can confer specific expression exclusively in cells of the valve margin or dehiscence zone or can confer selective expression in a limited number of plant cell types including cells of the valve margin or dehiscence zone. An AGL5 regulatory element, for example, which confers selective expression in ovules and placenta as well as in the dehiscence zone, is a dehiscence zone-selective regulatory element as defined herein. A dehiscence zone-selective regulatory element generally is distinguished from other regulatory elements by conferring selective expression in the valve margin or dehiscence zone without conferring expression throughout the adjacent carpel valves.

The Arabidopsis AGL1 gene (SEQ ID NO:3) is shown in FIG. 7, with the intron-exon boundaries indicated. The Arabidopsis AGL5 gene (SEQ ID NO:4) is shown in FIG. 8, with the intron-exon boundaries indicated. An AGL1 or AGL5 regulatory element, such as a 5' regulatory element or intronic regulatory element, can confer selective expression in the valve margin or dehiscence zone and, thus, is a dehiscence-zone selective regulatory element as defined herein. The AGL5 gene, for example, is selectively expressed in the dehiscence zone, placenta and ovules, and an AGL5 regulatory element can confer selective expression in the dehiscence zone, placenta and ovules upon an operatively linked nucleic acid molecule.

The invention provides a dehiscence zone-selective regulatory element that is an AGL1 or AGL5 regulatory element. Such a dehiscence zone-selective regulatory element can be, for example, an AGL1 regulatory element. An AGL1 regulatory element can have, for example, the nucleotide sequence of a non-coding portion of the Arabidopsis AGL1 genomic sequence identified as SEQ ID NO:3. A dehiscence zone-selective regulatory element also can be, for example, an AGL5 regulatory element. An AGL5 regulatory element can have, for example, the nucleotide sequence of a non-coding portion of the Arabidopsis AGL5 genomic sequence identified as SEQ ID NO:4, provided that the regulatory element does not have a nucleotide sequence consisting of nucleotides 1889 to 2703 of SEQ ID NO:4.

As used herein, the term "substantially the nucleotide sequence," when used in reference to an AGL1 or AGL5 regulatory element, means a nucleotide sequence having an identical sequence, or a nucleotide sequence having a similar, non-identical sequence that is considered to be a functionally equivalent sequence by those skilled in the art. For example, a dehiscence zone-selective regulatory element that is an AGL1 regulatory element can have, for example, a nucleotide sequence identical to the sequence of the Arabidopsis AGL1 regulatory element having nucleotides 1 to 2599 of SEQ ID NO:3 shown in FIG. 7, or a similar, non-identical sequence that is functionally equivalent. A dehiscence zone-selective regulatory element can have, for example, one or more modifications such as nucleotide additions, deletions or substitutions relative to the nucleotide sequence shown in FIG. 8, provided that the modified nucleotide sequence retains substantially the ability to confer selective expression in the valve margin or dehiscence zone upon an operatively linked nucleic acid molecule.

It is understood that limited modifications can be made without destroying the biological function of an AGL1 or AGL5 regulatory element and that such limited modifications can result in dehiscence zone-selective regulatory elements that have substantially equivalent or enhanced function as compared to a wild type AGL1 or AGL5 regulatory element. These modifications can be deliberate, as through site-directed mutagenesis, or can be accident al such as through mutation in hosts harboring the regulatory element. All such modified nucleotide sequences are included in the definition of a dehiscence zone-selective regulatory element as long as the ability to confer selective express ion in the valve margin or dehiscence zone is substantially retained.

A dehiscence zone-selective regulatory element can be derived from a gene that is an ortholog of Arabidopsis AGL1 or AGL5 and is selectively expressed in the valve margin or dehiscence zone of a seed plant. A dehiscence zone-selective regulatory element can be derived, for example, from an AGL1 or AGL5 ortholog of the Brassicaceae, such as a *Brassica napus, Brassica oleracea, Brassica campestris, Brassica juncea, Brassica nigra* or *Brassica carinata* AGL1 or AGL5 ortholog. A dehiscence zone-selective regulatory element can be derived, for example, from an AGL1 or AGL5 canola ortholog. A dehiscence zone-selective regulatory element also can be derived, for example, from a leguminous AGL1 or AGL5 ortholog, such as a soybean, pea, chickpea, moth bean, broad bean, kidney bean, lima bean, lentil, cowpea, dry bean, peanut, alfalfa, lucerne, birdsfoot trefoil, clover, stylosanthes, lotononis bainessii, or sainfoin AGL1 or AGL5 ortholog.

Dehiscence zone-selective regulatory elements also can be derived from a variety of other genes that are selectively expressed in the valve margin or dehiscence zone of a seed plant. For example, the rapeseed gene RDPG1 is selectively expressed in the dehiscence zone (Petersen et al., *Plant Mol. Biol.* 31:517–527 (1996), which is incorporated herein by reference). Thus, the RDPG1 promoter or an active fragment thereof can be a dehiscence zone-selective regulatory element as defined herein. Additional genes such as the rapeseed gene SAC51 also are known to be selectively expressed in the dehiscence zone; the SAC51 promoter or an active fragment thereof also can be a dehiscence zone-selective regulatory element of the invention (Coupe et al., *Plant Mol. Biol.* 23:1223–1232 (1993), which is incorporated herein by reference). Further, genes selectively expressed in the dehiscence zone include the gene that confers selective GUS expression in the Arabidopsis transposant line GT140 (Sundaresan et al., *Genes Devel.* 9:1797–1810 (1995), which is incorporated herein by reference). The skilled artisan understands that a regulatory element of any such gene selectively expressed in cells of the valve margin or dehiscence zone can be a dehiscence zone-selective regulatory element as defined herein.

Additional dehiscence zone-selective regulatory elements can be identified and isolated using routine methodology. Differential screening strategies using, for example, RNA prepared from the dehiscence zone and RNA prepared from adjacent pod material can be used to isolate cDNAs selectively expressed in cells of the dehiscence zone (Coupe et al., supra, 1993); subsequently, the corresponding genes are isolated using the cDNA sequence as a probe.

Enhancer trap or gene trap strategies also can be used to identify and isolate a dehiscence zone-selective regulatory element of the invention (Sundaresan et al., supra, 1995; Koncz et al., *Proc. Natl. Acad. Sci. USA* 86:8467–8471 (1989); Kertbundit et al., *Proc. Natl. Acad. Sci. USA* 88:5212–5216 (1991); Topping et al., *Development* 112:1009–1019 (1991), each of which is incorporated herein by reference). Enhancer trap elements include a reporter gene such as GUS with a weak or minimal promoter, while gene trap elements lack a promoter sequence, relying on transcription from a flanking chromosomal gene for reporter gene expression. Transposable elements included in the constructs mediate fusions to endogenous loci; constructs selectively expressed in the valve margin or dehiscence zone are identified by their pattern of expression. With the inserted element as a tag, the flanking dehiscence zone-selective regulatory element is cloned using, for example, inverse polymerase chain reaction methodology (see, for example, Aarts et al., *Nature* 363:715–717 (1993); see, also, Ochman et al., "Amplification of Flanking Sequences by Inverse PCP," in Innis et al., supra, 1990). The Ac/Ds transposition system of Sundaresan et al., supra, 1995, can be particularly useful in identifying and isolating a dehiscence zone-selective regulatory element of the invention.

Dehiscence zone-selective regulatory elements also can be isolated by inserting a library of random genomic DNA fragments in front of a promoterless reporter gene and screening transgenic seed plants transformed with the library for dehiscence zone-selective reporter gene expression. The promoterless vector pROA97, which contains the npt gene and the GUS gene each under the control of the minimal 35S promoter, can be useful for such screening. The genomic library can be, for example, Sau3A fragments of *Arabidopsis thaliana* genomic DNA or genomic DNA from, for example, another Brassicaceae of interest (Ott et al., *Mol. Gen. Genet.* 223:169–179 (1990); Claes et al., *The Plant Journal* 1:15–26 (1991), each of which is incorporated herein by reference).

Dehiscence zone-selective expression of a regulatory element of the invention can be demonstrated or confirmed by routine techniques, for example, using a reporter gene and in situ expression analysis. The GUS and firefly luciferase reporters are particularly useful for in situ localization of plant gene expression (Jefferson et al., *EMBO J.* 6:3901 (1987); Ow et al., *Science* 334:856 (1986), each of which is incorporated herein by reference), and promoterless vectors containing the GUS expression cassette are commercially available, for example, from Clontech (Palo Alto, Calif.). To identify a dehiscence zone-selective regulatory element of interest such as an AGL1 or AGL5 regulatory element, one or more nucleotide portions of the AGL1 or AGL5 gene can be generated using enzymatic or PCR-based methodology (Glick and Thompson, supra, 1993; Innis et al., supra, 1990); the resulting segments are fused to a reporter gene such as GUS and analyzed as described above.

The present invention also provides a substantially purified dehiscence zone-selective regulatory element that confers selective expression upon an operatively linked nucleic acid molecule in the valve margin or dehiscence zone of a seed plant, where the element is an AGL1 regulatory element having at least fifteen contiguous nucleotides of one of the following nucleotide sequences: nucleotides 1 to 2599 of SEQ ID NO:3; nucleotides 2833 to 4128 of SEQ ID NO:3; nucleotides 4211 to 4363 of SEQ ID NO:3; nucleotides 4426 to 4554 of SEQ ID NO:3; nucleotides 4655 to 4753; nucleotides 4796 to 4878 of SEQ ID NO:3; nucleotides 4921 to 5028 of SEQ ID NO:3; or nucleotides 5361 to 5622 of SEQ ID NO:3. A substantially purified dehiscence zone-selective regulatory element that is an AGL1 regulatory element can have, for example, at least 16, 18, 20, 25, 30, 40, 50, 100 or 500 contiguous nucleotides of one of the portions of SEQ ID NO:3 described above.

The present invention also provides a substantially purified dehiscence zone-selective regulatory element that confers selective expression upon an operatively linked nucleic acid molecule in the valve margin or dehiscence zone of a seed plant, where the element is an AGL5 regulatory element having at least fifteen contiguous nucleotides of one of the following nucleotide sequences: nucleotides 1 to 1888 of SEQ ID NO:4; nucleotides 2928 to 5002 of SEQ ID NO:4; nucleotides 5085 to 5204 of SEQ ID NO:4; nucleotides 5367 to 5453 of SEQ ID NO:4; nucleotides 5496 to 5602; nucleotides 5645 to 5734 of SEQ ID NO:4; or nucleotides 6062 to 6138 of SEQ ID NO:4. A substantially purified dehiscence zone-selective regulatory element that is an AGL5 regulatory element can have, for example, at least 16, 18, 20, 25, 30, 40, 50, 100 or 500 contiguous nucleotides of one of the portions of SEQ ID NO:4 described above.

A proximal fragment of the Arabidopsis AGL5 promoter has been described (Savidge et al., *The Plant Cell* 7:721–733 (1995)). However, this fragment (shown as nucleotides 1889 to 2703 in FIG. 8) lacks many of the distal regulatory elements contained in the entire Arabidopsis AGL5 genomic sequence disclosed herein (SEQ ID NO:4). The present invention provides approximately 2.7 kb of Arabidopsis AGL5 5' flanking sequence, including the variety of regulatory elements contained therein. The disclosed Arabidopsis AGL5 5' flanking sequence contains a larger complement of regulatory elements involved in regulating expression of the endogenous AGL5 gene in vivo and, therefore, can be particularly useful for dehiscence zone-selective expression.

A nucleotide sequence consisting of the promoter proximal region of Arabidopsis AGL5 (nucleotides 1889 to 2703 of SEQ ID NO:4) is explicitly excluded from a dehiscence zone-selective regulatory element of the invention. However, a dehiscence zone-selective regulatory element can include nucleotides 1889 to 2703 of SEQ ID NO:4, together with one or more contiguous nucleotides, for example, of the nucleotide sequence shown as positions 1 to 1888 of SEQ ID NO:4. A dehiscence zone-selective regulatory element of the invention can have, for example, at least 15 contiguous nucleotides of SEQ ID NO:4, including at least one, two, four, six, ten, twenty or thirty or more contiguous nucleotides of the nucleotide sequence shown as positions 1 to 1888 of SEQ ID NO:4.

In view of the definition of a dehiscence zone-selective regulatory element, it should be recognized, for example, that a portion of the Arabidopsis AGL5 gene having only the sequence shown as nucleotides 1889 to 2703 in FIG. 8 (SEQ ID NO:4), is not a dehiscence zone-selective regulatory element as defined herein. However, a portion of an Arabidopsis AGL5 gene having nucleotides 1885 to 2703 of SEQ ID NO:4 is considered a dehiscence zone-selective regulatory element, provided that the element confers selective expression upon an operatively linked nucleic acid molecule in a limited number of plant tissues, including the valve margin or dehiscence zone. Similarly, a portion of an Arabidopsis AGL5 gene having a subpart of the promoter proximal region of AGL5 also can be a dehiscence zone-selective regulatory element as defined herein, provided that this subpart can confer selective expression upon an operatively linked nucleic acid molecule in a limited number of plant tissues, including the valve margin or dehiscence zone of a seed plant. Thus, for example, a regulatory element having the sequence of nucleotides 1889 to 2000 can be a dehiscence zone-selective regulatory element of the invention, provided that this element confers selective expression upon an operatively linked element in the valve margin or dehiscence zone of a seed plant.

The present invention also provides a recombinant nucleic acid molecule that includes a dehiscence zone-selective regulatory element operatively linked to a nucleic acid molecule encoding a cytotoxic gene product. Further provided herein is a non-naturally occurring seed plant of the invention that is characterized by delayed seed dispersal due to expression of a recombinant nucleic acid molecule having a dehiscence zone-selective regulatory element operatively linked to a nucleic acid molecule encoding a cytotoxic gene product.

A cytotoxic gene product is a gene product that causes the death of the cell in which it is expressed and, preferably, does not result in the death of cells other than the cell in which it is expressed. Thus, expression of a cytotoxic gene product from a dehiscence zone-selective regulatory element can be used to ablate the dehiscence zone without disturbing neighboring cells of the replum or valve. A variety of cytotoxic gene products useful in seed plants are known in the art including, for example, diphtheria toxin A chain polypeptides; RNase T1; Barnase RNase; ricin toxin A chain polypeptides; and herpes simplex virus thymidine kinase (tk) gene products. While the diphtheria toxin A chain, RNase T1 and Barnase RNase are preferred cytotoxic gene products, the skilled person recognizes that these, or other cytotoxic gene products can be used with a dehiscence zone-selective regulatory element to generate a non-naturally occurring seed plant characterized by delayed seed dispersal.

Diphtheria toxin is the naturally occurring toxin of Cornebacterium diphtheriae, which catalyzes the ADP-ribosylation of elongation factor 2, resulting in inhibition of protein synthesis and consequent cell death (Collier, *Bacteriol. Rev.* 39:54–85 (1975)). A single molecule of the fully active toxin is sufficient to kill a cell (Yamaizumi et al., *Cell* 15:245–250 (1978)). Diphtheria toxin has two subunits: the diphtheria toxin B chain directs internalization to most eukaryotic cells through a specific membrane receptor, whereas the A chain encodes the toxic catalytic domain. The catalytic DT-A chain does not include a signal peptide and is not secreted. Further, any DT-A released from dead cells in the absence of the diphtheria toxin B chain is precluded from cell attachment. Thus, DT-A is cell autonomous and directs killing only of the cells in which it is expressed without apparent damage to neighboring cells. The DT-A expression cassette of Palmiter et al., which contains the 193 residues of the A chain engineered with a synthetic ATG and lacking the native leader sequence, is particularly useful in the seed plants of the invention (Palmiter et al., *Cell* 50:435–443 (1987); Greenfield et al., *Proc. Natl. Acad. Sci., USA* 80:6853–6857 (1983), each of which is incorporated herein by reference)

RNase T1 of Aspergillus oryzae and Barnase RNase of Bacillus amylolique-faciens also are cytotoxic gene products useful in the seed plants of the invention (Thorsness and Nasrallah, *Methods in Cell Biology* 50:439–448 (1995)). Barnase RNase may be more generally toxic to plants than RNase T1 and, thus, is preferred in the methods of the invention.

Ricin, a ribosome-inactivating protein produced by castor bean seeds, also is a cytotoxic gene product useful in a non-naturally occurring seed plant of the invention. The ricin toxin A chain polypeptide can be used to direct cell-specific ablation as described, for example, in Moffat et al., *Development* 114:681–687 (1992). Plant ribosomes are variably susceptible to the plant-derived ricin toxin. The skilled person understands that the toxicity of ricin depends is variable and should be assessed for toxicity in the seed plant species of interest (see Olsnes and Pihl, *Molecular Action of Toxins and Viruses,* pages 51–105, Amsterdam: Elsevier Biomedical Press (1982)).

Further provided herein is a plant expression vector including a dehiscence zone-selective regulatory element. A plant expression vector can include, if desired, a nucleic acid molecule encoding an AGL8-like gene product in addition to the dehiscence zone-selective regulatory element.

The term "plant expression vector," as used herein, is a self-replicating nucleic acid molecule that provides a means to transfer an exogenous nucleic acid molecule into a seed plant host cell and to express the molecule therein. Plant expression vectors encompass vectors suitable for Agrobacterium-mediated transformation, including binary and cointegrating vectors, as well as vectors for physical transformation.

Plant expression vectors can be used for transient expression of the exogenous nucleic acid molecule, or can integrate and stably express the exogenous sequence. One skilled in the art understands that a plant expression vector can contain all the functions needed for transfer and expression of an exogenous nucleic acid molecule; alternatively, one or more functions can be supplied in trans as in a binary vector system for Agrobacterium-mediated transformation.

In addition to a dehiscence zone-selective regulatory element, a plant expression vector of the invention can contain, if desired, additional elements. A binary vector for Agrobacterium-mediated transformation contains one or both T-DNA border repeats and can also contain, for example, one or more of the following: a broad host range replicon, an ori T for efficient transfer from *E. coli* to Agrobacterium, a bacterial selectable marker such as ampicillin and a polylinker containing multiple cloning sites.

A plant expression vector for physical transformation can have, if desired, a plant selectable marker in addition to a dehiscence zone-selective regulatory element in vectors such as pBR322, pUC, PGEM and M13, which are commercially available, for example, from Pharmacia (Piscataway, N.J.) or Promega (Madison, Wis.). In plant expression vectors for physical transformation of a seed plant, the T-DNA borders or the ori T region can optionally be included but provide no advantage.

The present invention also provides a kit for producing a transgenic seed plant characterized by delayed seed dispersal. A kit of the invention contains a dehiscence zone-selective regulatory element. If desired, the dehiscence zone-selective regulatory element can be operatively linked to a nucleic acid molecule encoding an AGL8-like gene product.

The following examples are intended to illustrate but not limit the present invention.

EXAMPLE I

PRODUCTION OF A 35S-AGL8 TRANSGENIC ARABIDOPSIS PLANT DISPLAYING A COMPLETE LACK OF DEHISCENCE

This example describes methods for producing a transgenic Arabidopsis plant lacking normal dehiscence due to constitutive AGL8 expression.

Full-length AGL8 was prepared by polymerase chain reaction amplification using primer AGL8 5-γ (SEQ ID NO:9; 5'-CCGTCGACGATGGGAAGAGGTAGGGTT-3') and primer OAM14 (SEQ ID NO:10; 5'-AATCATTACCAAGATATGAA-3'), and subsequently cloned into the SalI and BamHI sites of expression vector pBIN-JIT, which was modified from pBIN19 to include the tandem CaMV 35S promoter, a polycloning site and the CaMV polyA signal. Arabidopsis was transformed using the in planta method of Agrobacterium-mediated transformation essentially as described in Bechtold et al., *C.R. Acad. Sci. Paris* 316:1194–1199 (1993), which is incorporated herein by reference. Kanamycin-resistant lines were analyzed for the presence of the 35S-AGL8 construct by PCR using a primer specific for the 35S promoter and a primer specific for the AGL8 cDNA, which produced two fragments of 850 and 550 bp in the 35S-AGL8 transgenic plants. These fragments were absent in plants that had not been transformed with the 35S-AGL8 construct.

The phenotype of approximately 35 35S::AGL8 lines was analyzed. Of the 35 lines, 7 lines exhibited a complete lack of dehiscence. In these lines, the mature fruits did not release their seeds unless opened manually. Several of the remaining 35S::AGL8 lines exhibited delayed dehiscence, whereby seeds were released at least a week later than in wild type Arabidopsis plants.

EXAMPLE II

PRODUCTION OF AN ARABIDOPSIS agl1 agl5 double mutant DISPLAYING A COMPLETE LACK OF DEHISCENCE This example describes the production of an agl1 agl5 double mutant displaying a complete lack of normal dehiscence.

A. Production of an agl5 Mutant by Homologous Recombination

A PCR-based assay of transgenic plants was used to identify targeted insertions into AGL5 as described in Kempin et al., *Nature* 389:802–803 (1997), which is incorporated herein by reference. The targeting construct consisted of a kanamycin-resistance cassette that was inserted between approximately 3 kb and 2 kb segments representing the 5' and 3' regions of the AGL5 gene, respectively. A successfully targeted insertion produces a 1.6 kb deletion within the AGL5 gene such that the targeted allele encodes only the first 42 of 246 amino acid residues, and only 26 of the 56 amino acids comprising the DNA-binding MADS-domain. The recombination event also results in the insertion of the 2.5 kb kanamycin-resistance cassette within the AGL5 coding sequence.

750 kanamycin-resistant transgenic lines were produced by Agrobacterium-mediated transformation, and pools of transformants were analyzed using a PCR assay as described below to determine if any of these primary transformants had generated the desired targeted insertion into AGL5. A single line was identified that appeared to contain the anticipated insertion, and this line was allowed to self-pollinate to permit further analyses in subsequent generations. Genomic DNA from the homozygous mutant plants was analyzed with more than four different restriction enzymes and by several distinct PCR amplifications, and all data were consistent with the desired targeting event. The regions flanking the AGL5 gene also were analyzed to verify that there were no detectable deletions or rearrangements of sequences outside of AGL5.

The kanamycin-resistance cassette within the AGL5 targeting construct contains sequences that specify transcription termination such that little or no AGL5 RNA was expected in the homozygous mutant plants. Using a probe specific for the 3' portion of the AGL5 cDNA, AGL5 transcripts were detected in wild-type but not in agl5 mutant plants. These data indicate that the targeted disruption of the AGL5 gene represents a loss-of-function allele.

Characterization of the agl5 line indicated that the phenotype of this transgenic was not different from wild type Arabidopsis.

The AGL5 knockout (KO) construct was prepared in vector pZM104A, which carries the kanamycin-resistance cassette flanked by several cloning sites (Miao and Lam, Plant J. 7:359–365 (1995), which is incorporated herein by reference). Vector pZM104A also contains the gene encoding δ-glucuronidase (GUS), which allows the differentiation of non-homologous from homologous integration events. The 3 kb region representing the 5' portion of AGL5 was obtained by PCR amplification using primer SEQ ID NO:11 (5'-CGGATAGCTCGAATATCG-3') and primer SEQ ID NO:12 (5'-AACCATTGCGTCGTTTGC-3'). The resulting fragment was cloned into vector pCRII (Invitrogen), and an EcoRI fragment excised and inserted into the EcoRI site of pZM104A. The 3' portion of AGL5 was excised as an XbaI fragment from an AGL5 genomic clone in the vector pCIT30 (Ma et al., Gene 117:161–167 (1992), which is incorporated by reference herein) and inserted into the XbaI site of pZM104A. The resulting plasmid, designated AGL5 KO, was used in Agrobacterium-mediated infiltration of wild-type Arabidopsis plants of the Columbia ecotype. The knockout construct was derived from Landsberg erecta genomic DNA.

Plants containing a homologous recombination event at the AGL5 genomic locus were identified as follows. Approximately 750 primary (Ti) kanamycin-resistant transformants were selected, and DNA was extracted from individual leaves in pools representing ten plants as described in Edwards et al., Nucleic Acids Research 19:1349 (1991), which is incorporated by reference herein. To identify a pool that contained a candidate targeted disruption, isolated DNAs were subjected to PCR amplification using primer SEQ ID NO:13 (5'-GTAATTACCAGGCAAGGACTCTCC-3'), which represents AGL5 genomic sequence that is not contained within the AGL5 KO construct, and primer SEQ ID NO:14 (5'-GTCATCGGCGGGGGTCATAACGTG-3'), which is specific for the kanamycin-resistance cassette. Amplified products were size fractionated on agarose gels, and used for standard DNA blotting assays with probe 1. One pool of ten plants revealed the anticipated hybridizing band of the correct size, and this pool was subsequently broken down into individual plants. A single (T1) plant was identified that appeared to contain the desired event, and this plant was allowed to self-pollinate for analyses in subsequent generations. This T1 plant was shown to contain the GUS-reporter gene, indicating that in addition to the putative homologous integration event, there were independent non-homologous events. Segregation in the subsequent generations allowed the identification of plants that no longer contained the GUS-reporter gene, and it was these lines that were used for subsequent analyses.

Plants homozygous for the disruption were identified by PCR amplification using primers SEQ ID NO:15 (5'-GAGGATAGAGAACACTACGAATCG-3') and SEQ ID NO:16 (5'-CAGGTCAAGTCAATAGATTC-3'), which yielded a single 1.5 kb product in wild type plants, and a single 2.6 kb product in the mutant. Further confirmation that these plants contained the desired disruption was obtained by PCR amplification with primers SEQ ID NO:17 (5'-CAGAATTTAGTGAATAATATTG-3') and SEQ ID NO:14, which gave the expected amplified product in the mutant but no product in wild-type plants.

To confirm that the desired disruption had occurred, a series of genomic DNA blots representing wild-type and homozygous mutant (T4 generation) plants were analyzed. Probe 1 hybridized to the expected 3.9 kb XbaI fragment in wild-type and mutant plants, whereas the 1.3 kb XbaI fragment was present only in wild-type. This same probe hybridized to a 6 kb EcoRI fragment in wild-type and to the expected 4.1 and 2.8 kb EcoRI fragments in the mutant. Additional digests with BglII and with HindIII confirmed that the mutant plants contained the desired targeted event. To confirm that there were no detectable deletions or rearrangements outside the targeted region, genomic DNA blots of wild type and homozygous mutant plants were further analyzed. Probe 2 hybridized in wild-type and mutant DNAs to the expected 2.9 kb XmnI fragment, the 1.5 kb and 0.4 kb HincII fragments, and the 0.6 kb HindIII fragment. Probe 3 hybridized in wild-type and mutant DNAs to the 9 kb ScaI fragment, the 3.9 kb XbaI fragment, and the 1.8 kb NdeI fragments. The faintly-hybridizing bands in the ScaI digests represent fragments that span the insertion site, and are, as expected, different sizes in wild-type and agl5 mutant plants.

RNA blotting analyses were performed as follows. Approximately 6 µg of polyA+ RNA was purified using Dynabeads (Dynal) from wild-type and agl5 mutant inflorescences, size fractionated and hybridized using standard procedures (Crawford et al., Proc. Natl. Acad. Sci. USA 83:8073–8076 (1986), which is incorporated herein by reference) using a gel-purified 450 bp HindIII-EcoRI fragment from pCIT2242 (Ma et al., supra, 1991) specific for the 3' end of the AGL5 cDNA. The same filter was subsequently stripped and re-hybridized with a tubulin-specific probe (Marks et al., Plant Mol. Biol. 10:91–104 (1987), which is incorporated herein by reference). Hybridization with the tubulin probe verified that approximately equal amounts of RNA were present in each lane.

B. Production of an agl1 Mutant

A PCR-based screen was used to identify a T-DNA insertion into the AGL1 gene essentially as described in Krysan et al., supra, 1996.

RNA blotting analyses demonstrated that AGL1 RNA was not expressed. The agl1 mutant displayed essentially a wild type phenotype.

C. Production and Characterization of an agl1 agl5 Double Mutant agl1 agl5 double mutants were generated by crossing the agl1 and agl5 single mutants. RNA blotting experiments of the agl1 agl5 double mutant are performed as described above. The results indicate that neither AGL1 nor AGL5 RNA is expressed in the agl1 agl5 double mutant.

In contrast to the agl1 and agl5 single mutants, which had essentially the phenotype of wild type Arabidopsis, analyses of the agl1 agl5 double mutant by scanning electron microscopy indicated that the dehiscence zone failed to develop normally. Furthermore, the mature fruits of the agl1 agl5 double mutant failed to dehisce. This delayed seed dispersal phenotype was similar to AGL8 gain-of-function phenotype seen in 35S-AGL8 transgenic plants. These results indicate that the AGL1 and AGL5 genes are functionally redundant and that their encoded gene products regulate pod dehiscence. The similarity of the 35S::AGL8 and agl1 agl5 double mutant phenotypes, as well the yeast two-hybrid results described below, indicate that AGL1 and AGL8 or AGL5 and AGL8 can interact to regulate the dehiscence process.

D. Analysis of Dehiscence Phenotypes Under Various Conditions

Studies of pod dehiscence in *Brassica napus* L. using transmission electron microscopic analyses have shown that the middle lamella of the dehiscence zone cells degenerates during dehiscence, allowing the valves to separate from the replum (Petersen et al., supra, 1996). Similar analyses are performed on the agl1 agl5 double mutant as well as wild type Arabidopsis and agl1 and agl5 single mutants.

Previous studies have shown that pod dehiscence is greater when temperatures are high and the relative humidity is low. The dehiscence phenotype of the agl1 agl5 double mutant described above was observed for plants grown under continuous-light at 25 degrees C. In order to determine if the phenotype of agl1 agl5 double mutants is sensitive to environmental conditions, the analyses described above are repeated under various environmental conditions including varying temperature, varying humidity and short-day versus continuous light conditions.

EXAMPLE III

PRODUCTION OF A TRANSGENIC ARABIDOPSIS PLANT EXPRESSING AGL8 UNDER CONTROL OF THE AGL1 PROMOTER

This example demonstrates that a transgenic seed plant expressing AGL8 under control of a dehiscence zone-selective promoter is characterized by delayed seed dispersal.

AGL1::AGL8 Transgenic Plants

Ectopic expression of AGL8 under control of the 35S promoter prevents pod shatter since the dehiscence zone fails to differentiate normally. However, constitutive AGL8 expression conferred by the 35S promoter also results in other changes, including early flowering. In order to specifically control dehiscence, AGL8 is expressed from a dehiscence zone-selective regulatory element, such as one derived from a regulated promoter that is normally expressed in valve margin, as described below.

An AGL8 expression construct under control of the dehiscence zone-selective 2.5 kb AGL1 promoter fragment and first AGL1 intronic sequence is prepared as follows. The 2.5 kb AGL1 promoter fragment is amplified by PCR with primers AGL1pds (SEQ ID NO:18; 5'-GCCAGAGATAATGCTATTCC-3') and AGL1pus (SEQ ID NO:19; 5'-CATTGATCCATATATGACATCAC-3'), and the first coding exon of AGL8 is amplified with oligos AGL8eds (SEQ ID NO:20; 5'-GTGATGTCATAT ATGGATCAATGGGAAGAGGTAGGGTTCAG-3') and AGL8eus (SEQ ID NO:21; 5'-CAAGAGTCGGTGGAA TATTCG-3'). In addition, the first intron of AGL1, which can contain regulatory elements, is amplified with oligos AGL1ids (SEQ ID NO:22; 5'-CGAATATTCCACCGA CTCTTGGTACGCTTC TCCTACTCTAT-3') and AGL1iup (SEQ ID NO:23; 5'-CTAATAAGTAAGATCGCGGAA-3'). The remainder of the AGL8 coding region is amplified with oligos AGL8rds (SEQ ID NO:24; 5'-TTCCGCGAT CTTACTTATTAGCATGGAGAGGATACTTGAAC-3') and OAM14 (SEQ ID NO:10). Using PCR with oligos AGL1pds (SEQ ID NO:18) and OAM14 (SEQ ID NO:10), the four fragments are combined in the following order: AGL1 promoter, first AGL8 exon, first AGL1 intron and remainder of AGL8 coding sequence. The resulting 4.6 kb fragment is cloned into vector pCFM83, which is a vector based on pBIN19 that is modified to contain a BASTA resistance gene and 3' NOS termination sequence.

A second AGL8 expression construct, in which AGL8 is under control of the dehiscence zone-selective 2.5 kb AGL1 promoter fragment alone, is prepared as follows. The 2.5 kb AGL1 promoter fragment is amplified by PCR with oligo AGL1pds (SEQ ID NO:18) and AGL1pus (SEQ ID NO:19), and the coding region of AGL8 amplified with oligos AGL8eds (SEQ ID NO:20) and OAM14 (SEQ ID NO:10). Using PCR with oligos AGL1 pds (SEQ ID NO:18) and OAM14 (SEQ ID NO:10), the 3.5 kb fragment is cloned into vector pCFM83.

Arabidopsis plants are transformed with the two AGL1-AGL8 constructs described above. BASTA resistant plants containing the AGL1::AGL8 transgene with or without the AGL1 intron are selected. Phenotypic analysis indicates that transformed plants containing either of these constructs are characterized by delayed dehiscence. However, the AGL1::AGL8 transgenic plants differ from 35S::AGL8 transgenic plants in that an enlarged fruit or early flowering phenotype generally is not seen.

These results indicate that a transgenic seed plant expressing AGL8 under control of an AGL1 dehiscence zone-selective regulatory element is characterized by delayed seed dispersal.

EXAMPLE IV

AGL8 INTERACTS WITH AGL5 IN YEAST

This example demonstrates that, in a yeast two-hybrid system, the AGL8 gene product interacts with AGL5.

The "interaction trap" of Finley and Brent (*Gene Probes: A Practical Approach* (1994); see, also Gyuris et al., *Cell* 75:791–803 (1993)) is a variation of the yeast two-hybrid system of Fields and Song, *Nature* 340:245–246 (1989). In this system, a first protein is fused to a DNA-binding domain, and a second is fused to a transcriptional activation domain. An interaction between the Arabidopsis AGL5 and AGL8 gene products was assayed by activation of a lacZ reporter gene.

The "bait" and "prey" constructs were prepared in single copy centromere plasmids pBI-880 and pBI-771, respectively, which each contain the constitutive ADH1 promoter and are essentially as described by Chevray and Nathans, *Proc. Natl. Acad. Sci. USA* 89:5789–5793 (1992). The bait construct contains the GAL4 DNA-binding domain (amino acids 1 to 147) fused to the full-length AGL8 coding sequence. The prey construct has the full-length coding sequence of AGL5 fused to the GAL4 transcriptional activation domain (amino acids 768–881), following a nuclear localization sequence. The bait and prey constructs were assayed in the YPB2 strain of S. cerevisiae, which is deficient for GAL4 and GAL80 and which contains an integrated lacZ reporter gene under control of GAL1 promoter elements (Feilotter et al., *Nucleic Acids Research* 22:1502–1503 (1994)).

An interaction of the AGL8 "bait" and AGL5 "prey" was demonstrated in the YPB2 strain by the development of blue colonies on X-GAL containing media. Control "bait"-"prey" combinations, including the GAL4(1–147) DNA binding domain and GAL4 transcriptional activation domain only produced only white colonies. These results demonstrate that AGL8 can interact with AGL5 in yeast and indicate that the AGL8 and AGL5 plant MADS box gene products also can interact in seed plants.

All journal article, reference, and patent citations provided above, in parentheses or otherwise, whether previously stated or not, are incorporated herein by reference.

Although the invention has been described with reference to the examples above, it should be understood that various modifications can be made without departing from the spirit of the invention. Accordingly, the invention is limited only by the following claims.

We claim:

1. A non-naturally occurring seed plant, in which AGL1 expression and AGL5 expression each are suppressed, said seed plant characterized by delayed seed dispersal.

2. The non-naturally occurring seed plant of claim 1, which is an agl1 agl5 double mutant.

3. The non-naturally occurring seed plant of claim 1, wherein AGL1 is at least 63% identical to SEQ ID NO:6 and AGL5 is at least 60% identical to SEQ ID NO:8.

4. The non-naturally occurring seed plant of claim 1, wherein AGL1 is at least 75% identical to SEQ ID NO:6 and AGL5 is at least 75% identical to SEQ ID NO:8.

5. The non-naturally occurring seed plant of claim 1, wherein AGL1 is at least 95% identical to SEQ ID NO:6 and AGL5 is at least 95% identical to SEQ ID NO:8.

6. A tissue derived from a non-naturally occurring seed plant, in which AGL1 expression and AGL5 expression each are suppressed, said seed plant characterized by delayed seed dispersal.

7. The tissue of claim 6, which is a seed.

8. The tissue of claim 6, wherein AGL1 is at least 63% identical to SEQ ID NO:6 and AGL5 is at least 60% identical to SEQ ID NO:8.

9. The tissue of claim 6, wherein AGL1 is at least 75% identical to SEQ ID NO:6 and AGL5 is at least 75% identical to SEQ ID NO:8.

10. The tissue of claim 6, wherein AGL1 is at least 95% identical to SEQ ID NO:6 and AGL5 is at least 95% identical to SEQ ID NO:8.

* * * * *